US006844180B2

(12) United States Patent
Oi et al.

(10) Patent No.: US 6,844,180 B2

(45) Date of Patent: Jan. 18, 2005

(54) SERINE PROTEASE GENES RELATED TO DPPIV

(75) Inventors: Steve Oi, San Diego, CA (US); Karen O. Akinsanya, San Diego, CA (US); Pierre J-M Riviere, San Diego, CA (US); Jean-Louis Junien, Paris (FR)

(73) Assignee: Ferring BV (NL)

( * ) Notice: Subject to any disclaimer, the term of this patent is extended or adjusted under 35 U.S.C. 154(b) by 48 days.

(21) Appl. No.: 09/976,674

(22) Filed: Oct. 12, 2001

(65) Prior Publication Data

US 2002/0115843 A1 Aug. 22, 2002

Related U.S. Application Data

(60) Provisional application No. 60/240,117, filed on Oct. 12, 2000.

(51) Int. Cl.[7] ............................ C12N 9/62; C12N 5/00; C12N 15/00; C12N 1/20; C07H 21/04

(52) U.S. Cl. ..................... 435/226; 536/23.2; 536/24.5; 435/219; 435/325; 435/320.1; 435/252.3; 435/348

(58) Field of Search .............................. 435/352.3, 320, 435/226, 348, 219, 325; 536/23.2, 24.31, 23.1, 24.5; 530/350

(56) References Cited

U.S. PATENT DOCUMENTS

| | | | | |
|---|---|---|---|---|
| 6,201,132 | B1 | 3/2001 | Jenkins et al. | 548/535 |
| 6,291,662 | B1 | 9/2001 | Bandyopadhyay et al. | 536/23.5 |

FOREIGN PATENT DOCUMENTS

| | | | |
|---|---|---|---|
| WO | WO 00 42201 | A | 7/2000 |
| WO | WO 00 58473 | A | 10/2000 |
| WO | WO 01/19866 | A1 | 3/2001 |
| WO | WO 01 55399 | A | 8/2001 |

OTHER PUBLICATIONS

Abbott et al., Cloning, expression and chromosomal localization of a novel human dipeptidyl peptidase (DPP) IV homology, DPP8, *Eur. J. Biochem. 267*, 6140–6150 (2000).

Nagase T et al.: "Prediction of the Coding Sequences of Unidentified Human Genes." *DNA Research*, Universal Academy Press, JP, vol. 7, No. 2, Apr. 28, 2000.

Swallprot 'Online!' Oct. 1, 2000, EBI Database accession No. Q9P236 (2 pages).

Yokotani N et. al.: "Non–Conservation of a Catalytic Residue in a Dipeptidyl Aminopeptidase IV–Related Protein Encoded by a Gene on Human Chromosome 2" *Human Molecular Genetics*, vol. 2, No. 7, Jul. 1993, pp. 1037–1039.

Swallprot 'Online!' Nov. 1, 1995, retrieved from EBI Database accession No. P42658 (2 pages).

*Primary Examiner*—Rebecca E. Prouty
*Assistant Examiner*—Malgorzata A. Walicka
(74) *Attorney, Agent, or Firm*—Fitch, Even, Tabin & Flannery

(57) ABSTRACT

Novel proteins or polypeptides having significant sequence homology to DPPIV, nucleic acids coding therefor, cells which have been modified with such nucleic acid so as to express these proteins, antibodies to these proteins, screening methods for the discovery of new therapeutic agents which are inhibitors of the activity of these proteins or of related proteins, and therapeutic agents discovered by such screening methods, as well as new therapeutic treatments, are all provided.

16 Claims, 5 Drawing Sheets

```
DPP4    1   ..............................MKTP VLG IS....AAA LVT
DPRP1   1   MAAAMETEQLGVE FE DC EN ES DRPKLEP Y ERYS SL K L AD RK H Y M
DPRP2   1   ...........VATTGIPTADRGDAAATDDPAAR Q K HS DG RS THGSRK SG V
DPRP3   1   ............VNQ A VS H KC PSKTIKELGS SPPQRNW G AI LLVILV CS

DPP4    20  ITVPVV LN G   ATAD R T T TD... LK ..T RLKLYS R IS HEYL  N
DPRP1   61  AKA  D F VR N PDG HSDR  Y  MSGEN  EN L  SE PA  NRAA V M SW PLL
DPRP2   50  NKA  D F QK DL SG HGH  I  L MPYGS ENSL LYSE P V KE L L SW  ML
DPRP3   48   ITMSVI LSP.. LTNS ETRLS ED..L P D.. VLHD.PEA  IN TD V  S N

DPP4    75  . LVFNA YGNSS ...VFL NST DE HSIND S S DC  LLE YVKQ  HSY
DPRP1   121 . F Q TL DY  SR EL I R RI VG ASYD HQG.S T FQ GSG Y VK GGP
DPRP2   110 . H  TPHH V SH EL R R RL V C SY HSE.S   FQ S S   CR GGK
DPRP3   101 GH IKLN  TNAT ....L LENTT VT ..K SRHS V DLK LL A VKQI  YS

DPP4    130  SY D NK...R  I EERI NNTQWVTWSPVGHK LA  NND  KIEPNLPSY R
DPRP1   179 QG TQQP  P ...NLV E SCPNI   DF L P AL PDW A HS ND W S    R E RR  T
DPRP2   168 NG   S  K ...L K QCSG    DF IC AL PA FS  N S DLW AM E GE RRLT
DPRP3   155  S V YN I TREVW I N PEVEDSV QYAAWGVQGQQ I   N  YQPD KSSSL

DPP4    187  G..... S D I YN ITDWVY E V SA S L  S NGTE A Y......A...Q NDTEVP
DPRP1   235 YVH E AN  EDARS G AT VLQ  FDRYSG W  K  TTP  G I L   EEN ES
DPRP2   224  CH G  S VL DPKS G AT VIQ    RE G  W C TAS  GSE  L TLRIL EE V ES
DPRP3   215 S G..... K I  FN IADWLY E LLHSHIA   S D  R  F........ L IND SLVP

DPP4    235 L  YSFY DES  QYPK VRVP  D A  AVN ..TVK F V N DSLSSVTNATSI I TA  S
DPRP1   294  V I V TS M  T  ADS  RY P T  AN AV  F  M SEIMIL AE   DVIDK  L  E
DPRP2   284  V W  V PS AL  ERK DS  R   ETGSKN X AL K AE      V S QE  L  PF
DPRP3   263 T V  PR  GA YP.. GKQ P  PK  Q N ..T K YV LYG.....P HTL  MP D

DPP4    293 M IG.DH  CDVT A Q. ERIS Q W RR  Q ............................
DPRP1   354 I  EG V YT RA W  PE KYA S LL D S TRLK  V  SP EL  VE DVME QRLIES
DPRP2   344 S  PKV Y A A  V RD KYA V A  D R   W Q V L P A  F P STENEEQ LASARA
DPRP3   314 FKSR.EY  TMVK  VS N.TKTV R  N   ..............................

DPP4    322 .YS    D  EL SSGR NC VARQ  EMS T WVGRFRPSE HFTLDGNSF K  I NE..
DPRP1   414  D   T   II  EE TDI  N  HDI  HV PQS .HEEE  EL FAS CK  GFR L YK T    E
DPRP2   404  RN  Q  YVV   L V N   N HID  YP PQS  G EDF CF RAN CK GFC L K  T V L S
DPRP3   343 .I  T V  ETTTG.......ACSK YEMT S TWLSQQNE.E VFSRDGSK FMTVP KQG
```

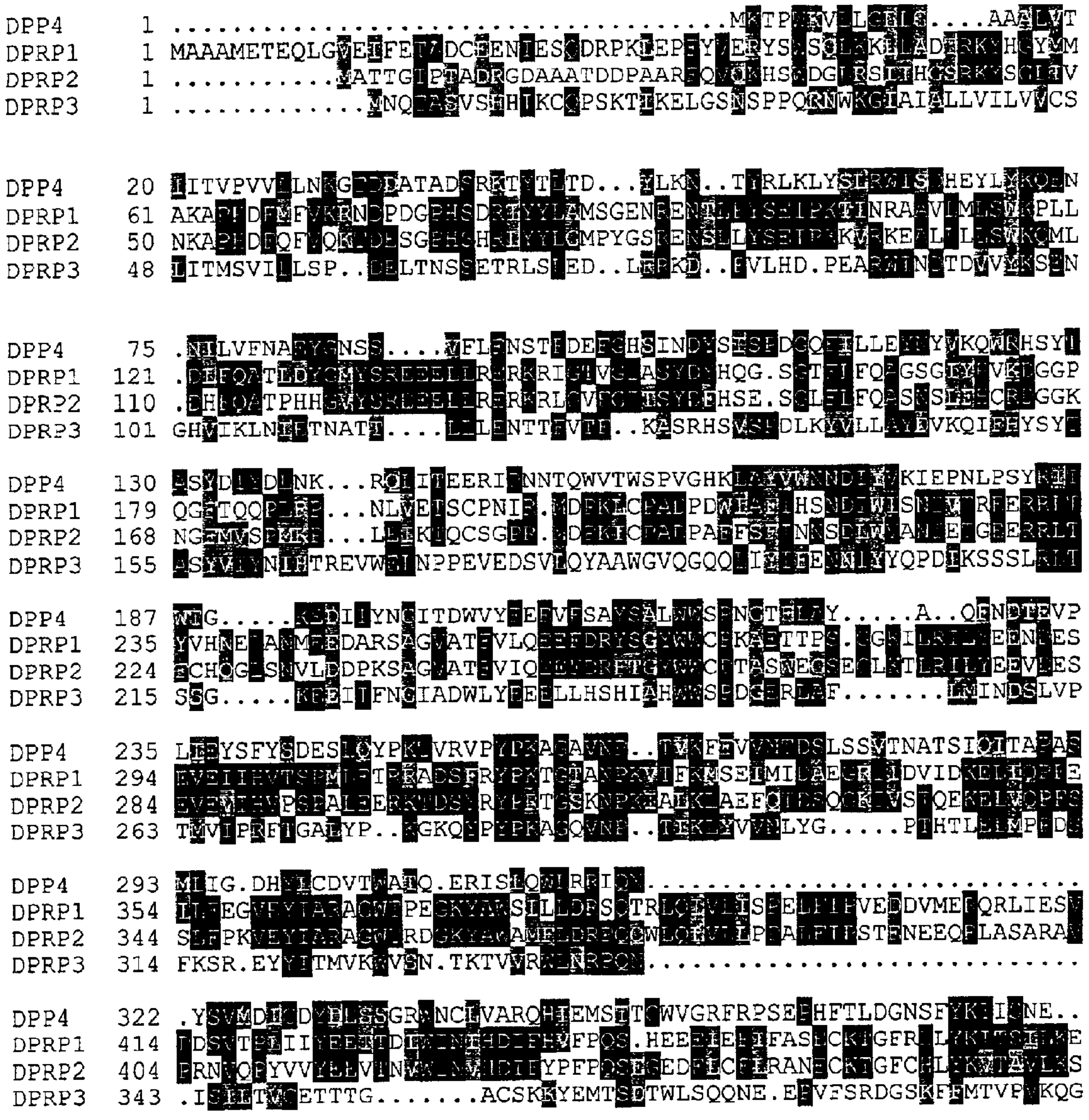

FIG. 1A

```
DPP4   379  E........ YRI CY QIDK .... CTF  KGT EV     E  TS YLYYIS EY
DPRP1  473  S  KR  S  L APS   CP I  ....  IA  SGEW VG RHGSN  QVD VR  V  ES
DPRP2  464  QG DW EPFS GED    C  I  ... F I  TSGEW VL RHGSK  W  E K V  Q  
DPRP3  394  G       E H  AM LIQS SEQITVRH  SG N EV K ....   Y     QK    LS E

DPP4   424  GM GG N  K QLSDYTKV CI S ELNPER  YSV F KEE K Y LR S  G    T  H
DPRP1  529       H  V SN VNPGEV RL DR  SHS  CI S HCD    KY S QKN  H VS  K  S
DPRP2  520         H  YVVST AA  IVR  TP  SHS  S S  FDM VS    SMST    HM KL S
DPRP3  445  S  RG Q  SA T  LLNRQC  S  NFMKEQ   FDA    P NQHFL  E   R  VS H

DPP4   484  SSVN KGLRVL DNSA DKMLQN..VQ M SKKLD   I  NETK   YQ IL PHFDKS KKY
DPRP1  588    DD  TC  K   WA   DS GPL D T P  ES ES T GE L  M  KP   L  P  KY
DPRP2  579  GP DD LH  OPR WASM  EA  SCP  DV  P   T  H RS VR LYG M KP AL  GK H
DPRP3  505  S  NPAKYF   SNSM K  ILKKKIGK .. EI I H D YE  PLQ SL  K FMDRNQ A

DPP4   542  L  DV    CS KA TV  R .. LN ATYLAS ENI  ASF  GRGSG   QGD IMH A N  
DPRP1  648  T LF YC  Q    NN F KG K  ERL  TLAS G  V  IL NRG CHRG    FC A  YKM
DPRP2  639  T LEV GGP VQ  AN   KG  KY LRL TLAS G A V   IDCRGS CQRGL RF GA  NQ  
DPRP3  563  L  I DEE  GG  VTDKE  .. ID DSVL DMDNV  ARF GRGS G QG   ILQE  RR

DPP4   600  T         ARQ S . MG  VI NKR A WG SYGG   S V G G G  C  A V   SR
DPRP1  708          QV    M   SRYDF IDI DP G HGWSYGG I L A  MQRSD   V  A AP VT
DPRP2  699  QV       Q    V  EKY   I  SRVA  GW YGG  LS L G  HK PQ  V  A   PW V
DPRP3  621  S EVK    TAVK  L .  LPY   SKR S  F KG  TAS  I  KSDEK L   C SVV     D

DPP4   659        V     R         TPE D LDH RNST   MSRAENFKQVEY   HG TA     VH     Q  Q
DPRP1  768            T  V    R  MCH  DCN  QG YL SSVA QAE   SE  NR L    GFLD   VH    SI
DPRP2  759  MA    T  T  R  D   ENN HG  EA SV  HV   LPNE NRL  I HGFLD   VH        NF
DPRP3  680  LKL   AS     V CM  SKEE S .. T  Q AS   HNVHGLKEEN         TA  TK V  Q SA

DPP4   719   SKA DV  VDE AMW  T   D G  ASST H   IYTH S     K   FSLP ............
DPRP1  828     SF  V  CKP   DL I   Q  RHS   PES      LH      LQ N  GSR  AA  KVI .....
DPRP2  819  L SQ    CKP  QL I   F RHS   PES GEH EVT  LH  LQ Y  ..................
DPRP3  738    KH    KA VN  TM    PD  G NVSEK . KY  LYST   K  FS DC KEE  SV  PQEPEEDE
```

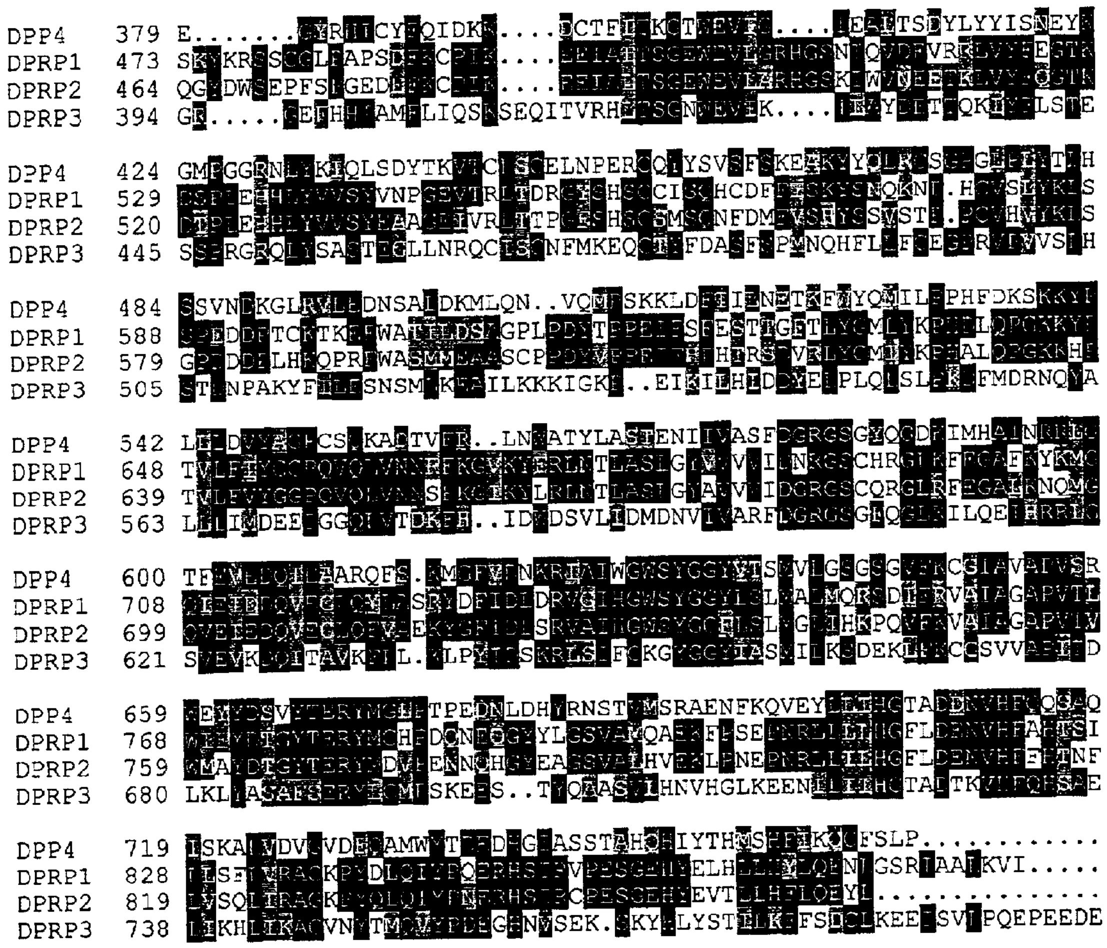

FIG. 1B

```
hDPRP1    1    VAAAMETEQLGVEIFETADCLEN.I.SQDRPKLEPFYVERYSESQLKKLLADTRKYHGYN
mDPRP1    1    VAAAMETEQLGVEIFETAECEEGVGFSQDRPKLEPFYVERYSWSQLKKLLADTRKYHGYN

hDPRP1    60   MAKAPHDEMFVKRNDFLGPHSDREYYLAMSGENREKTLFYSEIPKTINRAAVLMLSWKPI
mDPRP1    61   MAKAPHDFMFVKTDFLRPHSDRVYYLAMSGENRENTLFYSEIPKTINRAAVLMLSWKPI

hDPRP1    120  LDLFQATLDYGMYSREEELLREPKRIGTVGIASYDYLQSSGTELFQACSGIYEWKDGGPQ
mDPRP1    121  LDLFQATLDYGMYSREEDLLRQRKRIGTVGTAADYHPSSGTFLFQAGSGIYEKIKGSLH

hDPRP1    180  GFTQQPLREHLVEPSCPMIRMDPKLCPAIPDWIAFIHSNDIWISMEVTREERRLTYVHNE
mDPRP1    181  GFTQQPLREMLVEPSCPMIRMDPKLCPADPDWIAFIHSNDIWISMEVTREERRLTYVHNF

hDPRP1    240  LANMEELARSAGVATEVLQEEPDRYSGYWQPKELTTPSGGKTLRILYDENDESEVEITH
mDPRP1    241  LANMEELPPSAGVATEVLQEEPDRYGGVWQGCAFRTPSGGKTLPILYEENDESEVEIIH

hDPRP1    300  VTSPMLETRRADGFRYPKTGTANEKVTEKMSEIMEDAEGRIIDVIDKEITQPFEILEGV
mDPRP1    301  VTSPMLETRRADSFRYFKTGTANPKVTEKMSEIVVDEAGGIIDVIDKELVQEFELLEGV

hDPRP1    360  EYIARAGWTPEGKYAWSILLDRSQTRLQIVLISPELFIPVEDLVEEQRLIESVPDSVTE
mDPRP1    361  EYIARAGWTPEGKHAWSILLDRSQHLQIVLISPLIIPVEDLAERQRLIESVPDSVTE

hDPRP1    420  LIIYEETTDIWINIEDIFHVFPQSHAEELFIFASECKTGFRHLYKITSILKESKYKRSS
mDPRP1    421  LIIYEETTDIWINIHLFPHVFPQEHFDEFPTFASECKTGFRHLYKITSILKESKYKRSS

hDPRP1    480  GGLPAPSDFKCPIKEFIALTSGEWEVLGREQSNTQVDEVRELVYEEGTKDSPLEHHLVWV
mDPRP1    481  GGIPAPSDFKCPIKEEITLTSGEWEVLGNHQSNIWVDFARKLVYFEGTKDSPLEHHLVWT

hDPRP1    540  SYVIPGEVTRLTDPGYSHSCCESQHCDITFSKYSMQKNPHCVSLYKISSFEDDTCKFK
mDPRP1    541  SYANPGEVVRLTDRGYSHSCCESRHCLFTISKYSNQKNPHCVSLYKLSSFEDDVHKTKE

hDPRP1    600  FWATILDSADPIPDYTPPEIFSFESPTGFTLYGMLYKFHDLQEGKKYFTVLFTYGGPQVC
mDPRP1    601  FWATILDSACPLPDYTPPEIFSFESTTGFTLYGMLYKFHDLQPCKKYFTVLFTYGGPQVC

hDPRP1    660  LVNNRFKGVKYFRIATLASLGYVWVVIDNRCSHRGLKFEGAFKYKMGQIEIDLQVEGLQ
mDPRP1    661  LVNNRFKGVKYFRINTLASLGYVWVVIDNRGSCHRGLKIEGAFKYKMGQIEIDDQVEGLC

hDPRP1    720  YLASRYDFIDLDRVGTHGWSYGGYLSLMALMQRSDIFRVAIAGAPVTLMIFYDTGYTERY
mDPRP1    721  YLASQYDFIDLDRVGTHGWSYGGYLSLMAIMQRSDIFRVAIAGAPVTLMIFYDTGYTEKY

hDPRP1    780  VCHFDQNEQGYYLESVAMQATKFPSEPNRLLLHGFLDENVHFAHTSILLSFLVRAGKPY
mDPRP1    781  VGHFDQNEQGGYYLCSVAMQAEKFPSEPNRLLLHGFLDENVHFAHTSILSPLVRAGKPY

hDPRP1    840  DLQIYPQERHSIRVPESGEHYELHLLHYLQENLGSRIAAIKVI
mDPRP1    841  DLQIYPQERHSIRVPESGEHYELHLLYLQFALGSRIAALKVI
```

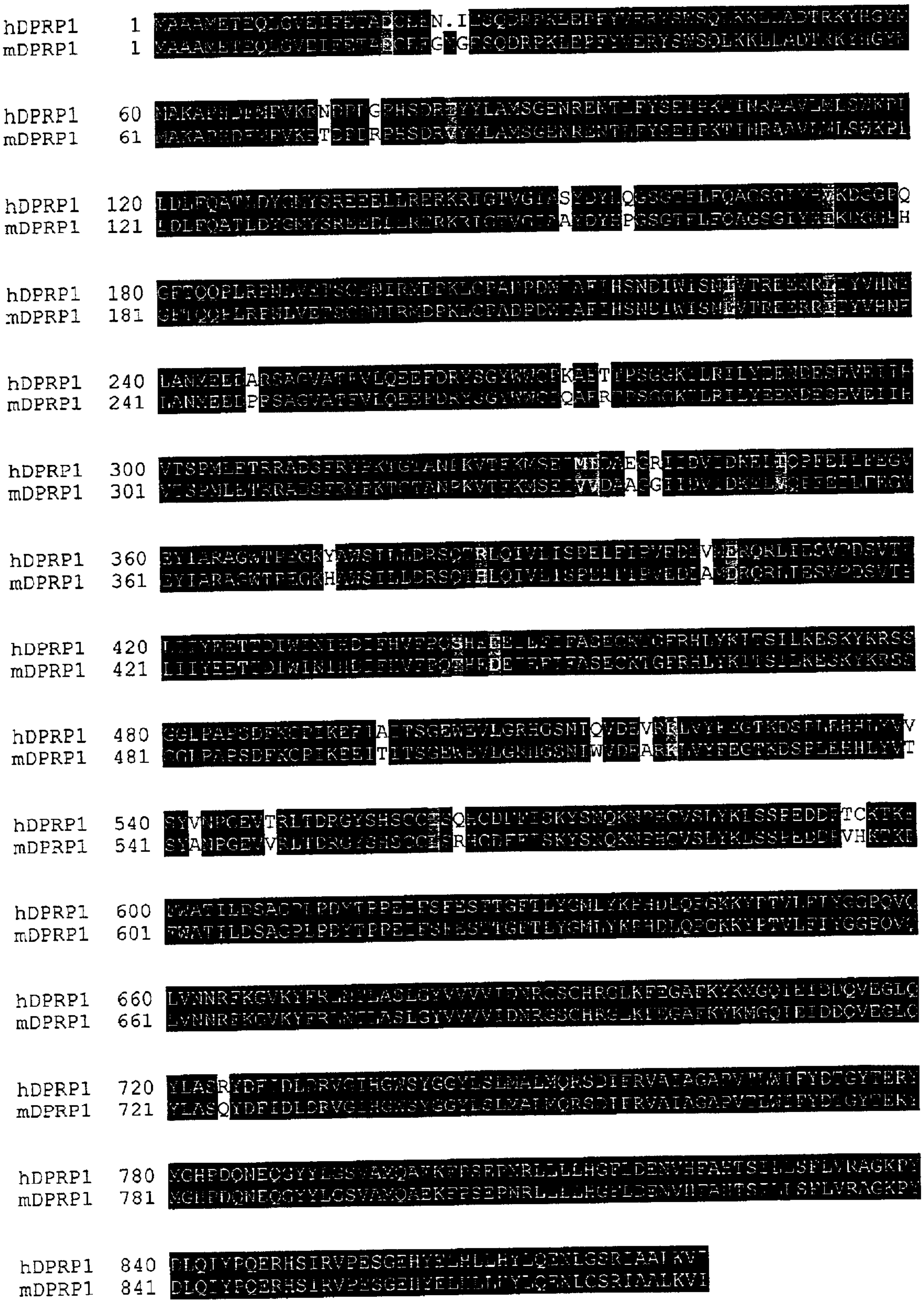

FIG. 2

SEQUENCE LISTING

```
<160> NUMBER OF SEQ ID NOS: 61

<210> SEQ ID NO 1
<211> LENGTH: 882
<212> TYPE: PRT
<213> ORGANISM: Homo sapiens

<400> SEQUENCE: 1

Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Glu Asn Arg Glu Asn Thr
                85                  90                  95

Leu Phe Tyr Ser Glu Ile Pro Lys Thr Ile Asn Arg Ala Ala Val Leu
            100                 105                 110

Met Leu Ser Trp Lys Pro Leu Leu Asp Leu Phe Gln Ala Thr Leu Asp
        115                 120                 125

Tyr Gly Met Tyr Ser Arg Glu Glu Glu Leu Leu Arg Glu Arg Lys Arg
    130                 135                 140

Ile Gly Thr Val Gly Ile Ala Ser Tyr Asp Tyr His Gln Gly Ser Gly
145                 150                 155                 160

Thr Phe Leu Phe Gln Ala Gly Ser Gly Ile Tyr His Val Lys Asp Gly
                165                 170                 175

Gly Pro Gln Gly Phe Thr Gln Gln Pro Leu Arg Pro Asn Leu Val Glu
            180                 185                 190

Thr Ser Cys Pro Asn Ile Arg Met Asp Pro Lys Leu Cys Pro Ala Asp
        195                 200                 205

Pro Asp Trp Ile Ala Phe Ile His Ser Asn Asp Ile Trp Ile Ser Asn
    210                 215                 220

Ile Val Thr Arg Glu Glu Arg Arg Leu Thr Tyr Val His Asn Glu Leu
225                 230                 235                 240
```

-continued

```
Ala Asn Met Glu Glu Asp Ala Arg Ser Ala Gly Val Ala Thr Phe Val
                245                 250                 255

Leu Gln Glu Glu Phe Asp Arg Tyr Ser Gly Tyr Trp Trp Cys Pro Lys
            260                 265                 270

Ala Glu Thr Thr Pro Ser Gly Gly Lys Ile Leu Arg Ile Leu Tyr Glu
        275                 280                 285

Glu Asn Asp Glu Ser Glu Val Glu Ile Ile His Val Thr Ser Pro Met
    290                 295                 300

Leu Glu Thr Arg Arg Ala Asp Ser Phe Arg Tyr Pro Lys Thr Gly Thr
305                 310                 315                 320

Ala Asn Pro Lys Val Thr Phe Lys Met Ser Glu Ile Met Ile Asp Ala
                325                 330                 335

Glu Gly Arg Ile Ile Asp Val Ile Asp Lys Glu Leu Ile Gln Pro Phe
            340                 345                 350

Glu Ile Leu Phe Glu Gly Val Glu Tyr Ile Ala Arg Ala Gly Trp Thr
        355                 360                 365

Pro Glu Gly Lys Tyr Ala Trp Ser Ile Leu Leu Asp Arg Ser Gln Thr
    370                 375                 380

Arg Leu Gln Ile Val Leu Ile Ser Pro Glu Leu Phe Ile Pro Val Glu
385                 390                 395                 400

Asp Asp Val Met Glu Arg Gln Arg Leu Ile Glu Ser Val Pro Asp Ser
                405                 410                 415

Val Thr Pro Leu Ile Ile Tyr Glu Glu Thr Thr Asp Ile Trp Ile Asn
            420                 425                 430

Ile His Asp Ile Phe His Val Phe Pro Gln Ser His Glu Glu Glu Ile
        435                 440                 445

Glu Phe Ile Phe Ala Ser Glu Cys Lys Thr Gly Phe Arg His Leu Tyr
    450                 455                 460

Lys Ile Thr Ser Ile Leu Lys Glu Ser Lys Tyr Lys Arg Ser Ser Gly
465                 470                 475                 480

Gly Leu Pro Ala Pro Ser Asp Phe Lys Cys Pro Ile Lys Glu Glu Ile
                485                 490                 495

Ala Ile Thr Ser Gly Glu Trp Glu Val Leu Gly Arg His Gly Ser Asn
            500                 505                 510

Ile Gln Val Asp Glu Val Arg Arg Leu Val Tyr Phe Glu Gly Thr Lys
        515                 520                 525

Asp Ser Pro Leu Glu His His Leu Tyr Val Val Ser Tyr Val Asn Pro
    530                 535                 540

Gly Glu Val Thr Arg Leu Thr Asp Arg Gly Tyr Ser His Ser Cys Cys
545                 550                 555                 560

Ile Ser Gln His Cys Asp Phe Phe Ile Ser Lys Tyr Ser Asn Gln Lys
                565                 570                 575

Asn Pro His Cys Val Ser Leu Tyr Lys Leu Ser Ser Pro Glu Asp Asp
            580                 585                 590

Pro Thr Cys Lys Thr Lys Glu Phe Trp Ala Thr Ile Leu Asp Ser Ala
        595                 600                 605

Gly Pro Leu Pro Asp Tyr Thr Pro Pro Glu Ile Phe Ser Phe Glu Ser
    610                 615                 620

Thr Thr Gly Phe Thr Leu Tyr Gly Met Leu Tyr Lys Pro His Asp Leu
625                 630                 635                 640

Gln Pro Gly Lys Lys Tyr Pro Thr Val Leu Phe Ile Tyr Gly Gly Pro
                645                 650                 655

Gln Val Gln Leu Val Asn Asn Arg Phe Lys Gly Val Lys Tyr Phe Arg
```

-continued

```
            660                 665                 670

Leu Asn Thr Leu Ala Ser Leu Gly Tyr Val Val Val Val Ile Asp Asn
        675                 680                 685

Arg Gly Ser Cys His Arg Gly Leu Lys Phe Glu Gly Ala Phe Lys Tyr
    690                 695                 700

Lys Met Gly Gln Ile Glu Ile Asp Asp Gln Val Glu Gly Leu Gln Tyr
705                 710                 715                 720

Leu Ala Ser Arg Tyr Asp Phe Ile Asp Leu Asp Arg Val Gly Ile His
                725                 730                 735

Gly Trp Ser Tyr Gly Gly Tyr Leu Ser Leu Met Ala Leu Met Gln Arg
            740                 745                 750

Ser Asp Ile Phe Arg Val Ala Ile Ala Gly Ala Pro Val Thr Leu Trp
        755                 760                 765

Ile Phe Tyr Asp Thr Gly Tyr Thr Glu Arg Tyr Met Gly His Pro Asp
    770                 775                 780

Gln Asn Glu Gln Gly Tyr Tyr Leu Gly Ser Val Ala Met Gln Ala Glu
785                 790                 795                 800

Lys Phe Pro Ser Glu Pro Asn Arg Leu Leu Leu Leu His Gly Phe Leu
                805                 810                 815

Asp Glu Asn Val His Phe Ala His Thr Ser Ile Leu Leu Ser Phe Leu
            820                 825                 830

Val Arg Ala Gly Lys Pro Tyr Asp Leu Gln Ile Tyr Pro Gln Glu Arg
        835                 840                 845

His Ser Ile Arg Val Pro Glu Ser Gly Glu His Tyr Glu Leu His Leu
    850                 855                 860

Leu His Tyr Leu Gln Glu Asn Leu Gly Ser Arg Ile Ala Ala Leu Lys
865                 870                 875                 880

Val Ile
```

<210> SEQ ID NO 2
<211> LENGTH: 2671
<212> TYPE: DNA
<213> ORGANISM: Homo sapiens

<400> SEQUENCE: 2

```
cggtaccatg gcagcagcaa tggaaacaga acagctgggt gttgagatat ttgaaactgc     60

ggactgtgag gagaatattg aatcacagga tcggcctaaa ttggagcctt tttatgttga    120

gcggtattcc tggagtcagc ttaaaaagct gcttgccgat accagaaaat atcatggcta    180

catgatggct aaggcaccac atgatttcat gtttgtgaag aggaatgatc cagatggacc    240

tcattcagac agaatctatt accttgccat gtctggtgag aacagagaaa atacactgtt    300

ttattctgaa attcccaaaa ctatcaatag agcagcagtc ttaatgctct cttggaagcc    360

tcttttggat ctttttcagg caacactgga ctatggaatg tattctcgag aagaagaact    420

attaagagaa agaaaacgca ttggaacagt cggaattgct tcttacgatt atcaccaagg    480

aagtggaaca tttctgtttc aagccggtag tggaatttat cacgtaaaag atggagggcc    540

acaaggattt acgcaacaac ctttaaggcc caatctagtg gaaactagtt gtcccaacat    600

acggatggat ccaaaattat gccctgctga tccagactgg attgctttta tacatagcaa    660

cgatatttgg atatctaaca tcgtaaccag agaagaaagg agactcactt atgtgcacaa    720

tgagctagcc aacatggaag aagatgccag atcagctgga gtcgctacct ttgttctcca    780

agaagaattt gatagatatt ctggctattg gtggtgtcca aaagctgaaa caactcccag    840
```

-continued

```
tggtggtaaa attcttagaa ttctatatga agaaaatgat gaatctgagg tggaaattat    900
tcatgttaca tcccctatgt tggaaacaag gagggcagat tcattccgtt atcctaaaac    960
aggtacagca aatcctaaag tcacttttaa gatgtcagaa ataatgattg atgctgaagg   1020
aaggatcata gatgtcatag ataaggaact aattcaacct tttgagattc tatttgaagg   1080
agttgaatat attgccagag ctggatggac tcctgaggga aaatatgctt ggtccatcct   1140
actagatcgc tcccagactc gcctgcagat agtgttgatc tcacctgaat tatttatccc   1200
agtagaagat gatgttatgg aaaggcagag actcattgag tcagtgcctg attctgtgac   1260
gccactaatt atctatgaag aaacaacaga catctggata aatatccatg acatctttca   1320
tgtttttccc caaagtcacg aagaggaaat tgagtttatt tttgcctctg aatgcaaaac   1380
aggtttccgt catttataca aaattacatc tattttaaag gaaagcaaat ataaacgatc   1440
cagtggtggg ctgcctgctc caagtgattt caagtgtcct atcaaagagg agatagcaat   1500
taccagtggt gaatgggaag ttcttggccg gcatggatct aatatccaag ttgatgaagt   1560
cagaaggctg gtatattttg aaggcaccaa agactcccct ttagagcatc acctgtacgt   1620
agtcagttac gtaaatcctg gagaggtgac aaggctgact gaccgtggct actcacattc   1680
ttgctgcatc agtcagcact gtgacttctt tataagtaag tatagtaacc agaagaatcc   1740
acactgtgtg tccctttaca agctatcaag tcctgaagat gacccaactt gcaaaacaaa   1800
ggaattttgg gccaccattt tggattcagc aggtcctctt cctgactata ctcctccaga   1860
aattttctct tttgaaagta ctactggatt tacattgtat gggatgctct acaagcctca   1920
tgatctacag cctggaaaga aatatcctac tgtgctgttc atatatggtg gtcctcaggt   1980
gcagttggtg aataatcgat ttaaaggagt caagtatttc cgcttgaata ccctagcctc   2040
tctaggttat gtggttgtag tgatagacaa caggggatcc tgtcaccgag ggcttaaatt   2100
tgaaggcgcc tttaaatata aaatgggtca aatagaaatt gacgatcagg tggaaggact   2160
ccaatatcta gcttctcgat atgatttcat tgacttagat cgtgtgggca tccacggctg   2220
gtcctatgga ggatacctct ccctgatggc attaatgcag aggtcagata tcttcagggt   2280
tgctattgct ggggccccag tcactctgtg gatcttctat gatacaggat acacggaacg   2340
ttatatgggt caccctgacc agaatgaaca gggctattac ttaggatctg tggccatgca   2400
agcagaaaag ttcccctctg aaccaaatcg tttactgctc ttacatggtt tcctggatga   2460
gaatgtccat tttgcacata ccagtatatt actgagtttt ttagtgaggg ctggaaagcc   2520
atatgattta cagatctatc ctcaggagag acacagcata agagttcctg aatcgggaga   2580
acattatgaa ctgcatcttt tgcactacct tcaagaaaac cttggatcac gtattgctgc   2640
tctaaaagtg atatgagcgg ccgcgagctc c                                  2671
```

<210> SEQ ID NO 3
<211> LENGTH: 863
<212> TYPE: PRT
<213> ORGANISM: Homo sapiens

<400> SEQUENCE: 3

```
Met Ala Thr Thr Gly Thr Pro Thr Ala Asp Arg Gly Asp Ala Ala Ala
1               5                   10                  15

Thr Asp Asp Pro Ala Ala Arg Phe Gln Val Gln Lys His Ser Trp Asp
            20                  25                  30

Gly Leu Arg Ser Ile Ile His Gly Ser Arg Lys Tyr Ser Gly Leu Ile
        35                  40                  45
```

-continued

```
Val Asn Lys Ala Pro His Asp Phe Gln Phe Val Gln Lys Thr Asp Glu
    50                  55                  60

Ser Gly Pro His Ser His Arg Leu Tyr Tyr Leu Gly Met Pro Tyr Gly
65                  70                  75                  80

Ser Arg Glu Asn Ser Leu Leu Tyr Ser Glu Ile Pro Lys Lys Val Arg
                85                  90                  95

Lys Glu Ala Leu Leu Leu Leu Ser Trp Lys Gln Met Leu Asp His Phe
            100                 105                 110

Gln Ala Thr Pro His His Gly Val Tyr Ser Arg Glu Glu Glu Leu Leu
        115                 120                 125

Arg Glu Arg Lys Arg Leu Gly Val Phe Gly Ile Thr Ser Tyr Asp Phe
    130                 135                 140

His Ser Glu Ser Gly Leu Phe Leu Phe Gln Ala Ser Asn Ser Leu Phe
145                 150                 155                 160

His Cys Arg Asp Gly Gly Lys Asn Gly Phe Met Val Ser Pro Met Lys
                165                 170                 175

Pro Leu Glu Ile Lys Thr Gln Cys Ser Gly Pro Arg Met Asp Pro Lys
            180                 185                 190

Ile Cys Pro Ala Asp Pro Ala Phe Phe Ser Phe Ile Asn Asn Ser Asp
        195                 200                 205

Leu Trp Val Ala Asn Ile Glu Thr Gly Glu Glu Arg Arg Leu Thr Phe
    210                 215                 220

Cys His Gln Gly Leu Ser Asn Val Leu Asp Asp Pro Lys Ser Ala Gly
225                 230                 235                 240

Val Ala Thr Phe Val Ile Gln Glu Glu Phe Asp Arg Phe Thr Gly Tyr
                245                 250                 255

Trp Trp Cys Pro Thr Ala Ser Trp Glu Gly Ser Glu Gly Leu Lys Thr
            260                 265                 270

Leu Arg Ile Leu Tyr Glu Glu Val Asp Glu Ser Glu Val Glu Val Ile
        275                 280                 285

His Val Pro Ser Pro Ala Leu Glu Glu Arg Lys Thr Asp Ser Tyr Arg
    290                 295                 300

Tyr Pro Arg Thr Gly Ser Lys Asn Pro Lys Ile Ala Leu Lys Leu Ala
305                 310                 315                 320

Glu Phe Gln Thr Asp Ser Gln Gly Lys Ile Val Ser Thr Gln Glu Lys
                325                 330                 335

Glu Leu Val Gln Pro Phe Ser Ser Leu Phe Pro Lys Val Glu Tyr Ile
            340                 345                 350

Ala Arg Ala Gly Trp Thr Arg Asp Gly Lys Tyr Ala Trp Ala Met Phe
        355                 360                 365

Leu Asp Arg Pro Gln Gln Trp Leu Gln Leu Val Leu Leu Pro Pro Ala
    370                 375                 380

Leu Phe Ile Pro Ser Thr Glu Asn Glu Glu Gln Arg Leu Ala Ser Ala
385                 390                 395                 400

Arg Ala Val Pro Arg Asn Val Gln Pro Tyr Val Val Tyr Glu Glu Val
                405                 410                 415

Thr Asn Val Trp Ile Asn Val His Asp Ile Phe Tyr Pro Phe Pro Gln
            420                 425                 430

Ser Glu Gly Glu Asp Glu Leu Cys Phe Leu Arg Ala Asn Glu Cys Lys
        435                 440                 445

Thr Gly Phe Cys His Leu Tyr Lys Val Thr Ala Val Leu Lys Ser Gln
    450                 455                 460

Gly Tyr Asp Trp Ser Glu Pro Phe Ser Pro Gly Glu Asp Glu Phe Lys
```

-continued

```
465                 470                 475                 480

Cys Pro Ile Lys Glu Glu Ile Ala Leu Thr Ser Gly Glu Trp Glu Val
                485                 490                 495

Leu Ala Arg His Gly Ser Lys Ile Trp Val Asn Glu Glu Thr Lys Leu
            500                 505                 510

Val Tyr Phe Gln Gly Thr Lys Asp Thr Pro Leu Glu His His Leu Tyr
        515                 520                 525

Val Val Ser Tyr Glu Ala Ala Gly Glu Ile Val Arg Leu Thr Thr Pro
    530                 535                 540

Gly Phe Ser His Ser Cys Ser Met Ser Gln Asn Phe Asp Met Phe Val
545                 550                 555                 560

Ser His Tyr Ser Ser Val Ser Thr Pro Pro Cys Val His Val Tyr Lys
                565                 570                 575

Leu Ser Gly Pro Asp Asp Asp Pro Leu His Lys Gln Pro Arg Phe Trp
            580                 585                 590

Ala Ser Met Met Glu Ala Ala Ser Cys Pro Pro Asp Tyr Val Pro Pro
        595                 600                 605

Glu Ile Phe His Phe His Thr Arg Ser Asp Val Arg Leu Tyr Gly Met
    610                 615                 620

Ile Tyr Lys Pro His Ala Leu Gln Pro Gly Lys Lys His Pro Thr Val
625                 630                 635                 640

Leu Phe Val Tyr Gly Gly Pro Gln Val Gln Leu Val Asn Asn Ser Phe
                645                 650                 655

Lys Gly Ile Lys Tyr Leu Arg Leu Asn Thr Leu Ala Ser Leu Gly Tyr
            660                 665                 670

Ala Val Val Val Ile Asp Gly Arg Gly Ser Cys Gln Arg Gly Leu Arg
        675                 680                 685

Phe Glu Gly Ala Leu Lys Asn Gln Met Gly Gln Val Glu Ile Glu Asp
    690                 695                 700

Gln Val Glu Gly Leu Gln Phe Val Ala Glu Lys Tyr Gly Phe Ile Asp
705                 710                 715                 720

Leu Ser Arg Val Ala Ile His Gly Trp Ser Tyr Gly Gly Phe Leu Ser
                725                 730                 735

Leu Met Gly Leu Ile His Lys Pro Gln Val Phe Lys Val Ala Ile Ala
            740                 745                 750

Gly Ala Pro Val Thr Val Trp Met Ala Tyr Asp Thr Gly Tyr Thr Glu
        755                 760                 765

Arg Tyr Met Asp Val Pro Glu Asn Asn Gln His Gly Tyr Glu Ala Gly
    770                 775                 780

Ser Val Ala Leu His Val Glu Lys Leu Pro Asn Glu Pro Asn Arg Leu
785                 790                 795                 800

Leu Ile Leu His Gly Phe Leu Asp Glu Asn Val His Phe Phe His Thr
                805                 810                 815

Asn Phe Leu Val Ser Gln Leu Ile Arg Ala Gly Lys Pro Tyr Gln Leu
            820                 825                 830

Gln Ile Tyr Pro Asn Glu Arg His Ser Ile Arg Cys Pro Glu Ser Gly
        835                 840                 845

Glu His Tyr Glu Val Thr Leu Leu His Phe Leu Gln Glu Tyr Leu
    850                 855                 860
```

<210> SEQ ID NO 4
<211> LENGTH: 2617
<212> TYPE: DNA
<213> ORGANISM: Homo sapiens -continued

<400> SEQUENCE: 4

```
caagcttacc atggccacca ccgggacccc aacggccgac cgaggcgacg cagccgccac     60
agatgacccg gccgcccgct tccaggtgca gaagcactcg tgggacgggc tccggagcat    120
catccacggc agccgcaagt actcgggcct cattgtcaac aaggcgcccc acgacttcca    180
gtttgtgcag aagacggatg agtctgggcc ccactcccac cgcctctact acctgggaat    240
gccatatggc agccgagaga actccctcct ctactctgag attcccaaga aggtccggaa    300
agaggctctg ctgctcctgt cctggaagca gatgctggat catttccagg ccacgcccca    360
ccatggggtc tactctcggg aggaggagct gctgagggag cggaaacgcc tgggggtctt    420
cggcatcacc tcctacgact tccacagcga gagtggcctc ttcctcttcc aggccagcaa    480
cagcctcttc cactgtcgcg acggcggcaa gaacggcttc atggtgtccc ctatgaaacc    540
gctggaaatc aagacccagt gctcagggcc ccggatggac cccaaaatct gccctgccga    600
ccctgccttc ttctccttca tcaataacag cgacctgtgg gtggccaaca tcgagacagg    660
cgaggagcgg cggctgacct tctgccacca aggtttatcc aatgtcctgg atgaccccaa    720
gtctgcgggt gtggccacct tcgtcataca ggaagagttc gaccgcttca ctgggtactg    780
gtggtgcccc acagcctcct gggaaggttc agagggcctc aagacgctgc gaatcctgta    840
tgaggaagtc gatgagtccg aggtggaggt cattcacgtc ccctctcctg cgctagaaga    900
aaggaagacg gactcgtatc ggtaccccag gacaggcagc aagaatccca agattgcctt    960
gaaactggct gagttccaga ctgacagcca gggcaagatc gtctcgaccc aggagaagga   1020
gctggtgcag cccttcagct cgctgttccc gaaggtggag tacatcgcca gggccgggtg   1080
gacccgggat ggcaaatacg cctgggccat gttcctggac cggccccagc agtggctcca   1140
gctcgtcctc ctcccccccgg ccctgttcat cccgagcaca gagaatgagg agcagcggct   1200
agcctctgcc agagctgtcc ccaggaatgt ccagccgtat gtggtgtacg aggaggtcac   1260
caacgtctgg atcaatgttc atgacatctt ctatcccttc cccaatcag agggagagga   1320
cgagctctgc tttctccgcg ccaatgaatg caagaccggc ttctgccatt tgtacaaagt   1380
caccgccgtt ttaaaatccc agggctacga ttggagtgag cccttcagcc ccggggaaga   1440
tgaatttaag tgccccatta aggaagagat tgctctgacc agcggtgaat gggaggtttt   1500
ggcgaggcac ggctccaaga tctgggtcaa tgaggagacc aagctggtgt acttccaggg   1560
caccaaggac acgccgctgg agcaccacct ctacgtggtc agctatgagg cggccggcga   1620
gatcgtacgc ctcaccacgc ccggcttctc ccatagctgc tccatgagcc agaacttcga   1680
catgttcgtc agccactaca gcagcgtgag cacgccgccc tgcgtgcacg tctacaagct   1740
gagcggcccc gacgacgacc ccctgcacaa gcagccccgc ttctgggcta gcatgatgga   1800
ggcagccagc tgcccccccgg attatgttcc tccagagatc ttccatttcc acacgcgctc   1860
ggatgtgcgg ctctacggca tgatctacaa gccccacgcc ttgcagccag ggaagaagca   1920
ccccaccgtc ctctttgtat atggaggccc ccaggtgcag ctggtgaata actccttcaa   1980
aggcatcaag tacttgcggc tcaacacact ggcctccctg ggctacgccg tggttgtgat   2040
tgacggcagg ggctcctgtc agcgagggct tcggttcgaa ggggccctga aaaaccaaat   2100
gggccaggtg gagatcgagg accaggtgga gggcctgcag ttcgtggccg agaagtatgg   2160
cttcatcgac ctgagccgag ttgccatcca tggctggtcc tacgggggct tcctctcgct   2220
catggggcta atccacaagc cccaggtgtt caaggtggcc atcgcgggtg ccccggtcac   2280
```

-continued

```
cgtctggatg gcctacgaca cagggtacac tgagcgctac atggacgtcc ctgagaacaa   2340

ccagcacggc tatgaggcgg gttccgtggc cctgcacgtg gagaagctgc ccaatgagcc   2400

caaccgcttg cttatcctcc acggcttcct ggacgaaaac gtgcactttt tccacacaaa   2460

cttcctcgtc tcccaactga tccgagcagg gaaaccttac cagctccaga tctaccccaa   2520

cgagagacac agtattcgct gccccgagtc gggcgagcac tatgaagtca cgttgctgca   2580

ctttctacag gaatacctct gagcggccgc ggatccg                            2617
```

<210> SEQ ID NO 5
<211> LENGTH: 796
<212> TYPE: PRT
<213> ORGANISM: Homo sapiens

<400> SEQUENCE: 5

```
Met Asn Gln Thr Ala Ser Val Ser His His Ile Lys Cys Gln Pro Ser
1               5                   10                  15

Lys Thr Ile Lys Glu Leu Gly Ser Asn Ser Pro Pro Gln Arg Asn Trp
            20                  25                  30

Lys Gly Ile Ala Ile Ala Leu Leu Val Ile Leu Val Val Cys Ser Leu
        35                  40                  45

Ile Thr Met Ser Val Ile Leu Leu Ser Pro Asp Glu Leu Thr Asn Ser
    50                  55                  60

Ser Glu Thr Arg Leu Ser Leu Glu Asp Leu Phe Arg Lys Asp Phe Val
65                  70                  75                  80

Leu His Asp Pro Glu Ala Arg Trp Ile Asn Asp Thr Asp Val Val Tyr
                85                  90                  95

Lys Ser Glu Asn Gly His Val Ile Lys Leu Asn Ile Glu Thr Asn Ala
            100                 105                 110

Thr Thr Leu Leu Leu Glu Asn Thr Thr Phe Val Thr Phe Lys Ala Ser
        115                 120                 125

Arg His Ser Val Ser Pro Asp Leu Lys Tyr Val Leu Leu Ala Tyr Asp
    130                 135                 140

Val Lys Gln Ile Phe His Tyr Ser Tyr Thr Ala Ser Tyr Val Ile Tyr
145                 150                 155                 160

Asn Ile His Thr Arg Glu Val Trp Glu Leu Asn Pro Pro Glu Val Glu
                165                 170                 175

Asp Ser Val Leu Gln Tyr Ala Ala Trp Gly Val Gln Gly Gln Gln Leu
            180                 185                 190

Ile Tyr Ile Phe Glu Asn Asn Ile Tyr Tyr Gln Pro Asp Ile Lys Ser
        195                 200                 205

Ser Ser Leu Arg Leu Thr Ser Ser Gly Lys Glu Glu Ile Ile Phe Asn
    210                 215                 220

Gly Ile Ala Asp Trp Leu Tyr Glu Glu Glu Leu Leu His Ser His Ile
225                 230                 235                 240

Ala His Trp Trp Ser Pro Asp Gly Glu Arg Leu Ala Phe Leu Met Ile
                245                 250                 255

Asn Asp Ser Leu Val Pro Thr Met Val Ile Pro Arg Phe Thr Gly Ala
            260                 265                 270

Leu Tyr Pro Lys Gly Lys Gln Tyr Pro Tyr Pro Lys Ala Gly Gln Val
        275                 280                 285

Asn Pro Thr Ile Lys Leu Tyr Val Val Asn Leu Tyr Gly Pro Thr His
    290                 295                 300

Thr Leu Glu Leu Met Pro Pro Asp Ser Phe Lys Ser Arg Glu Tyr Tyr
305                 310                 315                 320
```

-continued

```
Ile Thr Met Val Lys Trp Val Ser Asn Thr Lys Thr Val Val Arg Trp
                325                 330                 335

Leu Asn Arg Pro Gln Asn Ile Ser Ile Leu Thr Val Cys Glu Thr Thr
            340                 345                 350

Thr Gly Ala Cys Ser Lys Lys Tyr Glu Met Thr Ser Asp Thr Trp Leu
        355                 360                 365

Ser Gln Gln Asn Glu Glu Pro Val Phe Ser Arg Asp Gly Ser Lys Phe
    370                 375                 380

Phe Met Thr Val Pro Val Lys Gln Gly Gly Arg Gly Glu Phe His His
385                 390                 395                 400

Ile Ala Met Phe Leu Ile Gln Ser Lys Ser Glu Gln Ile Thr Val Arg
                405                 410                 415

His Leu Thr Ser Gly Asn Trp Glu Val Ile Lys Ile Leu Ala Tyr Asp
            420                 425                 430

Glu Thr Thr Gln Lys Ile Tyr Phe Leu Ser Thr Glu Ser Ser Pro Arg
        435                 440                 445

Gly Arg Gln Leu Tyr Ser Ala Ser Thr Glu Gly Leu Leu Asn Arg Gln
    450                 455                 460

Cys Ile Ser Cys Asn Phe Met Lys Glu Gln Cys Thr Tyr Phe Asp Ala
465                 470                 475                 480

Ser Phe Ser Pro Met Asn Gln His Phe Leu Leu Phe Cys Glu Gly Pro
                485                 490                 495

Arg Val Pro Val Val Ser Leu His Ser Thr Asp Asn Pro Ala Lys Tyr
            500                 505                 510

Phe Ile Leu Glu Ser Asn Ser Met Leu Lys Glu Ala Ile Leu Lys Lys
        515                 520                 525

Lys Ile Gly Lys Pro Glu Ile Lys Ile Leu His Ile Asp Asp Tyr Glu
    530                 535                 540

Leu Pro Leu Gln Leu Ser Leu Pro Lys Asp Phe Met Asp Arg Asn Gln
545                 550                 555                 560

Tyr Ala Leu Leu Leu Ile Met Asp Glu Glu Pro Gly Gly Gln Leu Val
                565                 570                 575

Thr Asp Lys Phe His Ile Asp Trp Asp Ser Val Leu Ile Asp Met Asp
            580                 585                 590

Asn Val Ile Val Ala Arg Phe Asp Gly Arg Gly Ser Gly Phe Gln Gly
        595                 600                 605

Leu Lys Ile Leu Gln Glu Ile His Arg Arg Leu Gly Ser Val Glu Val
    610                 615                 620

Lys Asp Gln Ile Thr Ala Val Lys Phe Leu Leu Lys Leu Pro Tyr Ile
625                 630                 635                 640

Asp Ser Lys Arg Leu Ser Ile Phe Gly Lys Gly Tyr Gly Gly Tyr Ile
                645                 650                 655

Ala Ser Met Ile Leu Lys Ser Asp Glu Lys Leu Phe Lys Cys Gly Ser
            660                 665                 670

Val Val Ala Pro Ile Thr Asp Leu Lys Leu Tyr Ala Ser Ala Phe Ser
        675                 680                 685

Glu Arg Tyr Leu Gly Met Pro Ser Lys Glu Glu Ser Thr Tyr Gln Ala
    690                 695                 700

Ala Ser Val Leu His Asn Val His Gly Leu Lys Glu Glu Asn Ile Leu
705                 710                 715                 720

Ile Ile His Gly Thr Ala Asp Thr Lys Val His Phe Gln His Ser Ala
                725                 730                 735
```

-continued

```
Glu Leu Ile Lys His Leu Ile Lys Ala Gly Val Asn Tyr Thr Met Gln
            740                 745                 750

Val Tyr Pro Asp Glu Gly His Asn Val Ser Glu Lys Ser Lys Tyr His
        755                 760                 765

Leu Tyr Ser Thr Ile Leu Lys Phe Phe Ser Asp Cys Leu Lys Glu Glu
    770                 775                 780

Ile Ser Val Leu Pro Gln Glu Pro Glu Glu Asp Glu
785                 790                 795


<210> SEQ ID NO 6
<211> LENGTH: 2583
<212> TYPE: DNA
<213> ORGANISM: Homo sapiens

<400> SEQUENCE: 6

gcctgggatt gtgcactgtc cagggtcctg aaacatgaac caaactgcca gcgtgtccca     60

tcacatcaag tgtcaaccct caaaaacaat caaggaactg ggaagtaaca gccctccaca    120

gagaaactgg aagggaattg ctattgctct gctggtgatt ttagttgtat gctcactcat    180

cactatgtca gtcatcctct taagcccaga tgaactcaca aattcgtcag aaaccagatt    240

gtctttggaa gacctcttta ggaaagactt tgtgcttcac gatccagagg ctcggtggat    300

caatgataca gatgtggtgt ataaaagcga gaatggacat gtcattaaac tgaatataga    360

aacaaatgct accacattat tattggaaaa cacaactttt gtaaccttca aagcatcaag    420

acattcagtt tcaccagatt taaaatatgt ccttctggca tatgatgtca aacagatttt    480

tcattattcg tatactgctt catatgtgat ttacaacata cacactaggg aagtttggga    540

gttaaatcct ccagaagtag aggactccgt cttgcagtac gcggcctggg gtgtccaagg    600

gcagcagctg atttatattt ttgaaaataa tatctactat caacctgata taaagagcag    660

ttcattgcga ctgacatctt ctggaaaaga agaaataatt tttaatggga ttgctgactg    720

gttatatgaa gaggaactcc tgcattctca catcgcccac tggtggtcac cagatggaga    780

aagacttgcc ttcctgatga taaatgactc tttggtaccc accatggtta tccctcggtt    840

tactggagcg ttgtatccca aggaaagca gtatccgtat cctaaggcag gtcaagtgaa    900

cccaacaata aaattatatg ttgtaaacct gtatggacca actcacactt tggagctcat    960

gccacctgac agctttaaat caagagaata ctatatcact atggttaaat gggtaagcaa   1020

taccaagact gtggtaagat ggttaaaccg acctcagaac atctccatcc tcacagtctg   1080

tgagaccact acaggtgctt gtagtaaaaa atatgagatg acatcagata cgtggctctc   1140

tcagcagaat gaggagcccg tgttttctag agacggcagc aaattcttta tgacagtgcc   1200

tgttaagcaa gggggacgtg gagaatttca ccacatagct atgttcctca tccagagtaa   1260

aagtgagcaa attaccgtgc ggcatctgac atcaggaaac tgggaagtga taaagatctt   1320

ggcatacgat gaaactactc aaaaaattta ctttctgagc actgaatctt ctcccagagg   1380

aaggcagctg tacagtgctt ctactgaagg attattgaat cgccaatgca tttcatgtaa   1440

tttcatgaaa gaacaatgta catattttga tgccagtttt agtcccatga atcaacattt   1500

cttattattc tgtgaaggtc caagggtccc agtggtcagc ctacatagta cggacaaccc   1560

agcaaaatat tttatattgg aaagcaattc tatgctgaag gaagctatcc tgaagaagaa   1620

gataggaaag ccagaaatta aaatccttca tattgacgac tatgaacttc ctttacagtt   1680

gtcccttccc aaagatttta tggaccgaaa ccagtatgct cttctgttaa taatggatga   1740

agaaccagga ggccagctgg ttacagataa gttccatatt gactgggatt ccgtactcat   1800
```

-continued

```
tgacatggat aatgtcattg tagcaagatt tgatggcaga ggaagtggat tccagggtct   1860

gaaaattttg caggagattc atcgaagatt aggttcagta gaagtaaagg accaaataac   1920

agctgtgaaa tttttgctga aactgcctta cattgactcc aaaagattaa gcatttttgg   1980

aaagggttat ggtggctata ttgcatcaat gatcttaaaa tcagatgaaa agctttttaa   2040

atgtggatcc gtggttgcac ctatcacaga cttgaaattg tatgcctcag ctttctctga   2100

aagatacctt gggatgccat ctaaggaaga aagcacttac caggcagcca gtgtgctaca   2160

taatgttcat ggcttgaaag aagaaaatat attaataatt catggaactg ctgacacaaa   2220

agttcatttc caacactcag cagaattaat caagcaccta ataaaagctg gagtgaatta   2280

tactatgcag gtctacccag atgaaggtca taacgtatct gagaagagca agtatcatct   2340

ctacagcaca atcctcaaat tcttcagtga ttgtttgaag gaagaaatat ctgtgctacc   2400

acaggaacca gaagaagatg aataatggac cgtatttata cagaactgaa gggaatattg   2460

aggctcaatg aaacctgaca aagagactgt aatattgtag ttgctccaga atgtcaaggg   2520

cagcttacgg agatgtcact ggagcagcac gctcagagac agtgaactag catttgaata   2580

cac                                                                 2583
```

```
<210> SEQ ID NO 7
<211> LENGTH: 690
<212> TYPE: PRT
<213> ORGANISM: Homo sapiens

<400> SEQUENCE: 7

Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Glu Asn Arg Glu Asn Thr
                85                  90                  95

Leu Phe Tyr Ser Glu Ile Pro Lys Thr Ile Asn Arg Ala Ala Val Leu
            100                 105                 110

Met Leu Ser Trp Lys Pro Leu Leu Asp Leu Phe Gln Ala Thr Leu Asp
        115                 120                 125

Tyr Gly Met Tyr Ser Arg Glu Glu Glu Leu Leu Arg Glu Arg Lys Arg
    130                 135                 140

Ile Gly Thr Val Gly Ile Ala Ser Tyr Asp Tyr His Gln Gly Ser Gly
145                 150                 155                 160

Thr Phe Leu Phe Gln Ala Gly Ser Gly Ile Tyr His Val Lys Asp Gly
                165                 170                 175

Gly Pro Gln Gly Phe Thr Gln Gln Pro Leu Arg Pro Asn Leu Val Glu
            180                 185                 190

Thr Ser Cys Pro Asn Ile Arg Met Asp Pro Lys Leu Cys Pro Ala Asp
        195                 200                 205

Pro Asp Trp Ile Ala Phe Ile His Ser Asn Asp Ile Trp Ile Ser Asn
    210                 215                 220
```

-continued

```
Ile Val Thr Arg Glu Glu Arg Arg Leu Thr Tyr Val His Asn Glu Leu
225                 230                 235                 240

Ala Asn Met Glu Glu Asp Ala Arg Ser Ala Gly Val Ala Thr Phe Val
                245                 250                 255

Leu Gln Glu Glu Phe Asp Arg Tyr Ser Gly Tyr Trp Trp Cys Pro Lys
            260                 265                 270

Ala Glu Thr Thr Pro Ser Gly Gly Lys Ile Leu Arg Ile Leu Tyr Glu
        275                 280                 285

Glu Asn Asp Glu Ser Glu Val Glu Ile Ile His Val Thr Ser Pro Met
    290                 295                 300

Leu Glu Thr Arg Arg Ala Asp Ser Phe Arg Tyr Pro Lys Thr Gly Thr
305                 310                 315                 320

Ala Asn Pro Lys Val Thr Phe Lys Met Ser Glu Ile Met Ile Asp Ala
                325                 330                 335

Glu Gly Arg Ile Ile Asp Val Ile Asp Lys Glu Leu Ile Gln Pro Phe
            340                 345                 350

Glu Ile Leu Phe Glu Gly Val Glu Tyr Ile Ala Arg Ala Gly Trp Thr
        355                 360                 365

Pro Glu Gly Lys Tyr Ala Trp Ser Ile Leu Leu Asp Arg Ser Gln Thr
    370                 375                 380

Arg Leu Gln Ile Val Leu Ile Ser Pro Glu Leu Phe Ile Pro Val Glu
385                 390                 395                 400

Asp Asp Val Met Glu Arg Gln Arg Leu Ile Glu Ser Val Pro Asp Ser
                405                 410                 415

Val Thr Pro Leu Ile Ile Tyr Glu Glu Thr Thr Asp Ile Trp Ile Asn
            420                 425                 430

Ile His Asp Ile Phe His Val Phe Pro Gln Ser His Glu Glu Glu Ile
        435                 440                 445

Glu Phe Ile Phe Ala Ser Glu Cys Lys Thr Gly Phe Arg His Leu Tyr
    450                 455                 460

Lys Ile Thr Ser Ile Leu Lys Glu Ser Lys Tyr Lys Arg Ser Ser Gly
465                 470                 475                 480

Gly Leu Pro Ala Pro Ser Asp Phe Lys Cys Pro Ile Lys Glu Glu Ile
                485                 490                 495

Ala Ile Thr Ser Gly Glu Trp Glu Val Leu Gly Arg His Gly Ser Asn
            500                 505                 510

Ile Gln Val Asp Glu Val Arg Arg Leu Val Tyr Phe Glu Gly Thr Lys
        515                 520                 525

Asp Ser Pro Leu Glu His His Leu Tyr Val Val Ser Tyr Val Asn Pro
    530                 535                 540

Gly Glu Val Thr Arg Leu Thr Asp Arg Gly Tyr Ser His Ser Cys Cys
545                 550                 555                 560

Ile Ser Gln His Cys Asp Phe Phe Ile Ser Lys Tyr Ser Asn Gln Lys
                565                 570                 575

Asn Pro His Cys Val Ser Leu Tyr Lys Leu Ser Ser Pro Glu Asp Asp
            580                 585                 590

Pro Thr Cys Lys Thr Lys Glu Phe Trp Ala Thr Ile Leu Asp Ser Ala
        595                 600                 605

Gly Pro Leu Pro Asp Tyr Thr Pro Pro Glu Ile Phe Ser Phe Glu Ser
    610                 615                 620

Thr Thr Gly Phe Thr Leu Tyr Gly Met Leu Tyr Lys Pro His Asp Leu
625                 630                 635                 640

Gln Pro Gly Lys Lys Tyr Pro Thr Val Leu Phe Ile Tyr Gly Gly Arg
```

-continued

```
                645                 650                 655

Leu Leu Leu Leu Gly Pro Gln Ser Leu Cys Gly Ser Ser Met Ile Gln
            660                 665                 670

Asp Thr Arg Asn Val Ile Trp Val Thr Leu Thr Arg Met Asn Arg Ala
        675                 680                 685

Ile Thr
    690
```

<210> SEQ ID NO 8
<211> LENGTH: 4523
<212> TYPE: DNA
<213> ORGANISM: Homo sapiens

<400> SEQUENCE: 8

```
aagtgctaaa gcctccgagg ccaaggccgc tgctactgcc gccgctgctt cttagtgccg     60

cgttcgccgc ctgggttgtc accggcgccg ccgccgagga agccactgca accaggaccg    120

gagtggaggc ggcgcagcat gaagcggcgc aggcccgctc catagcgcac gtcgggacgg    180

tccgggcggg gccgggggga aggaaaatgc aacatggcag cagcaatgga aacagaacag    240

ctgggtgttg agatatttga aactgcggac tgtgaggaga atattgaatc acaggatcgg    300

cctaaattgg agcctttttta tgttgagcgg tattcctgga gtcagcttaa aaagctgctt    360

gccgatacca gaaaatatca tggctacatg atggctaagg caccacatga tttcatgttt    420

gtgaagagga atgatccaga tggacctcat tcagacagaa tctattacct tgccatgtct    480

ggtgagaaca gagaaaatac actgttttat tctgaaattc ccaaaactat caatagagca    540

gcagtcttaa tgctctcttg gaagcctctt ttggatcttt ttcaggcaac actggactat    600

ggaatgtatt ctcgagaaga agaactatta agagaaagaa aacgcattgg aacagtcgga    660

attgcttctt acgattatca ccaaggaagt ggaacatttc tgtttcaagc cggtagtgga    720

atttatcacg taaaagatgg agggccacaa ggatttacgc aacaaccttt aaggcccaat    780

ctagtggaaa ctagttgtcc caacatacgg atggatccaa aattatgccc tgctgatcca    840

gactggattg cttttataca tagcaacgat atttggatat ctaacatcgt aaccagagaa    900

gaaaggagac tcacttatgt gcacaatgag ctagccaaca tggaagaaga tgccagatca    960

gctggagtcg ctacctttgt tctccaagaa gaatttgata gatattctgg ctattggtgg   1020

tgtccaaaag ctgaaacaac tcccagtggt ggtaaaattc ttagaattct atatgaagaa   1080

aatgatgaat ctgaggtgga aattattcat gttacatccc ctatgttgga aacaaggagg   1140

gcagattcat tccgttatcc taaaacaggt acagcaaatc ctaaagtcac ttttaagatg   1200

tcagaaataa tgattgatgc tgaaggaagg atcatagatg tcatagataa ggaactaatt   1260

caaccttttg agattctatt tgaaggagtt gaatatattg ccagagctgg atggactcct   1320

gagggaaaat atgcttggtc catcctacta gatcgctccc agactcgcct acagatagtg   1380

ttgatctcac ctgaattatt tatcccagta gaagatgatg ttatggaaag gcagagactc   1440

attgagtcag tgcctgattc tgtgacgcca ctaattatct atgaagaaac aacagacatc   1500

tggataaata tccatgacat ctttcatgtt tttccccaaa gtcacgaaga ggaaattgag   1560

tttatttttg cctctgaatg caaaacaggt ttccgtcatt tatacaaaat tacatctatt   1620

ttaaaggaaa gcaaatataa acgatccagt ggtgggctgc ctgctccaag tgatttcaag   1680

tgtcctatca aagaggagat agcaattacc agtggtgaat gggaagttct tggccggcat   1740

ggatctaata tccaagttga tgaagtcaga aggctggtat attttgaagg caccaaagac   1800
```

-continued

```
tcccctttag agcatcacct gtacgtagtc agttacgtaa atcctggaga ggtgacaagg   1860
ctgactgacc gtggctactc acattcttgc tgcatcagtc agcactgtga cttctttata   1920
agtaagtata gtaaccagaa gaatccacac tgtgtgtccc tttacaagct atcaagtcct   1980
gaagatgacc caacttgcaa aacaaaggaa ttttgggcca ccattttgga ttcagcaggt   2040
cctcttcctg actatactcc tccagaaatt ttctcttttg aaagtactac tggatttaca   2100
ttgtatggga tgctctacaa gcctcatgat ctacagcctg gaaagaaata tcctactgtg   2160
ctgttcatat atggtggtcg gttgctattg ctggggcccc agtcactctg tggatcttct   2220
atgatacagg atacacggaa cgttatatgg gtcaccctga ccagaatgaa cagggctatt   2280
acttaggatc tgtggccatg caagcagaaa agttcccctc tgaaccaaat cgtttactgc   2340
tcttacatgg tttcctggat gagaatgtcc attttgcaca taccagtata ttactgagtt   2400
ttttagtgag ggctggaaag ccatatgatt tacagatcta tcctcaggag agacacagca   2460
taagagttcc tgaatcggga gaacattatg aactgcatct tttgcactac cttcaagaaa   2520
accttggatc acgtattgct gctctaaaag tgatataatt ttgacctgtg tagaactctc   2580
tggtatacac tggctattta accaaatgag gaggtttaat caacagaaaa cacagaattg   2640
atcatcacat tttgatacct gccatgtaac atctactcct gaaaataaat gtggtgccat   2700
gcaggggtct acggtttgtg gtagtaatct aataccttaa ccccacatgc tcaaaatcaa   2760
atgatacata ttcctgagag acccagcaat accataagaa ttactaaaaa aaaaaaaaaa   2820
aaaaagacat tagcaccatg tattcatact accctatttt cacttttaat agtattataa   2880
acttcatgaa cttaattagt gtatttttac agtatacttt tgagtttgtt aaaatatgat   2940
gatattagtg attggtttgg ttcagttcca gaatctttga ctagttacag atttgatagc   3000
acttaaatgt aattgaatag cttatgcttc attgcttggg catatccagc atgttatgaa   3060
ctaataacta ttaaacttga cttaaccagt cattcattaa taatttttca aggataactt   3120
agtggcctcc taaagacact tgttttggca ctgaccagtt tttagccaat ttaatctgta   3180
tctagtataa ataattctca tttttctttg atgatattaa cagagtgggc ttttcctttt   3240
gcataaaggc tagtaactgt atatgtagca tggatttaat tagtcatgat attgataatt   3300
acaggcagaa aatttttaat caaatgatta gagcttaaat atttgcaggc aagttttttt   3360
ttttccttta agaaaaggaa aaagtacaca ttcactagaa ttcttcagaa aatttagtgg   3420
tgccagtttc catttggtat ttccttatta aaatattcta gaattttaag gagattgaag   3480
ggaatcacag tggggtgggg agacctgggt ttggggaatg acagagagaa gaggtggtga   3540
gggcctgatt aaaaactaag cagaagtagt tttaacaaaa atactcatga aaatgtttgg   3600
aaactgaaat ttaaacaact gtaatattaa ggaaaccaga atcaataaat cactgtcttg   3660
ccagcacagc tacagagtaa catgattcag gggaggaaaa gttccttaga gttactttta   3720
taattctttt tttttttcct cttaggttta gaaatcttac aaatttaaac tttatccttt   3780
taaaattatt tgaacataat ttagatattg taagcttaaa atacaaatgt ttatagataa   3840
cctctttacc ataaactaat ccctggcaag ccatggctct cttttttttt ttggtgttta   3900
aagcctgtaa acagtttttc tgaatgatca tgaacttttc ttggtttagc actaggattt   3960
agctatgaag agagctcata ggctttcagg tgctaattga gatctgccct gttagagtct   4020
tggggtgcta gattggtcac attgacacca gtggcaggga aggcatctat gagtttgatg   4080
ctttttatca cacacttcag tgtttagaaa gttattacca atacttttaa acaacactcc   4140
aagaaaattt gctatatttc tttctcatca ctacagagag agtagatttc cccatagaga   4200
```

-continued

```
gcacagcctc cattagtaag gttggtgact attggtaaga ggtggacttc attgacacca   4260

agtgggaggt agggaaagcc cagaaatggc aggatgatat ggtggttctg tcgttgggaa   4320

aggtattggg ttttgctgtt tgtatttata ctgtataata gataccacgc tttttcttat   4380

tatctgtata tgtattgctt ttcatgtttg atattttccc atgccaagat ttgtttatat   4440

atattttcaa tgttaaatta aattgatttg ggtaactttc ttccccaaga aagtattttc   4500

ccccttaagt ataaatctga ctg                                           4523
```

<210> SEQ ID NO 9
<211> LENGTH: 241
<212> TYPE: PRT
<213> ORGANISM: Homo sapiens

<400> SEQUENCE: 9

```
Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Glu Asn Arg Glu Asn Thr
                85                  90                  95

Leu Phe Tyr Ser Glu Ile Pro Lys Thr Ile Asn Arg Ala Ala Val Leu
            100                 105                 110

Met Leu Ser Trp Lys Pro Leu Leu Asp Leu Phe Gln Ala Thr Leu Asp
        115                 120                 125

Tyr Gly Met Tyr Ser Arg Glu Glu Glu Leu Leu Arg Glu Arg Lys Arg
    130                 135                 140

Ile Gly Thr Val Gly Ile Ala Ser Tyr Asp Tyr His Gln Gly Ser Gly
145                 150                 155                 160

Thr Phe Leu Phe Gln Ala Gly Ser Gly Ile Tyr His Val Lys Asp Gly
                165                 170                 175

Gly Pro Gln Gly Phe Thr Gln Gln Pro Leu Arg Pro Asn Leu Val Glu
            180                 185                 190

Thr Ser Cys Pro Asn Ile Arg Met Asp Pro Lys Leu Cys Pro Ala Asp
        195                 200                 205

Pro Asp Trp Ile Ala Phe Ile His Ser Asn Asp Ile Trp Ile Ser Asn
    210                 215                 220

Ile Val Thr Arg Glu Glu Arg Arg Leu Thr Tyr Val His Asn Gly Lys
225                 230                 235                 240

Ala
```

<210> SEQ ID NO 10
<211> LENGTH: 1356
<212> TYPE: DNA
<213> ORGANISM: Homo sapiens

<400> SEQUENCE: 10

```
aagtgctaaa gcctccgagg ccaaggccgc tgctactgcc gccgctgctt cttagtgccg     60

cgttcgccgc ctgggttgtc accggcgccg ccgccgagga agccactgca accaggaccg    120
```

-continued

```
gagtggaggc ggcgcagcat gaagcggcgc aggcccgctc catagcgcac gtcgggacgg    180

tccgggcggg gccgggggga aggaaaatgc aacatggcag cagcaatgga aacagaacag    240

ctgggtgttg agatatttga aactgcggac tgtgaggaga atattgaatc acaggatcgg    300

cctaaattgg agccttttta tgttgagcgg tattcctgga gtcagcttaa aaagctgctt    360

gccgatacca gaaaatatca tggctacatg atggctaagg caccacatga tttcatgttt    420

gtgaagagga atgatccaga tggacctcat tcagacagaa tctattacct tgccatgtct    480

ggtgagaaca gagaaaatac actgttttat tctgaaattc ccaaaactat caatagagca    540

gcagtcttaa tgctctcttg gaagcctctt ttggatcttt ttcaggcaac actggactat    600

ggaatgtatt ctcgagaaga agaactatta agagaaagaa aacgcattgg aacagtcgga    660

attgcttctt acgattatca ccaaggaagt ggaacatttc tgtttcaagc cggtagtgga    720

atttatcacg taaaagatgg agggccacaa ggatttacgc aacaaccttt aaggcccaat    780

ctagtggaaa ctagttgtcc caacatacgg atggatccaa aattatgccc tgctgatcca    840

gactggattg cttttataca tagcaacgat atttggatat ctaacatcgt aaccagagaa    900

gaaaggagac tcacttatgt gcacaatggt aaggcgtagt tcttcagatt tacttttctg    960

aacagtattt tttgaagtat aatttgctgc ttgcattttg aaattagatt accacgttgg   1020

gtgatcttta tatttgaaat tcaagtcttt aaaattttta aaaaatggag aaaagtacag   1080

aggataactt gtatgtacca catgtataat attcatttta atgttttaat gttcattttc   1140

aaacagtgaa acaaaagaac ctctgacatg attgttcttt tagcttgcta agactgccag   1200

aattttccca aaactgttct tattaaaata aaattttagg ctaggcatgg tggctcatgc   1260

ctgtaatcct agcactctgg gaggctgagg caggcagatt gtttgagccc agaagttcaa   1320

gatcaggatg ggcaacatgg tgacacctcg tttgac                             1356
```

```
<210> SEQ ID NO 11
<211> LENGTH: 661
<212> TYPE: PRT
<213> ORGANISM: Homo sapiens

<400> SEQUENCE: 11

Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Glu Asn Arg Glu Asn Thr
                85                  90                  95

Leu Phe Tyr Ser Glu Ile Pro Lys Thr Ile Asn Arg Ala Ala Val Leu
            100                 105                 110

Met Leu Ser Trp Lys Pro Leu Leu Asp Leu Phe Gln Ala Thr Leu Asp
        115                 120                 125

Tyr Gly Met Tyr Ser Arg Glu Glu Glu Leu Leu Arg Glu Arg Lys Arg
    130                 135                 140

Ile Gly Thr Val Gly Ile Ala Ser Tyr Asp Tyr His Gln Gly Ser Gly
```

-continued

```
145                 150                 155                 160

Thr Phe Leu Phe Gln Ala Gly Ser Gly Ile Tyr His Val Lys Asp Gly
                165                 170                 175

Gly Pro Gln Gly Phe Thr Gln Gln Pro Leu Arg Pro Asn Leu Val Glu
            180                 185                 190

Thr Ser Cys Pro Asn Ile Arg Met Asp Pro Lys Leu Cys Pro Ala Asp
        195                 200                 205

Pro Asp Trp Ile Ala Phe Ile His Ser Asn Asp Ile Trp Ile Ser Asn
    210                 215                 220

Ile Val Thr Arg Glu Glu Arg Arg Leu Thr Tyr Val His Asn Glu Leu
225                 230                 235                 240

Ala Asn Met Glu Glu Asp Ala Arg Ser Ala Gly Val Ala Thr Phe Val
                245                 250                 255

Leu Gln Glu Glu Phe Asp Arg Tyr Ser Gly Tyr Trp Trp Cys Pro Lys
            260                 265                 270

Ala Glu Thr Thr Pro Ser Gly Gly Lys Ile Leu Arg Ile Leu Tyr Glu
        275                 280                 285

Glu Asn Asp Glu Ser Glu Val Glu Ile Ile His Val Thr Ser Pro Met
    290                 295                 300

Leu Glu Thr Arg Arg Ala Asp Ser Phe Arg Tyr Pro Lys Thr Gly Thr
305                 310                 315                 320

Ala Asn Pro Lys Val Thr Phe Lys Met Ser Glu Ile Met Ile Asp Ala
                325                 330                 335

Glu Gly Arg Ile Ile Asp Val Ile Asp Lys Glu Leu Ile Gln Pro Phe
            340                 345                 350

Glu Ile Leu Phe Glu Gly Val Glu Tyr Ile Ala Arg Ala Gly Trp Thr
        355                 360                 365

Pro Glu Gly Lys Tyr Ala Trp Ser Ile Leu Leu Asp Arg Ser Gln Thr
    370                 375                 380

Arg Leu Gln Ile Val Leu Ile Ser Pro Glu Leu Phe Ile Pro Val Glu
385                 390                 395                 400

Asp Asp Val Met Glu Arg Gln Arg Leu Ile Glu Ser Val Pro Asp Ser
                405                 410                 415

Val Thr Pro Leu Ile Ile Tyr Glu Glu Thr Thr Asp Ile Trp Ile Asn
            420                 425                 430

Ile His Asp Ile Phe His Val Phe Pro Gln Ser His Glu Glu Glu Ile
        435                 440                 445

Glu Phe Ile Phe Ala Ser Glu Cys Lys Thr Gly Phe Arg His Leu Tyr
    450                 455                 460

Lys Ile Thr Ser Ile Leu Lys Glu Ser Lys Tyr Lys Arg Ser Ser Gly
465                 470                 475                 480

Gly Leu Pro Ala Pro Ser Asp Phe Lys Cys Pro Ile Lys Glu Glu Ile
                485                 490                 495

Ala Ile Thr Ser Gly Glu Trp Glu Val Leu Gly Arg His Gly Ser Asn
            500                 505                 510

Ile Gln Val Asp Glu Val Arg Arg Leu Val Tyr Phe Glu Gly Thr Lys
        515                 520                 525

Asp Ser Pro Leu Glu His His Leu Tyr Val Val Ser Tyr Val Asn Pro
    530                 535                 540

Gly Glu Val Thr Arg Leu Thr Asp Arg Gly Tyr Ser His Ser Cys Cys
545                 550                 555                 560

Ile Ser Gln His Cys Asp Phe Phe Ile Ser Lys Tyr Ser Asn Gln Lys
                565                 570                 575
```

-continued

```
Asn Pro His Cys Val Ser Leu Tyr Lys Leu Ser Ser Pro Glu Asp Asp
            580                 585                 590

Pro Thr Cys Lys Thr Lys Glu Phe Trp Ala Thr Ile Leu Asp Ser Ala
        595                 600                 605

Gly Pro Leu Pro Asp Tyr Thr Pro Pro Glu Ile Phe Ser Phe Glu Ser
    610                 615                 620

Thr Thr Gly Phe Thr Leu Tyr Gly Met Leu Tyr Lys Pro His Asp Leu
625                 630                 635                 640

Gln Pro Gly Lys Lys Tyr Pro Thr Val Leu Phe Ile Tyr Gly Gly Leu
                645                 650                 655

Leu Arg Cys Ser Trp
            660


<210> SEQ ID NO 12
<211> LENGTH: 4829
<212> TYPE: DNA
<213> ORGANISM: Homo sapiens

<400> SEQUENCE: 12

aagtgctaaa gcctccgagg ccaaggccgc tgctactgcc gccgctgctt cttagtgccg     60

cgttcgccgc ctgggttgtc accggcgccg ccgccgagga agccactgca accaggaccg    120

gagtggaggc ggcgcagcat gaagcggcgc aggcccgctc catagcgcac gtcgggacgg    180

tccgggcggg gccgggggga aggaaaatgc aacatggcag cagcaatgga aacagaacag    240

ctgggtgttg agatatttga aactgcggac tgtgaggaga atattgaatc acaggatcgg    300

cctaaattgg agcctttttta tgttgagcgg tattcctgga gtcagcttaa aaagctgctt    360

gccgatacca gaaaatatca tggctacatg atggctaagg caccacatga tttcatgttt    420

gtgaagagga atgatccaga tggacctcat tcagacagaa tctattacct tgccatgtct    480

ggtgagaaca gagaaaatac actgttttat tctgaaattc ccaaaactat caatagagca    540

gcagtcttaa tgctctcttg gaagcctctt ttggatcttt ttcaggcaac actggactat    600

ggaatgtatt ctcgagaaga agaactatta agagaaagaa aacgcattgg aacagtcgga    660

attgcttctt acgattatca ccaaggaagt ggaacatttc tgtttcaagc cggtagtgga    720

atttatcacg taaaagatgg agggccacaa ggatttacgc aacaaccttt aaggcccaat    780

ctagtggaaa ctagttgtcc caacatacgg atggatccaa aattatgccc tgctgatcca    840

gactggattg cttttataca tagcaacgat atttggatat ctaacatcgt aaccagagaa    900

gaaaggagac tcacttatgt gcacaatgag ctagccaaca tggaagaaga tgccagatca    960

gctggagtcg ctacctttgt tctccaagaa gaatttgata gatattctgg ctattggtgg   1020

tgtccaaaag ctgaaacaac tcccagtggt ggtaaaattc ttagaattct atatgaagaa   1080

aatgatgaat ctgaggtgga aattattcat gttacatccc ctatgttgga aacaaggagg   1140

gcagattcat tccgttatcc taaaacaggt acagcaaatc ctaaagtcac ttttaagatg   1200

tcagaaataa tgattgatgc tgaaggaagg atcatagatg tcatagataa ggaactaatt   1260

caaccttttg agattctatt tgaaggagtt gaatatattg ccagagctgg atggactcct   1320

gagggaaaat atgcttggtc catcctacta gatcgctccc agactcgcct acagatagtg   1380

ttgatctcac ctgaattatt tatcccagta gaagatgatg ttatggaaag gcagagactc   1440

attgagtcag tgcctgattc tgtgacgcca ctaattatct atgaagaaac aacagacatc   1500

tggataaata tccatgacat ctttcatgtt tttccccaaa gtcacgaaga ggaaattgag   1560
```

-continued

```
tttatttttg cctctgaatg caaaacaggt ttccgtcatt tatacaaaat tacatctatt   1620
ttaaaggaaa gcaaatataa acgatccagt ggtgggctgc ctgctccaag tgatttcaag   1680
tgtcctatca aagaggagat agcaattacc agtggtgaat gggaagttct tggccggcat   1740
ggatctaata tccaagttga tgaagtcaga aggctggtat attttgaagg caccaaagac   1800
tcccctttag agcatcacct gtacgtagtc agttacgtaa atcctggaga ggtgacaagg   1860
ctgactgacc gtggctactc acattcttgc tgcatcagtc agcactgtga cttctttata   1920
agtaagtata gtaaccagaa gaatccacac tgtgtgtccc tttacaagct atcaagtcct   1980
gaagatgacc caacttgcaa aacaaaggaa ttttgggcca ccattttgga ttcagcaggt   2040
cctcttcctg actatactcc tccagaaatt ttctcttttg aaagtactac tggatttaca   2100
ttgtatggga tgctctacaa gcctcatgat ctacagcctg gaaagaaata tcctactgtg   2160
ctgttcatat atggtggtct cctcaggtgc agttggtgaa taatcggttt aaaggagtca   2220
agtatttccg cttgaatacc ctagcctctc taggttatgt ggttgtagtg atagacaaca   2280
ggggatcctg tcaccgaggg cttaaatttg aaggcgcctt taaatataaa atgggtcaaa   2340
tagaaattga cgatcaggtg gaaggactcc aatatctagc ttctcgatat gatttcattg   2400
acttagatcg tgtgggcatc cacggctggt cctatggagg atacctctcc ctgatggcat   2460
taatgcagag gtcagatatc ttcagggttg ctattgctgg ggccccagtc actctgtgga   2520
tcttctatga tacaggatac acggaacgtt atatgggtca ccctgaccag aatgaacagg   2580
gctattactt aggatctgtg gccatgcaag cagaaaagtt cccctctgaa ccaaatcgtt   2640
tactgctctt acatggtttc ctggatgaga atgtccattt tgcacatacc agtatattac   2700
tgagtttttt agtgagggct ggaaagccat atgatttaca gatctatcct caggagagac   2760
acagcataag agttcctgaa tcgggagaac attatgaact gcatcttttg cactaccttc   2820
aagaaaacct tggatcacgt attgctgctc taaaagtgat ataattttga cctgtgtaga   2880
actctctggt atacactggc tatttaacca aatgaggagg tttaatcaac agaaaacaca   2940
gaattgatca tcacattttg atacctgcca tgtaacatct actcctgaaa ataaatgtgg   3000
tgccatgcag ggtctacgg tttgtggtag taatctaata ccttaacccc acatgctcaa   3060
aatcaaatga tacatattcc tgagagaccc agcaatacca taagaattac taaaaaaaaa   3120
aaaaaaaaaa agacattagc accatgtatt catactaccc tattttcact tttaatagta   3180
ttataaactt catgaactta attagtgtat ttttacagta tacttttgag tttgttaaaa   3240
tatgatgata ttagtgattg gtttggttca gttccagaat ctttgactag ttacagattt   3300
gatagcactt aaatgtaatt gaatagctta tgcttcattg cttgggcata tccagcatgt   3360
tatgaactaa taactattaa acttgactta accagtcatt cattaataat ttttcaagga   3420
taacttagtg gcctcctaaa gacacttgtt ttggcactga ccagtttttta gccaatttaa   3480
tctgtatcta gtataaataa ttctcatttt tctttgatga tattaacaga gtgggctttt   3540
ccttttgcat aaaggctagt aactgtatat gtagcatgga tttaattagt catgatattg   3600
ataattacag gcagaaaatt tttaatcaaa tgattagagc ttaaatattt gcaggcaagt   3660
tttttttttt cctttaagaa aaggaaaaag tacacattca ctagaattct tcagaaaatt   3720
tagtggtgcc agtttccatt tggtatttcc ttattaaaat attctagaat tttaaggaga   3780
ttgaagggaa tcacagtggg gtggggagac ctgggtttgg ggaatgacag agagaagagg   3840
tggtgagggc ctgattaaaa actaagcaga agtagtttta acaaaaatac tcatgaaaat   3900
gtttggaaac tgaaatttaa acaactgtaa tattaaggaa accagaatca ataaatcact   3960
```

-continued

```
gtcttgccag cacagctaca gagtaacatg attcagggga ggaaaagttc cttagagtta   4020

cttttataat tctttttttt tttcctctta ggtttagaaa tcttacaaat ttaaacttta   4080

tccttttaaa attatttgaa cataatttag atattgtaag cttaaaatac aaatgtttat   4140

agataacctc tttaccataa actaatccct ggcaagccat ggctctcttt tttttttgg   4200

tgtttaaagc ctgtaaacag tttttctgaa tgatcatgaa cttttcttgg tttagcacta   4260

ggatttagct atgaagagag ctcataggct ttcaggtgct aattgagatc tgccctgtta   4320

gagtcttggg gtgctagatt ggtcacattg acaccagtgg cagggaaggc atctatgagt   4380

ttgatgcttt ttatcacaca cttcagtgtt tagaaagtta ttaccaatac ttttaaacaa   4440

cactccaaga aaatttgcta tatttctttc tcatcactac agagagagta gatttcccca   4500

tagagagcac agcctccatt agtaaggttg gtgactattg gtaagaggtg gacttcattg   4560

acaccaagtg ggaggtaggg aaagcccaga aatggcagga tgatatggtg gttctgtcgt   4620

tgggaaaggt attgggtttt gctgtttgta tttatactgt ataatagata ccacgctttt   4680

tcttattatc tgtatatgta ttgcttttca tgtttgatat tttcccatgc caagatttgt   4740

ttatatatat tttcaatgtt aaattaaatt gatttgggta actttcttcc ccaagaaagt   4800

atttccccc ttaagtataa atctgactg                                      4829
```

<210> SEQ ID NO 13
<211> LENGTH: 358
<212> TYPE: PRT
<213> ORGANISM: Homo sapiens

<400> SEQUENCE: 13

```
Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Glu Asn Arg Glu Asn Thr
                85                  90                  95

Leu Phe Tyr Ser Glu Ile Pro Lys Thr Ile Asn Arg Ala Ala Val Leu
            100                 105                 110

Met Leu Ser Trp Lys Pro Leu Leu Asp Leu Phe Gln Ala Thr Leu Asp
        115                 120                 125

Tyr Gly Met Tyr Ser Arg Glu Glu Glu Leu Leu Arg Glu Arg Lys Arg
    130                 135                 140

Ile Gly Thr Val Gly Ile Ala Ser Tyr Asp Tyr His Gln Gly Ser Gly
145                 150                 155                 160

Thr Phe Leu Phe Gln Ala Gly Ser Gly Ile Tyr His Val Lys Asp Gly
                165                 170                 175

Gly Pro Gln Gly Phe Thr Gln Gln Pro Leu Arg Pro Asn Leu Val Glu
            180                 185                 190

Thr Ser Cys Pro Asn Ile Arg Met Asp Pro Lys Leu Cys Pro Ala Asp
        195                 200                 205

Pro Asp Trp Ile Ala Phe Ile His Ser Asn Asp Ile Trp Ile Ser Asn
```

-continued

```
    210                 215                 220

Ile Val Thr Arg Glu Glu Arg Arg Leu Thr Tyr Val His Asn Glu Leu
225                 230                 235                 240

Ala Asn Met Glu Glu Asp Ala Arg Ser Ala Gly Val Ala Thr Phe Val
                245                 250                 255

Leu Gln Glu Glu Phe Asp Arg Tyr Ser Gly Tyr Trp Trp Cys Pro Lys
            260                 265                 270

Ala Glu Thr Thr Pro Ser Gly Gly Lys Ile Leu Arg Ile Leu Tyr Glu
        275                 280                 285

Glu Asn Asp Glu Ser Glu Val Glu Ile Ile His Val Thr Ser Pro Met
    290                 295                 300

Leu Glu Thr Arg Arg Ala Asp Ser Phe Arg Tyr Pro Lys Thr Gly Thr
305                 310                 315                 320

Ala Asn Pro Lys Val Thr Phe Lys Met Ser Glu Ile Met Ile Asp Ala
                325                 330                 335

Glu Gly Arg Ser Lys Leu Met Lys Ser Glu Gly Trp Tyr Ile Leu Lys
            340                 345                 350

Ala Pro Lys Thr Pro Leu
        355


<210> SEQ ID NO 14
<211> LENGTH: 4309
<212> TYPE: DNA
<213> ORGANISM: Homo sapiens

<400> SEQUENCE: 14

aagtgctaaa gcctccgagg ccaaggccgc tgctactgcc gccgctgctt cttagtgccg     60

cgttcgccgc ctgggttgtc accggcgccg ccgccgagga agccactgca accaggaccg    120

gagtggaggc ggcgcagcat gaagcggcgc aggcccgctc catagcgcac gtcgggacgg    180

tccgggcggg gccgggggga aggaaaatgc aacatggcag cagcaatgga aacagaacag    240

ctgggtgttg agatatttga aactgcggac tgtgaggaga atattgaatc acaggatcgg    300

cctaaattgg agcctttttta tgttgagcgg tattcctgga gtcagcttaa aaagctgctt    360

gccgatacca gaaaatatca tggctacatg atggctaagg caccacatga tttcatgttt    420

gtgaagagga atgatccaga tggacctcat tcagacagaa tctattacct tgccatgtct    480

ggtgagaaca gagaaaatac actgttttat tctgaaattc ccaaaactat caatagagca    540

gcagtcttaa tgctctcttg gaagcctctt ttggatcttt ttcaggcaac actggactat    600

ggaatgtatt ctcgagaaga agaactatta agagaaagaa aacgcattgg aacagtcgga    660

attgcttctt acgattatca ccaaggaagt ggaacatttc tgtttcaagc cggtagtgga    720

atttatcacg taaaagatgg agggccacaa ggatttacgc aacaaccttt aaggcccaat    780

ctagtggaaa ctagttgtcc caacatacgg atggatccaa aattatgccc tgctgatcca    840

gactggattg cttttataca tagcaacgat atttggatat ctaacatcgt aaccagagaa    900

gaaaggagac tcacttatgt gcacaatgag ctagccaaca tggaagaaga tgccagatca    960

gctggagtcg ctacctttgt tctccaagaa gaatttgata gatattctgg ctattggtgg   1020

tgtccaaaag ctgaaacaac tcccagtggt ggtaaaattc ttagaattct atatgaagaa   1080

aatgatgaat ctgaggtgga aattattcat gttacatccc ctatgttgga aacaaggagg   1140

gcagattcat tccgttatcc taaaacaggt acagcaaatc ctaaagtcac ttttaagatg   1200

tcagaaataa tgattgatgc tgaaggaaga tccaagttga tgaagtcaga aggctggtat   1260
```

-continued

```
attttgaagg caccaaagac tcccctttag agcatcacct gtacgtagtc agttacgtaa   1320
atcctggaga ggtgacaagg ctgactgacc gtggctactc acattcttgc tgcatcagtc   1380
agcactgtga cttctttata agtaagtata gtaaccagaa gaatccacac tgtgtgtccc   1440
tttacaagct atcaagtcct gaagatgacc caacttgcaa aacaaaggaa ttttgggcca   1500
ccattttgga ttcagcaggt cctcttcctg actatactcc tccagaaatt ttctcttttg   1560
aaagtactac tggatttaca ttgtatggga tgctctacaa gcctcatgat ctacagcctg   1620
gaaagaaata tcctactgtg ctgttcatat atggtggtct cctcaggtgc agttggtgaa   1680
taatcggttt aaaggagtca agtatttccg cttgaatacc ctagcctctc taggttatgt   1740
ggttgtagtg atagacaaca ggggatcctg tcaccgaggg cttaaatttg aaggcgcctt   1800
taaatataaa atgggtcaaa tagaaattga cgatcaggtg gaaggactcc aatatctagc   1860
ttctcgatat gatttcattg acttagatcg tgtgggcatc cacggctggt cctatggagg   1920
atacctctcc ctgatggcat taatgcagag gtcagatatc ttcagggttg ctattgctgg   1980
ggccccagtc actctgtgga tcttctatga tacaggatac acggaacgtt atatgggtca   2040
ccctgaccag aatgaacagg gctattactt aggatctgtg gccatgcaag cagaaaagtt   2100
cccctctgaa ccaaatcgtt tactgctctt acatggtttc ctggatgaga atgtccattt   2160
tgcacatacc agtatattac tgagtttttt agtgagggct ggaaagccat atgatttaca   2220
gatctatcct caggagagac acagcataag agttcctgaa tcgggagaac attatgaact   2280
gcatcttttg cactaccttc aagaaaacct tggatcacgt attgctgctc taaaagtgat   2340
ataattttga cctgtgtaga actctctggt atacactggc tatttaacca aatgaggagg   2400
tttaatcaac agaaaacaca gaattgatca tcacattttg atacctgcca tgtaacatct   2460
actcctgaaa ataaatgtgg tgccatgcag gggtctacgg tttgtggtag taatctaata   2520
ccttaacccc acatgctcaa aatcaaatga tacatattcc tgagagaccc agcaatacca   2580
taagaattac taaaaaaaaa aaaaaaaaaa agacattagc accatgtatt catactaccc   2640
tattttcact tttaatagta ttataaactt catgaactta attagtgtat ttttacagta   2700
tacttttgag tttgttaaaa tatgatgata ttagtgattg gtttggttca gttccagaat   2760
ctttgactag ttacagattt gatagcactt aaatgtaatt gaatagctta tgcttcattg   2820
cttgggcata tccagcatgt tatgaactaa taactattaa acttgactta accagtcatt   2880
cattaataat ttttcaagga taacttagtg gcctcctaaa gacacttgtt ttggcactga   2940
ccagtttttta gccaatttaa tctgtatcta gtataaataa ttctcatttt tctttgatga   3000
tattaacaga gtgggctttt ccttttgcat aaaggctagt aactgtatat gtagcatgga   3060
tttaattagt catgatattg ataattacag gcagaaaatt tttaatcaaa tgattagagc   3120
ttaaatattt gcaggcaagt tttttttttt cctttaagaa aaggaaaaag tacacattca   3180
ctagaattct tcagaaaatt tagtggtgcc agtttccatt tggtatttcc ttattaaaat   3240
attctagaat tttaaggaga ttgaagggaa tcacagtggg gtggggagac ctgggtttgg   3300
ggaatgacag agagaagagg tggtgagggc ctgattaaaa actaagcaga agtagtttta   3360
acaaaaatac tcatgaaaat gtttggaaac tgaaatttaa acaactgtaa tattaaggaa   3420
accagaatca ataaatcact gtcttgccag cacagctaca gagtaacatg attcagggga   3480
ggaaaagttc cttagagtta cttttataat tctttttttt tttcctctta ggtttagaaa   3540
tcttacaaat ttaaacttta tccttttaaa attatttgaa cataatttag atattgtaag   3600
cttaaaatac aaatgtttat agataacctc tttaccataa actaatccct ggcaagccat   3660
```

-continued

```
ggctctcttt ttttttttgg tgtttaaagc ctgtaaacag tttttctgaa tgatcatgaa   3720

cttttcttgg tttagcacta ggatttagct atgaagagag ctcataggct ttcaggtgct   3780

aattgagatc tgccctgtta gagtcttggg gtgctagatt ggtcacattg acaccagtgg   3840

cagggaaggc atctatgagt ttgatgcttt ttatcacaca cttcagtgtt tagaaagtta   3900

ttaccaatac ttttaaacaa cactccaaga aaatttgcta tatttctttc tcatcactac   3960

agagagagta gatttcccca tagagagcac agcctccatt agtaaggttg gtgactattg   4020

gtaagaggtg gacttcattg acaccaagtg ggaggtaggg aaagcccaga aatggcagga   4080

tgatatggtg gttctgtcgt tgggaaaggt attgggtttt gctgtttgta tttatactgt   4140

ataatagata ccacgctttt tcttattatc tgtatatgta ttgcttttca tgtttgatat   4200

tttcccatgc caagatttgt ttatatatat tttcaatgtt aaattaaatt gatttgggta   4260

actttcttcc ccaagaaagt attttccccc ttaagtataa atctgactg              4309
```

<210> SEQ ID NO 15
<211> LENGTH: 108
<212> TYPE: PRT
<213> ORGANISM: Homo sapiens

<400> SEQUENCE: 15

```
Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Gly Asn Lys Ser Leu Ile Asp His Asp Arg
                85                  90                  95

Phe Ser Lys Ser Lys Met Pro Glu Ile Ala Ser Ser
            100                 105
```

<210> SEQ ID NO 16
<211> LENGTH: 620
<212> TYPE: DNA
<213> ORGANISM: Homo sapiens

<400> SEQUENCE: 16

```
aagtgctaaa gcctccgagg ccaaggccgc tgctactgcc gccgctgctt cttagtgccg     60

cgttcgccgc ctgggttgtc accggcgccg ccgccgagga agccactgca accaggaccg    120

gagtggaggc ggcgcagcat gaagcggcgc aggcccgctc catagcgcac gtcgggacgg    180

tccgggcggg gccgggggga aggaaaatgc aacatggcag cagcaatgga aacagaacag    240

ctgggtgttg agatatttga aactgcggac tgtgaggaga atattgaatc acaggatcgg    300

cctaaattgg agcctttttta tgttgagcgg tattcctgga gtcagcttaa aaagctgctt    360

gccgatacca gaaaatatca tggctacatg atggctaagg caccacatga tttcatgttt    420

gtgaagagga atgatccaga tggacctcat tcagacagaa tctattacct tggtaacaag    480

tcattaattg atcatgatcg tttttcaaaa tcgaagatgc cagaaattgc ttcttcctaa    540
```

-continued agctagcttg aaatgccttt ctttagatgg tctgattagg aaaacaaaca ataaaaccat 600
tagtttgttc ccactcaaca 620

<210> SEQ ID NO 17
<211> LENGTH: 194
<212> TYPE: PRT
<213> ORGANISM: Homo sapiens

<400> SEQUENCE: 17

Met Ala Ala Ala Met Glu Thr Glu Gln Leu Gly Val Glu Ile Phe Glu
1 5 10 15

Thr Ala Asp Cys Glu Glu Asn Ile Glu Ser Gln Asp Arg Pro Lys Leu
20 25 30

Glu Pro Phe Tyr Val Glu Arg Tyr Ser Trp Ser Gln Leu Lys Lys Leu
35 40 45

Leu Ala Asp Thr Arg Lys Tyr His Gly Tyr Met Met Ala Lys Ala Pro
50 55 60

His Asp Phe Met Phe Val Lys Arg Asn Asp Pro Asp Gly Pro His Ser
65 70 75 80

Asp Arg Ile Tyr Tyr Leu Ala Met Ser Gly Glu Asn Arg Glu Asn Thr
85 90 95

Leu Phe Tyr Ser Glu Ile Pro Lys Thr Ile Asn Arg Ala Ala Val Leu
100 105 110

Met Leu Ser Trp Lys Pro Leu Leu Asp Leu Phe Gln Ala Thr Leu Asp
115 120 125

Tyr Gly Met Tyr Ser Arg Glu Glu Glu Leu Leu Arg Glu Arg Lys Arg
130 135 140

Ile Gly Thr Val Gly Ile Ala Ser Tyr Asp Tyr His Gln Gly Ser Gly
145 150 155 160

Thr Phe Leu Phe Gln Ala Gly Ser Gly Ile Tyr His Val Lys Asp Gly
165 170 175

Gly Pro Gln Gly Phe Thr Gln Pro Leu Arg Pro Asn Leu Val Glu Thr
180 185 190

Cys Ala

<210> SEQ ID NO 18
<211> LENGTH: 832
<212> TYPE: DNA
<213> ORGANISM: Homo sapiens

<400> SEQUENCE: 18
aagtgctaaa gcctccgagg ccaaggccgc tgctactgcc gccgctgctt cttagtgccg 60
cgttcgccgc ctgggttgtc accggcgccg ccgccgagga agccactgca accaggaccg 120
gagtggaggc ggcgcagcat gaagcggcgc aggcccgctc catagcgcac gtcgggacgg 180
tccgggcggg gccgggggga aggaaaatgc aacatggcag cagcaatgga aacagaacag 240
ctgggtgttg agatatttga aactgcggac tgtgaggaga atattgaatc acaggatcgg 300
cctaaattgg agcctttttta tgttgagcgg tattcctgga gtcagcttaa aaagctgctt 360
gccgatacca gaaaatatca tggctacatg atggctaagg caccacatga tttcatgttt 420
gtgaagagga atgatccaga tggacctcat tcagacagaa tctattacct tgccatgtct 480
ggtgagaaca gagaaaatac actgttttat tctgaaattc ccaaaactat caatagagca 540
gcagtcttaa tgctctcttg gaagcctctt ttggatcttt ttcaggcaac actggactat 600
ggaatgtatt ctcgagaaga agaactatta agagaaagaa aacgcattgg aacagtcgga 660

-continued

```
attgcttctt acgattatca ccaaggaagt ggaacatttc tgtttcaagc cggtagtgga    720

atttatcacg taaaagatgg agggccacaa ggatttacgc wacaaccttt aaggcccaat    780

ctagtggaaa ctasttgtsc caracytgca tgacccaatc agatcctgta ga            832


<210> SEQ ID NO 19
<211> LENGTH: 658
<212> TYPE: PRT
<213> ORGANISM: Homo sapiens

<400> SEQUENCE: 19

Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Glu Asn Arg Glu Asn Thr
                85                  90                  95

Leu Phe Tyr Ser Glu Ile Pro Lys Thr Ile Asn Arg Ala Ala Val Leu
            100                 105                 110

Met Leu Ser Trp Lys Pro Leu Leu Asp Leu Phe Gln Ala Thr Leu Asp
        115                 120                 125

Tyr Gly Met Tyr Ser Arg Glu Glu Glu Leu Leu Arg Glu Arg Lys Arg
    130                 135                 140

Ile Gly Thr Val Gly Ile Ala Ser Tyr Asp Tyr His Gln Gly Ser Gly
145                 150                 155                 160

Thr Phe Leu Phe Gln Ala Gly Ser Gly Ile Tyr His Val Lys Asp Gly
                165                 170                 175

Gly Pro Gln Gly Phe Thr Gln Gln Pro Leu Arg Pro Asn Leu Val Glu
            180                 185                 190

Thr Ser Cys Pro Asn Ile Arg Met Asp Pro Lys Leu Cys Pro Ala Asp
        195                 200                 205

Pro Asp Trp Ile Ala Phe Ile His Ser Asn Asp Ile Trp Ile Ser Asn
    210                 215                 220

Ile Val Thr Arg Glu Glu Arg Arg Leu Thr Tyr Val His Asn Glu Leu
225                 230                 235                 240

Ala Asn Met Glu Glu Asp Ala Arg Ser Ala Gly Val Ala Thr Phe Val
                245                 250                 255

Leu Gln Glu Glu Phe Asp Arg Tyr Ser Gly Tyr Trp Trp Cys Pro Lys
            260                 265                 270

Ala Glu Thr Thr Pro Ser Gly Gly Lys Ile Leu Arg Ile Leu Tyr Glu
        275                 280                 285

Glu Asn Asp Glu Ser Glu Val Glu Ile Ile His Val Thr Ser Pro Met
    290                 295                 300

Leu Glu Thr Arg Arg Ala Asp Ser Phe Arg Tyr Pro Lys Thr Gly Thr
305                 310                 315                 320

Ala Asn Pro Lys Val Thr Phe Lys Met Ser Glu Ile Met Ile Asp Ala
                325                 330                 335

Glu Gly Arg Ile Ile Asp Val Ile Asp Lys Glu Leu Ile Gln Pro Phe
```

-continued

```
            340                 345                 350

Glu Ile Leu Phe Glu Gly Val Glu Tyr Ile Ala Arg Ala Gly Trp Thr
        355                 360                 365

Pro Glu Gly Lys Tyr Ala Trp Ser Ile Leu Leu Asp Arg Ser Gln Thr
    370                 375                 380

Arg Leu Gln Ile Val Leu Ile Ser Pro Glu Leu Phe Ile Pro Val Glu
385                 390                 395                 400

Asp Asp Val Met Glu Arg Gln Arg Leu Ile Glu Ser Val Pro Asp Ser
                405                 410                 415

Val Thr Pro Leu Ile Ile Tyr Glu Glu Thr Thr Asp Ile Trp Ile Asn
            420                 425                 430

Ile His Asp Ile Phe His Val Phe Pro Gln Ser His Glu Glu Glu Ile
        435                 440                 445

Glu Phe Ile Phe Ala Ser Glu Cys Lys Thr Gly Phe Arg His Leu Tyr
    450                 455                 460

Lys Ile Thr Ser Ile Leu Lys Glu Ser Lys Tyr Lys Arg Ser Ser Gly
465                 470                 475                 480

Gly Leu Pro Ala Pro Ser Asp Phe Lys Cys Pro Ile Lys Glu Glu Ile
                485                 490                 495

Ala Ile Thr Ser Gly Glu Trp Glu Val Leu Gly Arg His Gly Ser Asn
            500                 505                 510

Ile Gln Val Asp Glu Val Arg Arg Leu Val Tyr Phe Glu Gly Thr Lys
        515                 520                 525

Asp Ser Pro Leu Glu His His Leu Tyr Val Val Ser Tyr Val Asn Pro
    530                 535                 540

Gly Glu Val Thr Arg Leu Thr Asp Arg Gly Tyr Ser His Ser Cys Cys
545                 550                 555                 560

Ile Ser Gln His Cys Asp Phe Phe Ile Ser Lys Tyr Ser Asn Gln Lys
                565                 570                 575

Asn Pro His Cys Val Ser Leu Tyr Lys Leu Ser Ser Pro Glu Asp Asp
            580                 585                 590

Pro Thr Cys Lys Thr Lys Glu Phe Trp Ala Thr Ile Leu Asp Ser Ala
        595                 600                 605

Gly Pro Leu Pro Asp Tyr Thr Pro Pro Glu Ile Phe Ser Phe Glu Ser
    610                 615                 620

Thr Thr Gly Phe Thr Leu Tyr Gly Met Leu Tyr Lys Pro His Asp Leu
625                 630                 635                 640

Gln Pro Gly Lys Lys Tyr Pro Thr Val Leu Phe Ile Tyr Gly Gly Arg
                645                 650                 655

Val Lys


<210> SEQ ID NO 20
<211> LENGTH: 4676
<212> TYPE: DNA
<213> ORGANISM: Homo sapiens

<400> SEQUENCE: 20

aagtgctaaa gcctccgagg ccaaggccgc tgctactgcc gccgctgctt cttagtgccg      60

cgttcgccgc ctgggttgtc accggcgccg ccgccgagga agccactgca accaggaccg     120

gagtggaggc ggcgcagcat gaagcggcgc aggcccgctc catagcgcac gtcgggacgg     180

tccgggcggg gccgggggga aggaaaatgc aacatggcag cagcaatgga aacagaacag     240

ctgggtgttg agatatttga aactgcggac tgtgaggaga atattgaatc acaggatcgg     300
```

-continued

```
cctaaattgg agccttttta tgttgagcgg tattcctgga gtcagcttaa aaagctgctt    360
gccgatacca gaaaatatca tggctacatg atggctaagg caccacatga tttcatgttt    420
gtgaagagga atgatccaga tggacctcat tcagacagaa tctattacct tgccatgtct    480
ggtgagaaca gagaaaatac actgttttat tctgaaattc ccaaaactat caatagagca    540
gcagtcttaa tgctctcttg gaagcctctt ttggatcttt ttcaggcaac actggactat    600
ggaatgtatt ctcgagaaga agaactatta agagaaagaa aacgcattgg aacagtcgga    660
attgcttctt acgattatca ccaaggaagt ggaacatttc tgtttcaagc cggtagtgga    720
atttatcacg taaaagatgg agggccacaa ggatttacgc aacaaccttt aaggcccaat    780
ctagtggaaa ctagttgtcc caacatacgg atggatccaa aattatgccc tgctgatcca    840
gactggattg cttttataca tagcaacgat atttggatat ctaacatcgt aaccagagaa    900
gaaaggagac tcacttatgt gcacaatgag ctagccaaca tggaagaaga tgccagatca    960
gctggagtcg ctacctttgt tctccaagaa gaatttgata gatattctgg ctattggtgg   1020
tgtccaaaag ctgaaacaac tcccagtggt ggtaaaattc ttagaattct atatgaagaa   1080
aatgatgaat ctgaggtgga aattattcat gttacatccc ctatgttgga aacaaggagg   1140
gcagattcat tccgttatcc taaaacaggt acagcaaatc ctaaagtcac ttttaagatg   1200
tcagaaataa tgattgatgc tgaaggaagg atcatagatg tcatagataa ggaactaatt   1260
caacctttttg agattctatt tgaaggagtt gaatatattg ccagagctgg atggactcct   1320
gagggaaaat atgcttggtc catcctacta gatcgctccc agactcgcct acagatagtg   1380
ttgatctcac ctgaattatt tatcccagta gaagatgatg ttatggaaag gcagagactc   1440
attgagtcag tgcctgattc tgtgacgcca ctaattatct atgaagaaac aacagacatc   1500
tggataaata tccatgacat ctttcatgtt tttccccaaa gtcacgaaga ggaaattgag   1560
tttattttttg cctctgaatg caaaacaggt ttccgtcatt tatacaaaat tacatctatt   1620
ttaaaggaaa gcaaatataa acgatccagt ggtgggctgc ctgctccaag tgatttcaag   1680
tgtcctatca aagaggagat agcaattacc agtggtgaat gggaagttct tggccggcat   1740
ggatctaata tccaagttga tgaagtcaga aggctggtat attttgaagg caccaaagac   1800
tccccctttag agcatcacct gtacgtagtc agttacgtaa atcctggaga ggtgacaagg   1860
ctgactgacc gtggctactc acattcttgc tgcatcagtc agcactgtga cttctttata   1920
agtaagtata gtaaccagaa gaatccacac tgtgtgtccc tttacaagct atcaagtcct   1980
gaagatgacc caacttgcaa aacaaaggaa ttttgggcca ccattttgga ttcagcaggt   2040
cctcttcctg actatactcc tccagaaatt ttctcttttg aaagtactac tggatttaca   2100
ttgtatggga tgctctacaa gcctcatgat ctacagcctg gaaagaaata tcctactgtg   2160
ctgttcatat atggtggtcg ggtcaaatag aaattgacga tcaggtggaa ggactccaat   2220
atctagcttc tcgatatgat ttcattgact tagatcgtgt gggcatccac ggctggtcct   2280
atggaggata cctctccctg atggcattaa tgcagaggtc agatatcttc agggttgcta   2340
ttgctggggc cccagtcact ctgtggatct tctatgatac aggatacacg gaacgttata   2400
tgggtcaccc tgaccagaat gaacagggct attacttagg atctgtggcc atgcaagcag   2460
aaaagttccc ctctgaacca aatcgtttac tgctcttaca tggtttcctg gatgagaatg   2520
tccattttgc acataccagt atattactga gttttttagt gagggctgga aagccatatg   2580
atttacagat ctatcctcag gagagacaca gcataagagt tcctgaatcg ggagaacatt   2640
atgaactgca tcttttgcac taccttcaag aaaaccttgg atcacgtatt gctgctctaa   2700
```

-continued

```
aagtgatata attttgacct gtgtagaact ctctggtata cactggctat ttaaccaaat   2760
gaggaggttt aatcaacaga aaacacagaa ttgatcatca cattttgata cctgccatgt   2820
aacatctact cctgaaaata aatgtggtgc catgcagggg tctacggttt gtggtagtaa   2880
tctaatacct taaccccaca tgctcaaaat caaatgatac atattcctga gagacccagc   2940
aataccataa gaattactaa aaaaaaaaaa aaaaaaaaga cattagcacc atgtattcat   3000
actaccctat tttcactttt aatagtatta taaacttcat gaacttaatt agtgtatttt   3060
tacagtatac ttttgagttt gttaaaatat gatgatatta gtgattggtt tggttcagtt   3120
ccagaatctt tgactagtta cagatttgat agcacttaaa tgtaattgaa tagcttatgc   3180
ttcattgctt gggcatatcc agcatgttat gaactaataa ctattaaact tgacttaacc   3240
agtcattcat taataatttt tcaaggataa cttagtggcc tcctaaagac acttgttttg   3300
gcactgacca gtttttagcc aatttaatct gtatctagta taaataattc tcatttttct   3360
ttgatgatat taacagagtg ggcttttcct tttgcataaa ggctagtaac tgtatatgta   3420
gcatggattt aattagtcat gatattgata attacaggca gaaaattttt aatcaaatga   3480
ttagagctta aatatttgca ggcaagtttt tttttttcct ttaagaaaag gaaaaagtac   3540
acattcacta gaattcttca gaaaatttag tggtgccagt ttccatttgg tatttcctta   3600
ttaaaatatt ctagaatttt aaggagattg aagggaatca cagtggggtg gggagacctg   3660
ggtttgggga atgacagaga gaagaggtgg tgagggcctg attaaaaact aagcagaagt   3720
agttttaaca aaaatactca tgaaaatgtt tggaaactga aatttaaaca actgtaatat   3780
taaggaaacc agaatcaata aatcactgtc ttgccagcac agctacagag taacatgatt   3840
caggggagga aaagttcctt agagttactt ttataattct tttttttttt cctcttaggt   3900
ttagaaatct tacaaattta aactttatcc ttttaaaatt atttgaacat aatttagata   3960
ttgtaagctt aaaatacaaa tgtttataga taacctcttt accataaact aatccctggc   4020
aagccatggc tctctttttt tttttggtgt ttaaagcctg taaacagttt ttctgaatga   4080
tcatgaactt ttcttggttt agcactagga tttagctatg aagagagctc ataggctttc   4140
aggtgctaat tgagatctgc cctgttagag tcttggggtg ctagattggt cacattgaca   4200
ccagtggcag ggaaggcatc tatgagtttg atgcttttta tcacacactt cagtgtttag   4260
aaagttatta ccaatacttt taaacaacac tccaagaaaa tttgctatat ttctttctca   4320
tcactacaga gagagtagat ttccccatag agagcacagc ctccattagt aaggttggtg   4380
actattggta agaggtggac ttcattgaca ccaagtggga ggtagggaaa gcccagaaat   4440
ggcaggatga tatggtggtt ctgtcgttgg gaaaggtatt gggttttgct gtttgtattt   4500
atactgtata atagatacca cgctttttct tattatctgt atatgtattg cttttcatgt   4560
ttgatatttt cccatgccaa gatttgttta tatatatttt caatgttaaa ttaaattgat   4620
ttgggtaact ttcttcccca agaaagtatt ttccccctta agtataaatc tgactg        4676
```

```
<210> SEQ ID NO 21
<211> LENGTH: 613
<212> TYPE: PRT
<213> ORGANISM: Homo sapiens

<400> SEQUENCE: 21

Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
```

-continued

```
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Glu Asn Arg Glu Asn Thr
                85                  90                  95

Leu Phe Tyr Ser Glu Ile Pro Lys Thr Ile Asn Arg Ala Ala Val Leu
            100                 105                 110

Met Leu Ser Trp Lys Pro Leu Leu Asp Leu Phe Gln Ala Thr Leu Asp
        115                 120                 125

Tyr Gly Met Tyr Ser Arg Glu Glu Glu Leu Leu Arg Glu Arg Lys Arg
    130                 135                 140

Ile Gly Thr Val Gly Ile Ala Ser Tyr Asp Tyr His Gln Gly Ser Gly
145                 150                 155                 160

Thr Phe Leu Phe Gln Ala Gly Ser Gly Ile Tyr His Val Lys Asp Gly
                165                 170                 175

Gly Pro Gln Gly Phe Thr Gln Gln Pro Leu Arg Pro Asn Leu Val Glu
            180                 185                 190

Thr Ser Cys Pro Asn Ile Arg Met Asp Pro Lys Leu Cys Pro Ala Asp
        195                 200                 205

Pro Asp Trp Ile Ala Phe Ile His Ser Asn Asp Ile Trp Ile Ser Asn
    210                 215                 220

Ile Val Thr Arg Glu Glu Arg Arg Leu Thr Tyr Val His Asn Glu Leu
225                 230                 235                 240

Ala Asn Met Glu Glu Asp Ala Arg Ser Ala Gly Val Ala Thr Phe Val
                245                 250                 255

Leu Gln Glu Glu Phe Asp Arg Tyr Ser Gly Tyr Trp Trp Cys Pro Lys
            260                 265                 270

Ala Glu Thr Thr Pro Ser Gly Gly Lys Ile Leu Arg Ile Leu Tyr Glu
        275                 280                 285

Glu Asn Asp Glu Ser Glu Val Glu Ile Ile His Val Thr Ser Pro Met
    290                 295                 300

Leu Glu Thr Arg Arg Ala Asp Ser Phe Arg Tyr Pro Lys Thr Gly Thr
305                 310                 315                 320

Ala Asn Pro Lys Val Thr Phe Lys Met Ser Glu Ile Met Ile Asp Ala
                325                 330                 335

Glu Gly Arg Ile Ile Asp Val Ile Asp Lys Glu Leu Ile Gln Pro Phe
            340                 345                 350

Glu Ile Leu Phe Glu Gly Val Glu Tyr Ile Ala Arg Ala Gly Trp Thr
        355                 360                 365

Pro Glu Gly Lys Tyr Ala Trp Ser Ile Leu Leu Asp Arg Ser Gln Thr
    370                 375                 380

Arg Leu Gln Ile Val Leu Ile Ser Pro Glu Leu Phe Ile Pro Val Glu
385                 390                 395                 400

Asp Asp Val Met Glu Arg Gln Arg Leu Ile Glu Ser Val Pro Asp Ser
                405                 410                 415

Val Thr Pro Leu Ile Ile Tyr Glu Glu Thr Thr Asp Ile Trp Ile Asn
            420                 425                 430

Ile His Asp Ile Phe His Val Phe Pro Gln Ser His Glu Glu Glu Ile
        435                 440                 445
```

-continued

```
Glu Phe Ile Phe Ala Ser Glu Cys Lys Thr Gly Phe Arg His Leu Tyr
    450                 455                 460

Lys Ile Thr Ser Ile Leu Lys Glu Ser Lys Tyr Lys Arg Ser Ser Gly
465                 470                 475                 480

Gly Leu Pro Ala Pro Ser Asp Phe Lys Cys Pro Ile Lys Glu Glu Ile
                485                 490                 495

Ala Ile Thr Ser Gly Glu Trp Glu Val Leu Gly Arg His Gly Ser Asn
            500                 505                 510

Ile Gln Val Asp Glu Val Arg Arg Leu Val Tyr Phe Glu Gly Thr Lys
        515                 520                 525

Asp Ser Pro Leu Glu His His Leu Tyr Val Val Ser Tyr Val Asn Pro
    530                 535                 540

Gly Glu Val Thr Arg Leu Thr Asp Arg Gly Tyr Ser His Ser Cys Cys
545                 550                 555                 560

Ile Ser Gln His Cys Asp Phe Phe Ile Ser Lys Tyr Ser Asn Gln Lys
                565                 570                 575

Asn Pro His Cys Val Ser Leu Tyr Lys Leu Ser Ser Pro Glu Asp Asp
            580                 585                 590

Pro Thr Cys Lys Thr Lys Glu Phe Trp Ala Thr Ile Leu Asp Ser Val
        595                 600                 605

Leu Arg Cys Ser Trp
    610
```

```
<210> SEQ ID NO 22
<211> LENGTH: 4685
<212> TYPE: DNA
<213> ORGANISM: Homo sapiens

<400> SEQUENCE: 22

aagtgctaaa gcctccgagg ccaaggccgc tgctactgcc gccgctgctt cttagtgccg     60

cgttcgccgc ctgggttgtc accggcgccg ccgccgagga agccactgca accaggaccg    120

gagtggaggc ggcgcagcat gaagcggcgc aggcccgctc catagcgcac gtcgggacgg    180

tccgggcggg gccgggggga aggaaaatgc aacatggcag cagcaatgga aacagaacag    240

ctgggtgttg agatatttga aactgcggac tgtgaggaga atattgaatc acaggatcgg    300

cctaaattgg agcctttttta tgttgagcgg tattcctgga gtcagcttaa aaagctgctt    360

gccgatacca gaaaatatca tggctacatg atggctaagg caccacatga tttcatgttt    420

gtgaagagga atgatccaga tggacctcat tcagacagaa tctattacct tgccatgtct    480

ggtgagaaca gagaaaatac actgttttat tctgaaattc ccaaaactat caatagagca    540

gcagtcttaa tgctctcttg gaagcctctt ttggatcttt ttcaggcaac actggactat    600

ggaatgtatt ctcgagaaga agaactatta agagaaagaa aacgcattgg aacagtcgga    660

attgcttctt acgattatca ccaaggaagt ggaacatttc tgtttcaagc cggtagtgga    720

atttatcacg taaaagatgg agggccacaa ggatttacgc aacaaccttt aaggcccaat    780

ctagtggaaa ctagttgtcc caacatacgg atggatccaa aattatgccc tgctgatcca    840

gactggattg cttttataca tagcaacgat atttggatat ctaacatcgt aaccagagaa    900

gaaaggagac tcacttatgt gcacaatgag ctagccaaca tggaagaaga tgccagatca    960

gctggagtcg ctacctttgt tctccaagaa gaatttgata gatattctgg ctattggtgg   1020

tgtccaaaag ctgaaacaac tcccagtggt ggtaaaattc ttagaattct atatgaagaa   1080

aatgatgaat ctgaggtgga aattattcat gttacatccc ctatgttgga aacaaggagg   1140
```

-continued

```
gcagattcat tccgttatcc taaaacaggt acagcaaatc ctaaagtcac ttttaagatg   1200
tcagaaataa tgattgatgc tgaaggaagg atcatagatg tcatagataa ggaactaatt   1260
caacctttg agattctatt tgaaggagtt gaatatattg ccagagctgg atggactcct     1320
gagggaaaat atgcttggtc catcctacta gatcgctccc agactcgcct acagatagtg   1380
ttgatctcac ctgaattatt tatcccagta gaagatgatg ttatggaaag gcagagactc   1440
attgagtcag tgcctgattc tgtgacgcca ctaattatct atgaagaaac aacagacatc   1500
tggataaata tccatgacat ctttcatgtt tttccccaaa gtcacgaaga ggaaattgag   1560
tttattttg cctctgaatg caaaacaggt ttccgtcatt tatacaaaat tacatctatt     1620
ttaaaggaaa gcaaatataa acgatccagt ggtgggctgc ctgctccaag tgatttcaag   1680
tgtcctatca aagaggagat agcaattacc agtggtgaat gggaagttct tggccggcat   1740
ggatctaata tccaagttga tgaagtcaga aggctggtat attttgaagg caccaaagac   1800
tcccctttag agcatcacct gtacgtagtc agttacgtaa atcctggaga ggtgacaagg   1860
ctgactgacc gtggctactc acattcttgc tgcatcagtc agcactgtga cttctttata   1920
agtaagtata gtaaccagaa gaatccacac tgtgtgtccc tttacaagct atcaagtcct   1980
gaagatgacc caacttgcaa aacaaaggaa ttttgggcca ccattttgga ttcagtcctc   2040
aggtgcagtt ggtgaataat cggtttaaag gagtcaagta tttccgcttg aataccctag   2100
cctctctagg ttatgtggtt gtagtgatag acaacagggg atcctgtcac cgagggctta   2160
aatttgaagg cgcctttaaa tataaaatgg gtcaaataga aattgacgat caggtggaag   2220
gactccaata tctagcttct cgatatgatt tcattgactt agatcgtgtg ggcatccacg   2280
gctggtccta tggaggatac ctctccctga tggcattaat gcagaggtca gatatcttca   2340
gggttgctat tgctggggcc ccagtcactc tgtggatctt ctatgataca ggatacacgg   2400
aacgttatat gggtcaccct gaccagaatg aacagggcta ttacttagga tctgtggcca   2460
tgcaagcaga aaagttcccc tctgaaccaa atcgtttact gctcttacat ggtttcctgg   2520
atgagaatgt ccattttgca cataccagta tattactgag tttttagtg agggctggaa     2580
agccatatga tttacagatc tatcctcagg agagacacag cataagagtt cctgaatcgg   2640
gagaacatta tgaactgcat cttttgcact accttcaaga aaaccttgga tcacgtattg   2700
ctgctctaaa agtgatataa ttttgacctg tgtagaactc tctggtatac actggctatt   2760
taaccaaatg aggaggttta atcaacagaa aacacagaat tgatcatcac attttgatac   2820
ctgccatgta acatctactc ctgaaaataa atgtggtgcc atgcaggggt ctacggtttg   2880
tggtagtaat ctaatacctt aaccccacat gctcaaaatc aaatgataca tattcctgag   2940
agacccagca ataccataag aattactaaa aaaaaaaaaa aaaaaaagac attagcacca   3000
tgtattcata ctaccctatt ttcactttta atagtattat aaacttcatg aacttaatta   3060
gtgtattttt acagtatact tttgagtttg ttaaaatatg atgatattag tgattggttt   3120
ggttcagttc cagaatcttt gactagttac agatttgata gcacttaaat gtaattgaat   3180
agcttatgct tcattgcttg ggcatatcca gcatgttatg aactaataac tattaaactt   3240
gacttaacca gtcattcatt aataattttt caaggataac ttagtggcct cctaaagaca   3300
cttgttttgg cactgaccag tttttagcca atttaatctg tatctagtat aaataattct   3360
catttttctt tgatgatatt aacagagtgg gcttttcctt ttgcataaag gctagtaact   3420
gtatatgtag catggattta attagtcatg atattgataa ttacaggcag aaaattttta   3480
```

-continued

```
atcaaatgat tagagcttaa atatttgcag gcaagttttt ttttttcctt taagaaaagg   3540

aaaaagtaca cattcactag aattcttcag aaaatttagt ggtgccagtt tccatttggt   3600

atttccttat taaaatattc tagaatttta aggagattga agggaatcac agtggggtgg   3660

ggagacctgg gtttggggaa tgacagagag aagaggtggt gagggcctga ttaaaaacta   3720

agcagaagta gttttaacaa aaatactcat gaaaatgttt ggaaactgaa atttaaacaa   3780

ctgtaatatt aaggaaacca gaatcaataa atcactgtct tgccagcaca gctacagagt   3840

aacatgattc aggggaggaa aagttcctta gagttacttt tataattctt ttttttttc   3900

ctcttaggtt tagaaatctt acaaatttaa actttatcct tttaaaatta tttgaacata   3960

atttagatat tgtaagctta aaatacaaat gtttatagat aacctcttta ccataaacta   4020

atccctggca agccatggct ctcttttttt ttttggtgtt taaagcctgt aaacagtttt   4080

tctgaatgat catgaacttt tcttggttta gcactaggat ttagctatga agagagctca   4140

taggctttca ggtgctaatt gagatctgcc ctgttagagt cttggggtgc tagattggtc   4200

acattgacac cagtggcagg gaaggcatct atgagtttga tgctttttat cacacacttc   4260

agtgtttaga aagttattac caatactttt aaacaacact ccaagaaaat ttgctatatt   4320

tctttctcat cactacagag agagtagatt tccccataga gagcacagcc tccattagta   4380

aggttggtga ctattggtaa gaggtggact tcattgacac caagtgggag gtagggaaag   4440

cccagaaatg gcaggatgat atggtggttc tgtcgttggg aaaggtattg ggttttgctg   4500

tttgtattta tactgtataa tagataccac gctttttctt attatctgta tatgtattgc   4560

ttttcatgtt tgatattttc ccatgccaag atttgtttat atatattttc aatgttaaat   4620

taaattgatt tgggtaactt tcttccccaa gaaagtattt tcccccttaa gtataaatct   4680

gactg                                                               4685
```

<210> SEQ ID NO 23
<211> LENGTH: 892
<212> TYPE: PRT
<213> ORGANISM: Homo sapiens

<400> SEQUENCE: 23

```
Met Arg Lys Val Lys Lys Leu Arg Leu Asp Lys Glu Asn Thr Gly Ser
1               5                   10                  15

Trp Arg Ser Phe Ser Leu Asn Ser Glu Gly Ala Glu Arg Met Ala Thr
            20                  25                  30

Thr Gly Thr Pro Thr Ala Asp Arg Gly Asp Ala Ala Ala Thr Asp Asp
        35                  40                  45

Pro Ala Ala Arg Phe Gln Val Gln Lys His Ser Trp Asp Gly Leu Arg
    50                  55                  60

Ser Ile Ile His Gly Ser Arg Lys Tyr Ser Gly Leu Ile Val Asn Lys
65                  70                  75                  80

Ala Pro His Asp Phe Gln Phe Val Gln Lys Thr Asp Glu Ser Gly Pro
                85                  90                  95

His Ser His Arg Leu Tyr Tyr Leu Gly Met Pro Tyr Gly Ser Arg Glu
            100                 105                 110

Asn Ser Leu Leu Tyr Ser Glu Ile Pro Lys Lys Val Arg Lys Glu Ala
        115                 120                 125

Leu Leu Leu Leu Ser Trp Lys Gln Met Leu Asp His Phe Gln Ala Thr
    130                 135                 140

Pro His His Gly Val Tyr Ser Arg Glu Glu Glu Leu Leu Arg Glu Arg
145                 150                 155                 160
```

-continued

```
Lys Arg Leu Gly Val Phe Gly Ile Thr Ser Tyr Asp Phe His Ser Glu
                165                 170                 175

Ser Gly Leu Phe Leu Phe Gln Ala Ser Asn Ser Leu Phe His Cys Arg
            180                 185                 190

Asp Gly Gly Lys Asn Gly Phe Met Val Ser Pro Met Lys Pro Leu Glu
        195                 200                 205

Ile Lys Thr Gln Cys Ser Gly Pro Arg Met Asp Pro Lys Ile Cys Pro
    210                 215                 220

Ala Asp Pro Ala Phe Phe Ser Phe Ile Asn Asn Ser Asp Leu Trp Val
225                 230                 235                 240

Ala Asn Ile Glu Thr Gly Glu Glu Arg Arg Leu Thr Phe Cys His Gln
                245                 250                 255

Gly Leu Ser Asn Val Leu Asp Asp Pro Lys Ser Ala Gly Val Ala Thr
            260                 265                 270

Phe Val Ile Gln Glu Glu Phe Asp Arg Phe Thr Gly Tyr Trp Trp Cys
        275                 280                 285

Pro Thr Ala Ser Trp Glu Gly Ser Glu Gly Leu Lys Thr Leu Arg Ile
    290                 295                 300

Leu Tyr Glu Glu Val Asp Glu Ser Glu Val Glu Val Ile His Val Pro
305                 310                 315                 320

Ser Pro Ala Leu Glu Glu Arg Lys Thr Asp Ser Tyr Arg Tyr Pro Arg
                325                 330                 335

Thr Gly Ser Lys Asn Pro Lys Ile Ala Leu Lys Leu Ala Glu Phe Gln
            340                 345                 350

Thr Asp Ser Gln Gly Lys Ile Val Ser Thr Gln Glu Lys Glu Leu Val
        355                 360                 365

Gln Pro Phe Ser Ser Leu Phe Pro Lys Val Glu Tyr Ile Ala Arg Ala
    370                 375                 380

Gly Trp Thr Arg Asp Gly Lys Tyr Ala Trp Ala Met Phe Leu Asp Arg
385                 390                 395                 400

Pro Gln Gln Trp Leu Gln Leu Val Leu Leu Pro Pro Ala Leu Phe Ile
                405                 410                 415

Pro Ser Thr Glu Asn Glu Glu Gln Arg Leu Ala Ser Ala Arg Ala Val
            420                 425                 430

Pro Arg Asn Val Gln Pro Tyr Val Val Tyr Glu Glu Val Thr Asn Val
        435                 440                 445

Trp Ile Asn Val His Asp Ile Phe Tyr Pro Phe Pro Gln Ser Glu Gly
    450                 455                 460

Glu Asp Glu Leu Cys Phe Leu Arg Ala Asn Glu Cys Lys Thr Gly Phe
465                 470                 475                 480

Cys His Leu Tyr Lys Val Thr Ala Val Leu Lys Ser Gln Gly Tyr Asp
                485                 490                 495

Trp Ser Glu Pro Phe Ser Pro Gly Glu Asp Glu Phe Lys Cys Pro Ile
            500                 505                 510

Lys Glu Glu Ile Ala Leu Thr Ser Gly Glu Trp Glu Val Leu Ala Arg
        515                 520                 525

His Gly Ser Lys Ile Trp Val Asn Glu Glu Thr Lys Leu Val Tyr Phe
    530                 535                 540

Gln Gly Thr Lys Asp Thr Pro Leu Glu His His Leu Tyr Val Val Ser
545                 550                 555                 560

Tyr Glu Ala Ala Gly Glu Ile Val Arg Leu Thr Thr Pro Gly Phe Ser
                565                 570                 575
```

-continued

```
His Ser Cys Ser Met Ser Gln Asn Phe Asp Met Phe Val Ser His Tyr
            580                 585                 590

Ser Ser Val Ser Thr Pro Pro Cys Val His Val Tyr Lys Leu Ser Gly
        595                 600                 605

Pro Asp Asp Asp Pro Leu His Lys Gln Pro Arg Phe Trp Ala Ser Met
    610                 615                 620

Met Glu Ala Ala Ser Cys Pro Pro Asp Tyr Val Pro Pro Glu Ile Phe
625                 630                 635                 640

His Phe His Thr Arg Ser Asp Val Arg Leu Tyr Gly Met Ile Tyr Lys
                645                 650                 655

Pro His Ala Leu Gln Pro Gly Lys Lys His Pro Thr Val Leu Phe Val
            660                 665                 670

Tyr Gly Gly Pro Gln Val Gln Leu Val Asn Asn Ser Phe Lys Gly Ile
        675                 680                 685

Lys Tyr Leu Arg Leu Asn Thr Leu Ala Ser Leu Gly Tyr Ala Val Val
    690                 695                 700

Val Ile Asp Gly Arg Gly Ser Cys Gln Arg Gly Leu Arg Phe Glu Gly
705                 710                 715                 720

Ala Leu Lys Asn Gln Met Gly Gln Val Glu Ile Glu Asp Gln Val Glu
                725                 730                 735

Gly Leu Gln Phe Val Ala Glu Lys Tyr Gly Phe Ile Asp Leu Ser Arg
            740                 745                 750

Val Ala Ile His Gly Trp Ser Tyr Gly Gly Phe Leu Ser Leu Met Gly
        755                 760                 765

Leu Ile His Lys Pro Gln Val Phe Lys Val Ala Ile Ala Gly Ala Pro
    770                 775                 780

Val Thr Val Trp Met Ala Tyr Asp Thr Gly Tyr Thr Glu Arg Tyr Met
785                 790                 795                 800

Asp Val Pro Glu Asn Asn Gln His Gly Tyr Glu Ala Gly Ser Val Ala
                805                 810                 815

Leu His Val Glu Lys Leu Pro Asn Glu Pro Asn Arg Leu Leu Ile Leu
            820                 825                 830

His Gly Phe Leu Asp Glu Asn Val His Phe Phe His Thr Asn Phe Leu
        835                 840                 845

Val Ser Gln Leu Ile Arg Ala Gly Lys Pro Tyr Gln Leu Gln Ile Tyr
    850                 855                 860

Pro Asn Glu Arg His Ser Ile Arg Cys Pro Glu Ser Gly Glu His Tyr
865                 870                 875                 880

Glu Val Thr Leu Leu His Phe Leu Gln Glu Tyr Leu
                885                 890
```

<210> SEQ ID NO 24
<211> LENGTH: 4302
<212> TYPE: DNA
<213> ORGANISM: Homo sapiens

<400> SEQUENCE: 24

```
caggccgccg cctgggtcgc tcaacttccg ggtcaaaggt gcctgagccg gcgggtcccc     60

tgtgtccgcc gcggctgtcg tccccgctc ccgccacttc cggggtcgca gtcccgggca    120

tggagccgcg accgtgaggc gccgctggac ccgggacgac ctgcccagtc cggccgccgc    180

cccacgtccc ggtctgtgtc ccacgcctgc agctggaatg gaggctctct ggacccttta    240

gaaggcaccc ctgccctcct gaggtcagct gagcggttaa tgcggaaggt taagaaactg    300

cgcctggaca aggagaacac cggaagttgg agaagcttct cgctgaattc cgagggggct    360
```

-continued

```
gagaggatgg ccaccaccgg gaccccaacg gccgaccgag gcgacgcagc cgccacagat    420
gacccggccg cccgcttcca ggtgcagaag cactcgtggg acgggctccg gagcatcatc    480
cacggcagcc gcaagtactc gggcctcatt gtcaacaagg cgccccacga cttccagttt    540
gtgcagaaga cggatgagtc tgggccccac tcccaccgcc tctactacct gggaatgcca    600
tatggcagcc gagagaactc cctcctctac tctgagattc ccaagaaggt ccggaaagag    660
gctctgctgc tcctgtcctg gaagcagatg ctggatcatt tccaggccac gccccaccat    720
ggggtctact ctcgggagga ggagctgctg agggagcgga aacgcctggg ggtcttcggc    780
atcacctcct acgacttcca cagcgagagt ggcctcttcc tcttccaggc cagcaacagc    840
ctcttccact gccgcgacgg cggcaagaac ggcttcatgg tgtcccctat gaaaccgctg    900
gaaatcaaga cccagtgctc agggccccgg atggacccca aaatctgccc tgccgaccct    960
gccttcttct ccttcatcaa taacagcgac ctgtgggtgg ccaacatcga gacaggcgag   1020
gagcggcggc tgaccttctg ccaccaaggt ttatccaatg tcctggatga ccccaagtct   1080
gcgggtgtgg ccaccttcgt catacaggaa gagttcgacc gcttcactgg gtactggtgg   1140
tgccccacag cctcctggga aggttcagag ggcctcaaga cgctgcgaat cctgtatgag   1200
gaagtcgatg agtccgaggt ggaggtcatt cacgtcccct ctcctgcgct agaagaaagg   1260
aagacggact cgtatcggta ccccaggaca ggcagcaaga atcccaagat tgccttgaaa   1320
ctggctgagt tccagactga cagccagggc aagatcgtct cgacccagga gaaggagctg   1380
gtgcagccct tcagctcgct gttcccgaag gtggagtaca tcgccagggc cgggtggacc   1440
cgggatggca aatacgcctg ggccatgttc ctggaccggc cccagcagtg gctccagctc   1500
gtcctcctcc ccccggccct gttcatcccg agcacagaga atgaggagca gcggctagcc   1560
tctgccagag ctgtccccag gaatgtccag ccgtatgtgg tgtacgagga ggtcaccaac   1620
gtctggatca atgttcatga catcttctat cccttccccc aatcagaggg agaggacgag   1680
ctctgctttc tccgcgccaa tgaatgcaag accggcttct gccatttgta caaagtcacc   1740
gccgttttaa aatcccaggg ctacgattgg agtgagccct tcagccccgg ggaagatgaa   1800
tttaagtgcc ccattaagga agagattgct ctgaccagcg gtgaatggga ggttttggcg   1860
aggcacggct ccaagatctg ggtcaatgag gagaccaagc tggtgtactt ccagggcacc   1920
aaggacacgc cgctggagca ccacctctac gtggtcagct atgaggcggc cggcgagatc   1980
gtacgcctca ccacgcccgg cttctcccat agctgctcca tgagccagaa cttcgacatg   2040
ttcgtcagcc actacagcag cgtgagcacg ccgccctgcg tgcacgtcta caagctgagc   2100
ggccccgacg acgacccccct gcacaagcag ccccgcttct gggctagcat gatggaggca   2160
gccagctgcc ccccggatta tgttcctcca gagatcttcc atttccacac gcgctcggat   2220
gtgcggctct acggcatgat ctacaagccc cacgccttgc agccagggaa gaagcacccc   2280
accgtcctct ttgtatatgg aggcccccag gtgcagctgg tgaataactc cttcaaaggc   2340
atcaagtact tgcggctcaa cacactggcc tccctgggct acgccgtggt tgtgattgac   2400
ggcaggggct cctgtcagcg agggcttcgg ttcgaagggg ccctgaaaaa ccaaatgggc   2460
caggtggaga tcgaggacca ggtggagggc ctgcagttcg tggccgagaa gtatggcttc   2520
atcgacctga gccgagttgc catccatggc tggtcctacg gggggcttcct ctcgctcatg   2580
gggctaatcc acaagcccca ggtgttcaag gtggccatcg cgggtgcccc ggtcaccgtc   2640
tggatggcct acgacacagg gtacactgag cgctacatgg acgtccctga gaacaaccag   2700
```

-continued

```
cacggctatg aggcgggttc cgtggccctg cacgtggaga agctgcccaa tgagcccaac   2760

cgcttgctta tcctccacgg cttcctggac gaaaacgtgc actttttcca cacaaacttc   2820

ctcgtctccc aactgatccg agcagggaaa ccttaccagc tccagatcta ccccaacgag   2880

agacacagta ttcgctgccc cgagtcgggc gagcactatg aagtcacgtt gctgcacttt   2940

ctacaggaat acctctgagc ctgcccaccg ggagccgcca catcacagca caagtggctg   3000

cagcctccgc ggggaaccag gcgggaggga ctgagtggcc cgcgggcccc agtgaggcac   3060

tttgtcccgc ccagcgctgg ccagccccga ggagccgctg ccttcaccgc cccgacgcct   3120

tttatccttt tttaaacgct cttgggtttt atgtccgctg cttcttggtt gccgagacag   3180

agagatggtg gtctcgggcc agcccctcct ctccccgcct tctgggagga ggaggtcaca   3240

cgctgatggg cactggagag gccagaagag actcagagga gcgggctgcc ttccgcctgg   3300

ggctccctgt gacctctcag tcccctggcc cggccagcca ccgtccccag cacccaagca   3360

tgcaattgcc tgtccccccc ggccagcctc cccaacttga tgtttgtgtt ttgtttgggg   3420

ggatattttt cataattatt taaaagacag gccgggcgcg gtggctcacg tctgtaatcc   3480

cagcactttg ggaggctgag gcgggcggat cacctgaggt tgggagttca agaccagcct   3540

ggccaacatg gggaaacccc gtctctacta aaaatacaaa aaattagccg ggtgtggtgg   3600

cgcgtgccta taatcccagc tactcgggag gctgaggcag gagaatcgct tgaacccggg   3660

aggtggaggt tgcggtgagc caagatcgca ccattgcact ccagcctggg caacaagagc   3720

gaaactctgt ctcaaaataa ataaaaaata aaagacagaa agcaaggggt gcctaaatct   3780

agacttgggg tccacaccgg gcagcggggt tgcaacccag cacctggtag gctccatttc   3840

ttcccaagcc cgagcagagg gtcatgcggg ccccacagga gaagcggcca gggcccgcgg   3900

ggggcaccac ctgtggacag ccctcctgtc cccaagcttt caggcaggca ctgaaacgca   3960

ccgaacttcc acgctctgct ggtcagtggc ggctgtcccc tccccagccc agccgcccag   4020

ccacatgtgt ctgcctgacc cgtacacacc aggggttccg gggttgggag ctgaaccatc   4080

cccacctcag ggttatattt ccctctcccc ttccctcccc gccaagagct ctgccagggg   4140

cgggcaaaaa aaaaagtaaa aagaaaagaa aaaaaaaaaa aagaaacaaa ccacctctac   4200

atattatgga aagaaaatat ttttgtcgat tcttattctt ttataattat gcgtggaaga   4260

agtagacaca ttaaacgatt ccagttggaa acatgtcacc tg                      4302
```

```
<210> SEQ ID NO 25
<211> LENGTH: 518
<212> TYPE: PRT
<213> ORGANISM: Homo sapiens

<400> SEQUENCE: 25

Met Arg Lys Val Lys Lys Leu Arg Leu Asp Lys Glu Asn Thr Gly Ser
1               5                   10                  15

Trp Arg Ser Phe Ser Leu Asn Ser Glu Gly Ala Glu Arg Met Ala Thr
            20                  25                  30

Thr Gly Thr Pro Thr Ala Asp Arg Gly Asp Ala Ala Ala Thr Asp Asp
        35                  40                  45

Pro Ala Ala Arg Phe Gln Val Gln Lys His Ser Trp Asp Gly Leu Arg
    50                  55                  60

Ser Ile Ile His Gly Ser Arg Lys Tyr Ser Gly Leu Ile Val Asn Lys
65                  70                  75                  80

Ala Pro His Asp Phe Gln Phe Val Gln Lys Thr Asp Glu Ser Gly Pro
                85                  90                  95
```

-continued

```
His Ser His Arg Leu Tyr Tyr Leu Gly Met Pro Tyr Gly Ser Arg Glu
            100                 105                 110

Asn Ser Leu Leu Tyr Ser Glu Ile Pro Lys Lys Val Arg Lys Glu Ala
        115                 120                 125

Leu Leu Leu Leu Ser Trp Lys Gln Met Leu Asp His Phe Gln Ala Thr
    130                 135                 140

Pro His His Gly Val Tyr Ser Arg Glu Glu Glu Leu Leu Arg Glu Arg
145                 150                 155                 160

Lys Arg Leu Gly Val Phe Gly Ile Thr Ser Tyr Asp Phe His Ser Glu
                165                 170                 175

Ser Gly Leu Phe Leu Phe Gln Ala Ser Asn Ser Leu Phe His Cys Arg
            180                 185                 190

Asp Gly Gly Lys Asn Gly Phe Met Val Ser Pro Met Lys Pro Leu Glu
        195                 200                 205

Ile Lys Thr Gln Cys Ser Gly Pro Arg Met Asp Pro Lys Ile Cys Pro
    210                 215                 220

Ala Asp Pro Ala Phe Phe Ser Phe Ile Asn Asn Ser Asp Leu Trp Val
225                 230                 235                 240

Ala Asn Ile Glu Thr Gly Glu Glu Arg Arg Leu Thr Phe Cys His Gln
                245                 250                 255

Gly Leu Ser Asn Val Leu Asp Asp Pro Lys Ser Ala Gly Val Ala Thr
            260                 265                 270

Phe Val Ile Gln Glu Glu Phe Asp Arg Phe Thr Gly Tyr Trp Trp Cys
        275                 280                 285

Pro Thr Ala Ser Trp Glu Gly Ser Glu Gly Leu Lys Thr Leu Arg Ile
    290                 295                 300

Leu Tyr Glu Glu Val Asp Glu Ser Glu Val Glu Val Ile His Val Pro
305                 310                 315                 320

Ser Pro Ala Leu Glu Glu Arg Lys Thr Asp Ser Tyr Arg Tyr Pro Arg
                325                 330                 335

Thr Gly Ser Lys Asn Pro Lys Ile Ala Leu Lys Leu Ala Glu Phe Gln
            340                 345                 350

Thr Asp Ser Gln Gly Lys Ile Val Ser Thr Gln Glu Lys Glu Leu Val
        355                 360                 365

Gln Pro Phe Ser Ser Leu Phe Pro Lys Val Glu Tyr Ile Ala Arg Ala
    370                 375                 380

Gly Trp Thr Arg Asp Gly Lys Tyr Ala Trp Ala Met Phe Leu Asp Arg
385                 390                 395                 400

Pro Gln Gln Trp Leu Gln Leu Val Leu Leu Pro Pro Ala Leu Phe Ile
                405                 410                 415

Pro Ser Thr Glu Asn Glu Glu Gln Arg Leu Ala Ser Ala Arg Ala Val
            420                 425                 430

Pro Arg Asn Val Gln Pro Tyr Val Val Tyr Glu Glu Val Thr Asn Val
        435                 440                 445

Trp Ile Asn Val His Asp Ile Phe Tyr Pro Phe Pro Gln Ser Glu Gly
    450                 455                 460

Glu Asp Glu Leu Cys Phe Leu Arg Ala Asn Glu Cys Lys Thr Gly Phe
465                 470                 475                 480

Cys His Leu Tyr Lys Val Thr Ala Val Leu Lys Ser Gln Gly Tyr Asp
                485                 490                 495

Trp Ser Glu Pro Phe Ser Pro Gly Glu Gly Glu Gln Ser Leu Thr Asn
            500                 505                 510
```

-continued

Ala Val Asp Ser Ser Arg
515

<210> SEQ ID NO 26
<211> LENGTH: 2411
<212> TYPE: DNA
<213> ORGANISM: Homo sapiens

<400> SEQUENCE: 26
caggccgccg cctgggtcgc tcaacttccg ggtcaaaggt gcctgagccg gcgggtcccc 60
tgtgtccgcc gcggctgtcg tcccccgctc ccgccacttc cggggtcgca gtcccgggca 120
tggagccgcg accgtgaggc gccgctggac ccgggacgac ctgcccagtc cggccgccgc 180
cccacgtccc ggtctgtgtc ccacgcctgc agctggaatg gaggctctct ggaccccttta 240 gaaggcaccc ctgccctcct gaggtcagct gagcggttaa tgcggaaggt taagaaactg 300
cgcctggaca aggagaacac cggaagttgg agaagcttct cgctgaattc cgagggggct 360
gagaggatgg ccaccaccgg gaccccaacg gccgaccgag gcgacgcagc cgccacagat 420
gacccggccg cccgcttcca ggtgcagaag cactcgtggg acgggctccg gagcatcatc 480
cacggcagcc gcaagtactc gggcctcatt gtcaacaagg cgccccacga cttccagttt 540
gtgcagaaga cggatgagtc tgggccccac tcccaccgcc tctactacct gggaatgcca 600
tatggcagcc gagagaactc cctcctctac tctgagattc ccaagaaggt ccggaaagag 660
gctctgctgc tcctgtcctg gaagcagatg ctggatcatt tccaggccac gccccaccat 720
ggggtctact ctcgggagga ggagctgctg agggagcgga aacgcctggg ggtcttcggc 780
atcacctcct acgacttcca cagcgagagt ggcctcttcc tcttccaggc cagcaacagc 840
ctcttccact gccgcgacgg cggcaagaac ggcttcatgg tgtcccctat gaaaccgctg 900
gaaatcaaga cccagtgctc agggccccgg atggacccca aaatctgccc tgccgaccct 960
gccttcttct ccttcatcaa taacagcgac ctgtgggtgg ccaacatcga gacaggcgag 1020
gagcggcggc tgaccttctg ccaccaaggt ttatccaatg tcctggatga ccccaagtct 1080
gcgggtgtgg ccaccttcgt catacaggaa gagttcgacc gcttcactgg gtactggtgg 1140
tgccccacag cctcctggga aggttcagag ggcctcaaga cgctgcgaat cctgtatgag 1200
gaagtcgatg agtccgaggt ggaggtcatt cacgtcccct ctcctgcgct agaagaaagg 1260
aagacggact cgtatcggta ccccaggaca ggcagcaaga atcccaagat tgccttgaaa 1320
ctggctgagt tccagactga cagccagggc aagatcgtct cgacccagga gaaggagctg 1380
gtgcagccct tcagctcgct gttcccgaag gtggagtaca tcgccagggc cgggtggacc 1440
cgggatggca aatacgcctg ggccatgttc ctggaccggc cccagcagtg gctccagctc 1500
gtcctcctcc ccccggccct gttcatcccg agcacagaga atgaggagca gcggctagcc 1560
tctgccagag ctgtccccag gaatgtccag ccgtatgtgg tgtacgagga ggtcaccaac 1620
gtctggatca atgttcatga catcttctat cccttccccc aatcagaggg agaggacgag 1680
ctctgctttc tccgcgccaa tgaatgcaag accggcttct gccatttgta caaagtcacc 1740
gccgttttaa aatcccaggg ctacgattgg agtgagccct tcagccccgg ggaaggtgag 1800
cagagcctga cgaatgctgt cgactcatcg cgttagtcac gtgtggttca atatgctgtt 1860
tgttcattgg tcggcccccc cactcagcca gcacaccctg cgggagaagg aacagggatc 1920
ggcaggaagc cagccttccc cagtgactgc atgatctggc agggcttaga gcacccaact 1980
gttggcttat tcaggcagca gatttactga gcacctcccc tgtgccaggc ccttagcaca 2040

-continued

```
accaggggtt ggccacctac ggcccacagg tcaaatccgg cccaccacct gtgttcataa   2100

ataaagtttt attggcactg agccacagcc acttgtttac agagactgtc tgtggtcgct   2160

tttgtgctgc agcagcagaa ctgggtagtc ccagcagaaa ctgttgtgca aggccaagat   2220

ttactgtcta gccctttgta gaaacatttg ccagctcctg ctgtaggtag ctgtgatgga   2280

attgttcact gtaaataaag aaaaaggaaa atccctgctc ttgggacctt ctagtggagg   2340

aggcagtatt ccagaaacag ttagaggtgc tgcctctggt gtgctgtggg tggcagatgc   2400

agatcctagt c                                                        2411
```

```
<210> SEQ ID NO 27
<211> LENGTH: 892
<212> TYPE: PRT
<213> ORGANISM: Homo sapiens

<400> SEQUENCE: 27

Met Arg Lys Val Lys Lys Leu Arg Leu Asp Lys Glu Asn Thr Gly Ser
1               5                   10                  15

Trp Arg Ser Phe Ser Leu Asn Ser Glu Gly Ala Glu Arg Met Ala Thr
            20                  25                  30

Thr Gly Thr Pro Thr Ala Asp Arg Gly Asp Ala Ala Ala Thr Asp Asp
        35                  40                  45

Pro Ala Ala Arg Phe Gln Val Gln Lys His Ser Trp Asp Gly Leu Arg
    50                  55                  60

Ser Ile Ile His Gly Ser Arg Lys Tyr Ser Gly Leu Ile Val Asn Lys
65                  70                  75                  80

Ala Pro His Asp Phe Gln Phe Val Gln Lys Thr Asp Glu Ser Gly Pro
                85                  90                  95

His Ser His Arg Leu Tyr Tyr Leu Gly Met Pro Tyr Gly Ser Arg Glu
            100                 105                 110

Asn Ser Leu Leu Tyr Ser Glu Ile Pro Lys Lys Val Arg Lys Glu Ala
        115                 120                 125

Leu Leu Leu Leu Ser Trp Lys Gln Met Leu Asp His Phe Gln Ala Thr
    130                 135                 140

Pro His His Gly Val Tyr Ser Arg Glu Glu Glu Leu Leu Arg Glu Arg
145                 150                 155                 160

Lys Arg Leu Gly Val Phe Gly Ile Thr Ser Tyr Asp Phe His Ser Glu
                165                 170                 175

Ser Gly Leu Phe Leu Phe Gln Ala Ser Asn Ser Leu Phe His Cys Arg
            180                 185                 190

Asp Gly Gly Lys Asn Gly Phe Met Val Ser Pro Met Lys Pro Leu Glu
        195                 200                 205

Ile Lys Thr Gln Cys Ser Gly Pro Arg Met Asp Pro Lys Ile Cys Pro
    210                 215                 220

Ala Asp Pro Ala Phe Phe Ser Phe Ile Asn Asn Ser Asp Leu Trp Val
225                 230                 235                 240

Ala Asn Ile Glu Thr Gly Glu Glu Arg Arg Leu Thr Phe Cys His Gln
                245                 250                 255

Gly Leu Ser Asn Val Leu Asp Asp Pro Lys Ser Ala Gly Val Ala Thr
            260                 265                 270

Phe Val Ile Gln Glu Glu Phe Asp Arg Phe Thr Gly Tyr Trp Trp Cys
        275                 280                 285

Pro Thr Ala Ser Trp Glu Gly Ser Glu Gly Leu Lys Thr Leu Arg Ile
    290                 295                 300
```

-continued

Leu Tyr Glu Glu Val Asp Glu Ser Glu Val Glu Val Ile His Val Pro
305 310 315 320

Ser Pro Ala Leu Glu Glu Arg Lys Thr Asp Ser Tyr Arg Tyr Pro Arg
325 330 335

Thr Gly Ser Lys Asn Pro Lys Ile Ala Leu Lys Leu Ala Glu Phe Gln
340 345 350

Thr Asp Ser Gln Gly Lys Ile Val Ser Thr Gln Glu Lys Glu Leu Val
355 360 365

Gln Pro Phe Ser Ser Leu Phe Pro Lys Val Glu Tyr Ile Ala Arg Ala
370 375 380

Gly Trp Thr Arg Asp Gly Lys Tyr Ala Trp Ala Met Phe Leu Asp Arg
385 390 395 400

Pro Gln Gln Trp Leu Gln Leu Val Leu Leu Pro Pro Ala Leu Phe Ile
405 410 415

Pro Ser Thr Glu Asn Glu Glu Gln Arg Leu Ala Ser Ala Arg Ala Val
420 425 430

Pro Arg Asn Val Gln Pro Tyr Val Val Tyr Glu Glu Val Thr Asn Val
435 440 445

Trp Ile Asn Val His Asp Ile Phe Tyr Pro Phe Pro Gln Ser Glu Gly
450 455 460

Glu Asp Glu Leu Cys Phe Leu Arg Ala Asn Glu Cys Lys Thr Gly Phe
465 470 475 480

Cys His Leu Tyr Lys Val Thr Ala Val Leu Lys Ser Gln Gly Tyr Asp
485 490 495

Trp Ser Glu Pro Phe Ser Pro Gly Glu Asp Glu Phe Lys Cys Pro Ile
500 505 510

Lys Glu Glu Ile Ala Leu Thr Ser Gly Glu Trp Glu Val Leu Ala Arg
515 520 525

His Gly Ser Lys Ile Trp Val Asn Glu Glu Thr Lys Leu Val Tyr Phe
530 535 540

Gln Gly Thr Lys Asp Thr Pro Leu Glu His His Leu Tyr Val Val Ser
545 550 555 560

Tyr Glu Ala Ala Gly Glu Ile Val Arg Leu Thr Thr Pro Gly Phe Ser
565 570 575

His Ser Cys Ser Met Ser Gln Asn Phe Asp Met Phe Val Ser His Tyr
580 585 590

Ser Ser Val Ser Thr Pro Pro Cys Val His Val Tyr Lys Leu Ser Gly
595 600 605

Pro Asp Asp Asp Pro Leu His Lys Gln Pro Arg Phe Trp Ala Ser Met
610 615 620

Met Glu Ala Ala Ser Cys Pro Pro Asp Tyr Val Pro Pro Glu Ile Phe
625 630 635 640

His Phe His Thr Arg Ser Asp Val Arg Leu Tyr Gly Met Ile Tyr Lys
645 650 655

Pro His Ala Leu Gln Pro Gly Lys Lys His Pro Thr Val Leu Phe Val
660 665 670

Tyr Gly Gly Pro Gln Val Gln Leu Val Asn Asn Ser Phe Lys Gly Ile
675 680 685

Lys Tyr Leu Arg Leu Asn Thr Leu Ala Ser Leu Gly Tyr Ala Val Val
690 695 700

Val Ile Asp Gly Arg Gly Ser Cys Gln Arg Gly Leu Arg Phe Glu Gly
705 710 715 720

Ala Leu Lys Asn Gln Met Gly Gln Val Glu Ile Glu Asp Gln Val Glu

-continued

```
                725                 730                 735

Gly Leu Gln Phe Val Ala Glu Lys Tyr Gly Phe Ile Asp Leu Ser Arg
            740                 745                 750

Val Ala Ile His Gly Trp Ser Tyr Gly Gly Phe Leu Ser Leu Met Gly
        755                 760                 765

Leu Ile His Lys Pro Gln Val Phe Lys Val Ala Ile Ala Gly Ala Pro
    770                 775                 780

Val Thr Val Trp Met Ala Tyr Asp Thr Gly Tyr Thr Glu Arg Tyr Met
785                 790                 795                 800

Asp Val Pro Glu Asn Asn Gln His Gly Tyr Glu Ala Gly Ser Val Ala
                805                 810                 815

Leu His Val Glu Lys Leu Pro Asn Glu Pro Asn Arg Leu Leu Ile Leu
            820                 825                 830

His Gly Phe Leu Asp Glu Asn Val His Phe Phe His Thr Asn Phe Leu
        835                 840                 845

Val Ser Gln Leu Ile Arg Ala Gly Lys Pro Tyr Gln Leu Gln Ile Tyr
    850                 855                 860

Pro Asn Glu Arg His Ser Ile Arg Cys Pro Glu Ser Gly Glu His Tyr
865                 870                 875                 880

Glu Val Thr Leu Leu His Phe Leu Gln Glu Tyr Leu
                885                 890


<210> SEQ ID NO 28
<211> LENGTH: 4219
<212> TYPE: DNA
<213> ORGANISM: Homo sapiens

<400> SEQUENCE: 28

caggccgccg cctgggtcgc tcaacttccg ggtcaaaggt gcctgagccg gcgggtcccc     60

tgtgtccgcc gcggctgtcg tccccgctc ccgccacttc cggggtcgca gtcccgggca    120

tggagccgcg accgtgaggc gccgctggac ccgggacgac ctgcccagtc cggccgccgc    180

cccacgtccc ggtctgtgtc ccacgcctgc agctggaatg gaggctctct ggaccctta    240

gaaggcaccc ctgccctcct gaggtcagct gagcggttaa tgcggaaggt taagaaactg    300

cgcctggaca aggagaacac cggaagttgg agaagcttct cgctgaattc cgagggggct    360

gagaggatgg ccaccaccgg gaccccaacg gccgaccgag gcgacgcagc cgccacagat    420

gacccggccg cccgcttcca ggtgcagaag cactcgtggg acgggctccg gagcatcatc    480

cacggcagcc gcaagtactc gggcctcatt gtcaacaagg cgccccacga cttccagttt    540

gtgcagaaga cggatgagtc tgggccccac tcccaccgcc tctactacct gggaatgcca    600

tatggcagcc gagagaactc cctcctctac tctgagattc ccaagaaggt ccggaaagag    660

gctctgctgc tcctgtcctg gaagcagatg ctggatcatt tccaggccac gccccaccat    720

ggggtctact ctcgggagga ggagctgctg agggagcgga aacgcctggg ggtcttcggc    780

atcacctcct acgacttcca cagcgagagt ggcctcttcc tcttccaggc cagcaacagc    840

ctcttccact gccgcgacgg cggcaagaac ggcttcatgg tgtcccctat gaaaccgctg    900

gaaatcaaga cccagtgctc agggccccgg atggacccca aaatctgccc tgccgaccct    960

gccttcttct ccttcatcaa taacagcgac ctgtgggtgg ccaacatcga gacaggcgag   1020

gagcggcggc tgaccttctg ccaccaaggt ttatccaatg tcctggatga ccccaagtct   1080

gcgggtgtgg ccaccttcgt catacaggaa gagttcgacc gcttcactgg gtactggtgg   1140

tgccccacag cctcctggga aggttcagag ggcctcaaga cgctgcgaat cctgtatgag   1200
```

-continued gaagtcgatg agtccgaggt ggaggtcatt cacgtcccct ctcctgcgct agaagaaagg 1260
aagacggact cgtatcggta ccccaggaca ggcagcaaga atcccaagat tgccttgaaa 1320
ctggctgagt tccagactga cagccagggc aagatcgtct cgacccagga gaaggagctg 1380
gtgcagccct tcagctcgct gttcccgaag gtggagtaca tcgccagggc cgggtggacc 1440
cgggatggca aatacgcctg ggccatgttc ctggaccggc cccagcagtg gctccagctc 1500
gtcctcctcc ccccggccct gttcatcccg agcacagaga atgaggagca gcggctagcc 1560
tctgccagag ctgtccccag gaatgtccag ccgtatgtgg tgtacgagga ggtcaccaac 1620
gtctggatca atgttcatga catcttctat cccttccccc aatcagaggg agaggacgag 1680
ctctgctttc tccgcgccaa tgaatgcaag accggcttct gccatttgta caaagtcacc 1740
gccgttttaa aatcccaggg ctacgattgg agtgagccct tcagccccgg ggaagatgaa 1800
tttaagtgcc ccattaagga agagattgct ctgaccagcg gtgaatggga ggttttggcg 1860
aggcacggct ccaagatctg ggtcaatgag gagaccaagc tggtgtactt ccagggcacc 1920
aaggacacgc cgctggagca ccacctctac gtggtcagct atgaggcggc cggcgagatc 1980
gtacgcctca ccacgcccgg cttctcccat agctgctcca tgagccagaa cttcgacatg 2040
ttcgtcagcc actacagcag cgtgagcacg ccgccctgcg tgcacgtcta caagctgagc 2100
ggccccgacg acgacccct gcacaagcag ccccgcttct gggctagcat gatggaggca 2160
gccagctgcc ccccggatta tgttcctcca gagatcttcc atttccacac gcgctcggat 2220
gtgcggctct acggcatgat ctacaagccc cacgccttgc agccagggaa gaagcacccc 2280
accgtcctct ttgtatatgg aggcccccag gtgcagctgg tgaataactc cttcaaaggc 2340
atcaagtact tgcggctcaa cacactggcc tccctgggct acgccgtggt tgtgattgac 2400
ggcaggggct cctgtcagcg agggcttcgg ttcgaagggg ccctgaaaaa ccaaatgggc 2460
caggtggaga tcgaggacca ggtggagggc ctgcagttcg tggccgagaa gtatggcttc 2520
atcgacctga gccgagttgc catccatggc tggtcctacg gggcttcct ctcgctcatg 2580
gggctaatcc acaagcccca ggtgttcaag gtggccatcg cgggtgcccc ggtcaccgtc 2640
tggatggcct acgacacagg gtacactgag cgctacatgg acgtccctga gaacaaccag 2700
cacggctatg aggcgggttc cgtggccctg cacgtggaga agctgcccaa tgagcccaac 2760
cgcttgctta tcctccacgg cttcctggac gaaaacgtgc actttttcca cacaaacttc 2820
ctcgtctccc aactgatccg agcagggaaa ccttaccagc tccagatcta ccccaacgag 2880
agacacagta ttcgctgccc cgagtcgggc gagcactatg aagtcacgtt gctgcacttt 2940
ctacaggaat acctctgagc ctgcccaccg ggagccgcca catcacagca caagtggctg 3000
cagcctccgc ggggaaccag gcgggaggga ctgagtggcc cgcgggcccc agtgaggcac 3060
tttgtcccgc ccagcgctgg ccagccccga ggagccgctg ccttcaccgc cccgacgcct 3120
tttatccttt tttaaacgct cttgggtttt atgtccgctg cttcttggtt gccgagacag 3180
agagatggtg gtctcgggcc agcccctcct ctccccgcct tctgggagga ggaggtcaca 3240
cgctgatggg cactggagag gccagaagag actcagagga gcgggctgcc ttccgcctgg 3300
ggctccctgt gacctctcag tcccctggcc cggccagcca ccgtccccag cacccaagca 3360
tgcaattgcc tgtccccccc ggccagcctc cccaacttga tgtttgtgtt ttgtttgggg 3420
ggatattttt cataattatt taaaagacag gccgggcgcg gtggctcacg tctgtaatcc 3480
cagcactttg ggaggctgag gcgggcggat cacctgaggt tgggagttca agaccagcct 3540

-continued

```
ggccaacatg gggaaacccc gtctctacta aaaatacaaa aaattagccg ggtgtggtgg   3600

cgcgtgccta taatcccagc tactcgggag gctgaggcag gagaatcgct tgaacccggg   3660

aggtggaggt tgcggtgagc caagatcgca ccattgcact ccagcctggg caacaagagc   3720

gaaactctgt ctcaaaataa ataaaaaata aaagacagaa agcaaggggt gcctaaatct   3780

agacttgggg tccacaccgg gcagcggggt tgcaacccag cacctggtag gctccatttc   3840

ttcccaagcc cgactttcag gcaggcactg aaacgcaccg aacttccacg ctctgctggt   3900

cagtggcggc tgtcccctcc ccagcccagc cgcccagcca catgtgtctg cctgacccgt   3960

acacaccagg ggttccgggg ttgggagctg aaccatcccc acctcagggt tatatttccc   4020

tctcccottc cctccccgcc aagagctctg ccaggggcgg gcaaaaaaaa aagtaaaaag   4080

aaaagaaaaa aaaaaaaaag aaacaaacca cctctacata ttatggaaag aaaatatttt   4140

tgtcgattct tattctttta taattatgcg tggaagaagt agacacatta aacgattcca   4200

gttggaaaca tgtcacctg                                                4219


<210> SEQ ID NO 29
<211> LENGTH: 832
<212> TYPE: PRT
<213> ORGANISM: Homo sapiens

<400> SEQUENCE: 29

Met Arg Lys Val Lys Lys Leu Arg Leu Asp Lys Glu Asn Thr Gly Ser
1               5                   10                  15

Trp Arg Ser Phe Ser Leu Asn Ser Glu Gly Ala Glu Arg Met Ala Thr
            20                  25                  30

Thr Gly Thr Pro Thr Ala Asp Arg Gly Asp Ala Ala Ala Thr Asp Asp
        35                  40                  45

Pro Ala Ala Arg Phe Gln Val Gln Lys His Ser Trp Asp Gly Leu Arg
    50                  55                  60

Ser Ile Ile His Gly Ser Arg Lys Tyr Ser Gly Leu Ile Val Asn Lys
65                  70                  75                  80

Ala Pro His Asp Phe Gln Phe Val Gln Lys Thr Asp Glu Ser Gly Pro
                85                  90                  95

His Ser His Arg Leu Tyr Tyr Leu Gly Met Pro Tyr Gly Ser Arg Glu
            100                 105                 110

Asn Ser Leu Leu Tyr Ser Glu Ile Pro Lys Lys Val Arg Lys Glu Ala
        115                 120                 125

Leu Leu Leu Leu Ser Trp Lys Gln Met Leu Asp His Phe Gln Ala Thr
    130                 135                 140

Pro His His Gly Val Tyr Ser Arg Glu Glu Glu Leu Leu Arg Glu Arg
145                 150                 155                 160

Lys Arg Leu Gly Val Phe Gly Ile Thr Ser Tyr Asp Phe His Ser Glu
                165                 170                 175

Ser Gly Leu Phe Leu Phe Gln Ala Ser Asn Ser Leu Phe His Cys Arg
            180                 185                 190

Asp Gly Gly Lys Asn Gly Phe Met Val Ser Pro Met Lys Pro Leu Glu
        195                 200                 205

Ile Lys Thr Gln Cys Ser Gly Pro Arg Met Asp Pro Lys Ile Cys Pro
    210                 215                 220

Ala Asp Pro Ala Phe Phe Ser Phe Ile Asn Asn Ser Asp Leu Trp Val
225                 230                 235                 240

Ala Asn Ile Glu Thr Gly Glu Glu Arg Arg Leu Thr Phe Cys His Gln
                245                 250                 255
```

-continued

```
Gly Leu Ser Asn Val Leu Asp Asp Pro Lys Ser Ala Gly Val Ala Thr
            260                 265                 270

Phe Val Ile Gln Glu Glu Phe Asp Arg Phe Thr Gly Tyr Trp Trp Cys
        275                 280                 285

Pro Thr Ala Ser Trp Glu Gly Ser Glu Gly Leu Lys Thr Leu Arg Ile
    290                 295                 300

Leu Tyr Glu Glu Val Asp Glu Ser Glu Val Glu Val Ile His Val Pro
305                 310                 315                 320

Ser Pro Ala Leu Glu Glu Arg Lys Thr Asp Ser Tyr Arg Tyr Pro Arg
                325                 330                 335

Thr Gly Ser Lys Asn Pro Lys Ile Ala Leu Lys Leu Ala Glu Phe Gln
            340                 345                 350

Thr Asp Ser Gln Gly Lys Ile Val Ser Thr Gln Glu Lys Glu Leu Val
        355                 360                 365

Gln Pro Phe Ser Ser Leu Phe Pro Lys Val Glu Tyr Ile Ala Arg Ala
    370                 375                 380

Gly Trp Thr Arg Asp Gly Lys Tyr Ala Trp Ala Met Phe Leu Asp Arg
385                 390                 395                 400

Pro Gln Gln Trp Leu Gln Leu Val Leu Leu Pro Pro Ala Leu Phe Ile
                405                 410                 415

Pro Ser Thr Glu Asn Glu Glu Gln Arg Leu Ala Ser Ala Arg Ala Val
            420                 425                 430

Pro Arg Asn Val Gln Pro Tyr Val Val Tyr Glu Glu Val Thr Asn Val
        435                 440                 445

Trp Ile Asn Val His Asp Ile Phe Tyr Pro Phe Pro Gln Ser Glu Gly
    450                 455                 460

Glu Asp Glu Leu Cys Phe Leu Arg Ala Asn Glu Cys Lys Thr Gly Phe
465                 470                 475                 480

Cys His Leu Tyr Lys Val Thr Ala Val Leu Lys Ser Gln Gly Tyr Asp
                485                 490                 495

Trp Ser Glu Pro Phe Ser Pro Gly Glu Asp Glu Phe Lys Cys Pro Ile
            500                 505                 510

Lys Glu Glu Ile Ala Leu Thr Ser Gly Glu Trp Glu Val Leu Ala Arg
        515                 520                 525

His Gly Ser Lys Ile Trp Val Asn Glu Glu Thr Lys Leu Val Tyr Phe
    530                 535                 540

Gln Gly Thr Lys Asp Thr Pro Leu Glu His His Leu Tyr Val Val Ser
545                 550                 555                 560

Tyr Glu Ala Ala Gly Glu Ile Val Arg Leu Thr Thr Pro Gly Phe Ser
                565                 570                 575

His Ser Cys Ser Met Ser Gln Asn Phe Asp Met Phe Val Ser His Tyr
            580                 585                 590

Ser Ser Val Ser Thr Pro Pro Cys Val His Val Tyr Lys Leu Ser Gly
        595                 600                 605

Pro Asp Asp Asp Pro Leu His Lys Gln Pro Arg Phe Trp Ala Ser Met
    610                 615                 620

Met Glu Ala Ala Ser Cys Pro Pro Asp Tyr Val Pro Pro Glu Ile Phe
625                 630                 635                 640

His Phe His Thr Arg Ser Asp Val Arg Leu Tyr Gly Met Ile Tyr Lys
                645                 650                 655

Pro His Ala Leu Gln Pro Gly Lys Lys His Pro Thr Val Leu Phe Val
            660                 665                 670
```

-continued

```
Tyr Gly Gly Pro Gln Val Gln Leu Val Asn Asn Ser Phe Lys Gly Ile
        675                 680                 685

Lys Tyr Leu Arg Leu Asn Thr Leu Ala Ser Leu Gly Tyr Ala Val Val
    690                 695                 700

Val Ile Asp Gly Arg Gly Ser Cys Gln Arg Gly Leu Arg Phe Glu Gly
705                 710                 715                 720

Ala Leu Lys Asn Gln Met Gly Gln Val Glu Ile Glu Asp Gln Val Glu
                725                 730                 735

Gly Leu Gln Phe Val Ala Glu Lys Tyr Gly Phe Ile Asp Leu Ser Arg
            740                 745                 750

Val Ala Ile His Gly Trp Ser Tyr Gly Gly Phe Leu Ser Leu Met Gly
        755                 760                 765

Leu Ile His Lys Pro Gln Val Phe Lys Ala Gln Pro Leu Ala Tyr Pro
    770                 775                 780

Pro Arg Leu Pro Gly Arg Lys Arg Ala Leu Phe Pro His Lys Leu Pro
785                 790                 795                 800

Arg Leu Pro Thr Asp Pro Ser Arg Glu Thr Leu Pro Ala Pro Asp Leu
                805                 810                 815

Pro Gln Arg Glu Thr Gln Tyr Ser Leu Pro Arg Val Gly Arg Ala Leu
            820                 825                 830


<210> SEQ ID NO 30
<211> LENGTH: 4159
<212> TYPE: DNA
<213> ORGANISM: Homo sapiens

<400> SEQUENCE: 30

caggccgccg cctgggtcgc tcaacttccg ggtcaaaggt gcctgagccg gcgggtcccc      60

tgtgtccgcc gcggctgtcg tcccccgctc ccgccacttc cggggtcgca gtcccgggca     120

tggagccgcg accgtgaggc gccgctggac ccgggacgac ctgcccagtc cggccgccgc     180

cccacgtccc ggtctgtgtc ccacgcctgc agctggaatg gaggctctct ggacccttta     240

gaaggcaccc ctgccctcct gaggtcagct gagcggttaa tgcggaaggt taagaaactg     300

cgcctggaca aggagaacac cggaagttgg agaagcttct cgctgaattc cgagggggct     360

gagaggatgg ccaccaccgg gaccccaacg gccgaccgag gcgacgcagc cgccacagat     420

gacccggccg cccgcttcca ggtgcagaag cactcgtggg acgggctccg gagcatcatc     480

cacggcagcc gcaagtactc gggcctcatt gtcaacaagg cgccccacga cttccagttt     540

gtgcagaaga cggatgagtc tgggccccac tcccaccgcc tctactacct gggaatgcca     600

tatggcagcc gagagaactc cctcctctac tctgagattc ccaagaaggt ccggaaagag     660

gctctgctgc tcctgtcctg gaagcagatg ctggatcatt tccaggccac gccccaccat     720

ggggtctact ctcgggagga ggagctgctg agggagcgga aacgcctggg ggtcttcggc     780

atcacctcct acgacttcca cagcgagagt ggcctcttcc tcttccaggc cagcaacagc     840

ctcttccact gccgcgacgg cggcaagaac ggcttcatgg tgtcccctat gaaaccgctg     900

gaaatcaaga cccagtgctc agggccccgg atggacccca aaatctgccc tgccgaccct     960

gccttcttct ccttcatcaa taacagcgac ctgtgggtgg ccaacatcga gacaggcgag    1020

gagcggcggc tgaccttctg ccaccaaggt ttatccaatg tcctggatga ccccaagtct    1080

gcgggtgtgg ccaccttcgt catacaggaa gagttcgacc gcttcactgg gtactggtgg    1140

tgccccacag cctcctggga aggttcagag ggcctcaaga cgctgcgaat cctgtatgag    1200

gaagtcgatg agtccgaggt ggaggtcatt cacgtcccct ctcctgcgct agaagaaagg    1260
```

-continued aagacggact cgtatcggta ccccaggaca ggcagcaaga atcccaagat tgccttgaaa 1320
ctggctgagt tccagactga cagccagggc aagatcgtct cgacccagga gaaggagctg 1380
gtgcagccct tcagctcgct gttcccgaag gtggagtaca tcgccagggc cgggtggacc 1440
cgggatggca aatacgcctg ggccatgttc ctggaccggc cccagcagtg gctccagctc 1500
gtcctcctcc ccccggccct gttcatcccg agcacagaga atgaggagca gcggctagcc 1560
tctgccagag ctgtccccag gaatgtccag ccgtatgtgg tgtacgagga ggtcaccaac 1620
gtctggatca atgttcatga catcttctat cccttccccc aatcagaggg agaggacgag 1680
ctctgctttc tccgcgccaa tgaatgcaag accggcttct gccatttgta caaagtcacc 1740
gccgttttaa aatcccaggg ctacgattgg agtgagccct tcagccccgg ggaagatgaa 1800
tttaagtgcc ccattaagga agagattgct ctgaccagcg gtgaatggga ggttttggcg 1860
aggcacggct ccaagatctg ggtcaatgag gagaccaagc tggtgtactt ccagggcacc 1920
aaggacacgc cgctggagca ccacctctac gtggtcagct atgaggcggc cggcgagatc 1980
gtacgcctca ccacgcccgg cttctcccat agctgctcca tgagccagaa cttcgacatg 2040
ttcgtcagcc actacagcag cgtgagcacg ccgccctgcg tgcacgtcta caagctgagc 2100
ggccccgacg acgacccct gcacaagcag ccccgcttct gggctagcat gatggaggca 2160
gccagctgcc ccccggatta tgttcctcca gagatcttcc atttccacac gcgctcggat 2220
gtgcggctct acggcatgat ctacaagccc cacgccttgc agccagggaa gaagcacccc 2280
accgtcctct ttgtatatgg aggcccccag gtgcagctgg tgaataactc cttcaaaggc 2340
atcaagtact tgcggctcaa cacactggcc tccctgggct acgccgtggt tgtgattgac 2400
ggcaggggct cctgtcagcg agggcttcgg ttcgaagggg ccctgaaaaa ccaaatgggc 2460
caggtggaga tcgaggacca ggtggagggc ctgcagttcg tggccgagaa gtatggcttc 2520
atcgacctga gccgagttgc catccatggc tggtcctacg gggcttcct ctcgctcatg 2580 gggctaatcc acaagcccca ggtgttcaag gcccaaccgc ttgcttatcc tccacggctt 2640
cctggacgaa aacgtgcact tttccacac aaacttcctc gtctcccaac tgatccgagc 2700
agggaaacct taccagctcc agatctaccc caacgagaga cacagtattc gctgccccga 2760
gtcgggcgag cactatgaag tcacgttgct gcactttcta caggaatacc tctgagcctg 2820
cccaccggga gccgccacat cacagcacaa gtggctgcag cctccgcggg gaaccaggcg 2880
ggagggactg agtggcccgc gggccccagt gaggcacttt gtcccgccca gcgctggcca 2940
gccccgagga gccgctgcct tcaccgcccc gacgcctttt atccttttt aaacgctctt 3000 gggttttatg tccgctgctt cttggttgcc gagacagaga gatggtggtc tcgggccagc 3060
ccctcctctc cccgccttct gggaggagga ggtcacacgc tgatgggcac tggagaggcc 3120
agaagagact cagaggagcg ggctgccttc cgcctggggc tccctgtgac ctctcagtcc 3180
cctggcccgg ccagccaccg tccccagcac ccaagcatgc aattgcctgt cccccccggc 3240
cagcctcccc aacttgatgt ttgtgttttg tttgggggga tatttttcat aattatttaa 3300
aagacaggcc gggcgcggtg gctcacgtct gtaatcccag cactttggga ggctgaggcg 3360
ggcggatcac ctgaggttgg gagttcaaga ccagcctggc caacatgggg aaaccccgtc 3420
tctactaaaa atacaaaaaa ttagccgggt gtggtggcgc gtgcctataa tcccagctac 3480
tcgggaggct gaggcaggag aatcgcttga acccgggagg tggaggttgc ggtgagccaa 3540
gatcgcacca ttgcactcca gcctgggcaa caagagcgaa actctgtctc aaaataaata 3600

-continued

```
aaaaataaaa gacagaaagc aaggggtgcc taaatctaga cttggggtcc acaccgggca   3660

gcggggttgc aacccagcac ctggtaggct ccatttcttc ccaagcccga gcagagggtc   3720

atgcgggccc cacaggagaa gcggccaggg cccgcggggg gcaccacctg tggacagccc   3780

tcctgtcccc aagctttcag gcaggcactg aaacgcaccg aacttccacg ctctgctggt   3840

cagtggcggc tgtcccctcc ccagcccagc cgcccagcca catgtgtctg cctgacccgt   3900

acacaccagg ggttccgggg ttgggagctg aaccatcccc acctcagggt tatatttccc   3960

tctccccttc cctccccgcc aagagctctg ccaggggcgg gcaaaaaaaa aagtaaaaag   4020

aaaagaaaaa aaaaaaaaag aaacaaacca cctctacata ttatggaaag aaaatatttt   4080

tgtcgattct tattctttta taattatgcg tggaagaagt agacacatta aacgattcca   4140

gttggaaaca tgtcacctg                                                4159


<210> SEQ ID NO 31
<211> LENGTH: 832
<212> TYPE: PRT
<213> ORGANISM: Homo sapiens

<400> SEQUENCE: 31

Met Arg Lys Val Lys Lys Leu Arg Leu Asp Lys Glu Asn Thr Gly Ser
1               5                   10                  15

Trp Arg Ser Phe Ser Leu Asn Ser Glu Gly Ala Glu Arg Met Ala Thr
            20                  25                  30

Thr Gly Thr Pro Thr Ala Asp Arg Gly Asp Ala Ala Ala Thr Asp Asp
        35                  40                  45

Pro Ala Ala Arg Phe Gln Val Gln Lys His Ser Trp Asp Gly Leu Arg
    50                  55                  60

Ser Ile Ile His Gly Ser Arg Lys Tyr Ser Gly Leu Ile Val Asn Lys
65                  70                  75                  80

Ala Pro His Asp Phe Gln Phe Val Gln Lys Thr Asp Glu Ser Gly Pro
                85                  90                  95

His Ser His Arg Leu Tyr Tyr Leu Gly Met Pro Tyr Gly Ser Arg Glu
            100                 105                 110

Asn Ser Leu Leu Tyr Ser Glu Ile Pro Lys Lys Val Arg Lys Glu Ala
        115                 120                 125

Leu Leu Leu Leu Ser Trp Lys Gln Met Leu Asp His Phe Gln Ala Thr
    130                 135                 140

Pro His His Gly Val Tyr Ser Arg Glu Glu Glu Leu Leu Arg Glu Arg
145                 150                 155                 160

Lys Arg Leu Gly Val Phe Gly Ile Thr Ser Tyr Asp Phe His Ser Glu
                165                 170                 175

Ser Gly Leu Phe Leu Phe Gln Ala Ser Asn Ser Leu Phe His Cys Arg
            180                 185                 190

Asp Gly Gly Lys Asn Gly Phe Met Val Ser Pro Met Lys Pro Leu Glu
        195                 200                 205

Ile Lys Thr Gln Cys Ser Gly Pro Arg Met Asp Pro Lys Ile Cys Pro
    210                 215                 220

Ala Asp Pro Ala Phe Phe Ser Phe Ile Asn Asn Ser Asp Leu Trp Val
225                 230                 235                 240

Ala Asn Ile Glu Thr Gly Glu Glu Arg Arg Leu Thr Phe Cys His Gln
                245                 250                 255

Gly Leu Ser Asn Val Leu Asp Asp Pro Lys Ser Ala Gly Val Ala Thr
            260                 265                 270
```

-continued

```
Phe Val Ile Gln Glu Glu Phe Asp Arg Phe Thr Gly Tyr Trp Trp Cys
        275                 280                 285

Pro Thr Ala Ser Trp Glu Gly Ser Glu Gly Leu Lys Thr Leu Arg Ile
    290                 295                 300

Leu Tyr Glu Glu Val Asp Glu Ser Glu Val Glu Val Ile His Val Pro
305                 310                 315                 320

Ser Pro Ala Leu Glu Glu Arg Lys Thr Asp Ser Tyr Arg Tyr Pro Arg
                325                 330                 335

Thr Gly Ser Lys Asn Pro Lys Ile Ala Leu Lys Leu Ala Glu Phe Gln
            340                 345                 350

Thr Asp Ser Gln Gly Lys Ile Val Ser Thr Gln Glu Lys Glu Leu Val
        355                 360                 365

Gln Pro Phe Ser Ser Leu Phe Pro Lys Val Glu Tyr Ile Ala Arg Ala
    370                 375                 380

Gly Trp Thr Arg Asp Gly Lys Tyr Ala Trp Ala Met Phe Leu Asp Arg
385                 390                 395                 400

Pro Gln Gln Trp Leu Gln Leu Val Leu Leu Pro Pro Ala Leu Phe Ile
                405                 410                 415

Pro Ser Thr Glu Asn Glu Glu Gln Arg Leu Ala Ser Ala Arg Ala Val
            420                 425                 430

Pro Arg Asn Val Gln Pro Tyr Val Val Tyr Glu Glu Val Thr Asn Val
        435                 440                 445

Trp Ile Asn Val His Asp Ile Phe Tyr Pro Phe Pro Gln Ser Glu Gly
    450                 455                 460

Glu Asp Glu Leu Cys Phe Leu Arg Ala Asn Glu Cys Lys Thr Gly Phe
465                 470                 475                 480

Cys His Leu Tyr Lys Val Thr Ala Val Leu Lys Ser Gln Gly Tyr Asp
                485                 490                 495

Trp Ser Glu Pro Phe Ser Pro Gly Glu Asp Glu Phe Lys Cys Pro Ile
            500                 505                 510

Lys Glu Glu Ile Ala Leu Thr Ser Gly Glu Trp Glu Val Leu Ala Arg
        515                 520                 525

His Gly Ser Lys Ile Trp Val Asn Glu Glu Thr Lys Leu Val Tyr Phe
    530                 535                 540

Gln Gly Thr Lys Asp Thr Pro Leu Glu His His Leu Tyr Val Val Ser
545                 550                 555                 560

Tyr Glu Ala Ala Gly Glu Ile Val Arg Leu Thr Thr Pro Gly Phe Ser
                565                 570                 575

His Ser Cys Ser Met Ser Gln Asn Phe Asp Met Phe Val Ser His Tyr
            580                 585                 590

Ser Ser Val Ser Thr Pro Pro Cys Val His Val Tyr Lys Leu Ser Gly
        595                 600                 605

Pro Asp Asp Asp Pro Leu His Lys Gln Pro Arg Phe Trp Ala Ser Met
    610                 615                 620

Met Glu Ala Ala Ser Cys Pro Pro Asp Tyr Val Pro Pro Glu Ile Phe
625                 630                 635                 640

His Phe His Thr Arg Ser Asp Val Arg Leu Tyr Gly Met Ile Tyr Lys
                645                 650                 655

Pro His Ala Leu Gln Pro Gly Lys Lys His Pro Thr Val Leu Phe Val
            660                 665                 670

Tyr Gly Gly Pro Gln Val Gln Leu Val Asn Asn Ser Phe Lys Gly Ile
        675                 680                 685

Lys Tyr Leu Arg Leu Asn Thr Leu Ala Ser Leu Gly Tyr Ala Val Val
```

-continued

```
    690                 695                 700

Val Ile Asp Gly Arg Gly Ser Cys Gln Arg Gly Leu Arg Phe Glu Gly
705                 710                 715                 720

Ala Leu Lys Asn Gln Met Gly Gln Val Glu Ile Glu Asp Gln Val Glu
                725                 730                 735

Gly Leu Gln Phe Val Ala Glu Lys Tyr Gly Phe Ile Asp Leu Ser Arg
            740                 745                 750

Val Ala Ile His Gly Trp Ser Tyr Gly Gly Phe Leu Ser Leu Met Gly
        755                 760                 765

Leu Ile His Lys Pro Gln Val Phe Lys Ala Gln Pro Leu Ala Tyr Pro
    770                 775                 780

Pro Arg Leu Pro Gly Arg Lys Arg Ala Leu Phe Pro His Lys Leu Pro
785                 790                 795                 800

Arg Leu Pro Thr Asp Pro Ser Arg Glu Thr Leu Pro Ala Pro Asp Leu
                805                 810                 815

Pro Gln Arg Glu Thr Gln Tyr Ser Leu Pro Arg Val Gly Arg Ala Leu
            820                 825                 830


<210> SEQ ID NO 32
<211> LENGTH: 4076
<212> TYPE: DNA
<213> ORGANISM: Homo sapiens

<400> SEQUENCE: 32

caggccgccg cctgggtcgc tcaacttccg ggtcaaaggt gcctgagccg gcgggtcccc      60

tgtgtccgcc gcggctgtcg tccccgctc ccgccacttc cggggtcgca gtcccgggca     120

tggagccgcg accgtgaggc gccgctggac ccgggacgac ctgcccagtc cggccgccgc    180

cccacgtccc ggtctgtgtc ccacgcctgc agctggaatg gaggctctct ggacccttta    240

gaaggcaccc ctgccctcct gaggtcagct gagcggttaa tgcggaaggt taagaaactg    300

cgcctggaca aggagaacac cggaagttgg agaagcttct cgctgaattc cgaggggggct   360

gagaggatgg ccaccaccgg gaccccaacg gccgaccgag gcgacgcagc cgccacagat    420

gacccggccg cccgcttcca ggtgcagaag cactcgtggg acgggctccg gagcatcatc    480

cacggcagcc gcaagtactc gggcctcatt gtcaacaagg cgccccacga cttccagttt    540

gtgcagaaga cggatgagtc tgggccccac tcccaccgcc tctactacct gggaatgcca    600

tatggcagcc gagagaactc cctcctctac tctgagattc ccaagaaggt ccggaaagag    660

gctctgctgc tcctgtcctg gaagcagatg ctggatcatt tccaggccac gccccaccat    720

ggggtctact ctcgggagga ggagctgctg agggagcgga aacgcctggg ggtcttcggc    780

atcacctcct acgacttcca cagcgagagt ggcctcttcc tcttccaggc cagcaacagc    840

ctcttccact gccgcgacgg cggcaagaac ggcttcatgg tgtcccctat gaaaccgctg    900

gaaatcaaga cccagtgctc agggccccgg atggacccca aaatctgccc tgccgaccct    960

gccttcttct ccttcatcaa taacagcgac ctgtgggtgg ccaacatcga gacaggcgag    1020

gagcggcggc tgaccttctg ccaccaaggt ttatccaatg tcctggatga ccccaagtct    1080

gcgggtgtgg ccaccttcgt catacaggaa gagttcgacc gcttcactgg gtactggtgg    1140

tgccccacag cctcctggga aggttcagag ggcctcaaga cgctgcgaat cctgtatgag    1200

gaagtcgatg agtccgaggt ggaggtcatt cacgtcccct ctcctgcgct agaagaaagg    1260

aagacggact cgtatcggta ccccaggaca ggcagcaaga atcccaagat tgccttgaaa    1320

ctggctgagt tccagactga cagccagggc aagatcgtct cgacccagga gaaggagctg    1380
```

-continued

```
gtgcagccct tcagctcgct gttcccgaag gtggagtaca tcgccagggc cgggtggacc   1440
cgggatggca aatacgcctg ggccatgttc ctggaccggc cccagcagtg gctccagctc   1500
gtcctcctcc ccccggccct gttcatcccg agcacagaga atgaggagca gcggctagcc   1560
tctgccagag ctgtccccag gaatgtccag ccgtatgtgg tgtacgagga ggtcaccaac   1620
gtctggatca atgttcatga catcttctat cccttccccc aatcagaggg agaggacgag   1680
ctctgctttc tccgcgccaa tgaatgcaag accggcttct gccatttgta caaagtcacc   1740
gccgttttaa aatcccaggg ctacgattgg agtgagccct tcagccccgg ggaagatgaa   1800
tttaagtgcc ccattaagga agagattgct ctgaccagcg gtgaatggga ggttttggcg   1860
aggcacggct ccaagatctg ggtcaatgag gagaccaagc tggtgtactt ccagggcacc   1920
aaggacacgc cgctggagca ccacctctac gtggtcagct atgaggcggc cggcgagatc   1980
gtacgcctca ccacgcccgg cttctcccat agctgctcca tgagccagaa cttcgacatg   2040
ttcgtcagcc actacagcag cgtgagcacg ccgccctgcg tgcacgtcta caagctgagc   2100
ggccccgacg acgacccct gcacaagcag ccccgcttct gggctagcat gatggaggca    2160
gccagctgcc ccccggatta tgttcctcca gagatcttcc atttccacac gcgctcggat   2220
gtgcggctct acggcatgat ctacaagccc cacgccttgc agccagggaa gaagcacccc   2280
accgtcctct ttgtatatgg aggcccccag gtgcagctgg tgaataactc cttcaaaggc   2340
atcaagtact tgcggctcaa cacactggcc tccctgggct acgccgtggt tgtgattgac   2400
ggcaggggct cctgtcagcg agggcttcgg ttcgaagggg ccctgaaaaa ccaaatgggc   2460
caggtggaga tcgaggacca ggtggagggc ctgcagttcg tggccgagaa gtatggcttc   2520
atcgacctga gccgagttgc catccatggc tggtcctacg gggcttcct ctcgctcatg    2580
ggctaatcc acaagcccca ggtgttcaag gcccaaccgc ttgcttatcc tccacggctt    2640
cctggacgaa aacgtgcact ttttccacac aaacttcctc gtctcccaac tgatccgagc   2700
agggaaacct taccagctcc agatctaccc caacgagaga cacagtattc gctgccccga   2760
gtcgggcgag cactatgaag tcacgttgct gcactttcta caggaatacc tctgagcctg   2820
cccaccggga gccgccacat cacagcacaa gtggctgcag cctccgcggg gaaccaggcg   2880
ggagggactg agtggcccgc gggccccagt gaggcacttt gtcccgccca gcgctggcca   2940
gccccgagga gccgctgcct tcaccgcccc gacgcctttt atccttttt aaacgctctt    3000
gggttttatg tccgctgctt cttggttgcc gagacagaga gatggtggtc tcgggccagc   3060
ccctcctctc cccgccttct gggaggagga ggtcacacgc tgatgggcac tggagaggcc   3120
agaagagact cagaggagcg ggctgccttc cgcctggggc tccctgtgac ctctcagtcc   3180
cctggcccgg ccagccaccg tccccagcac ccaagcatgc aattgcctgt cccccccggc   3240
cagcctcccc aacttgatgt ttgtgttttg tttgggggga tatttttcat aattatttaa   3300
aagacaggcc gggcgcggtg gctcacgtct gtaatcccag cactttggga ggctgaggcg   3360
ggcggatcac ctgaggttgg gagttcaaga ccagcctggc caacatgggg aaaccccgtc   3420
tctactaaaa atacaaaaaa ttagccgggt gtggtggcgc gtgcctataa tcccagctac   3480
tcgggaggct gaggcaggag aatcgcttga acccgggagg tggaggttgc ggtgagccaa   3540
gatcgcacca ttgcactcca gcctgggcaa caagagcgaa actctgtctc aaaataaata   3600
aaaaataaaa gacagaaagc aaggggtgcc taaatctaga cttggggtcc acaccgggca   3660
gcggggttgc aacccagcac ctggtaggct ccatttcttc ccaagcccga ctttcaggca   3720
```

-continued ggcactgaaa cgcaccgaac ttccacgctc tgctggtcag tggcggctgt cccctcccca 3780
gcccagccgc ccagccacat gtgtctgcct gacccgtaca caccaggggt tccggggttg 3840
ggagctgaac catccccacc tcagggttat atttccctct cccctccct ccccgccaag 3900 agctctgcca ggggcgggca aaaaaaaaag taaaaagaaa agaaaaaaaa aaaaaagaaa 3960
caaaccacct ctacatatta tggaaagaaa atatttttgt cgattcttat tcttttataa 4020
ttatgcgtgg aagaagtaga cacattaaac gattccagtt ggaaacatgt cacctg 4076

<210> SEQ ID NO 33
<211> LENGTH: 879
<212> TYPE: PRT
<213> ORGANISM: Homo sapiens

<400> SEQUENCE: 33

Met Arg Lys Val Lys Lys Leu Arg Leu Asp Lys Glu Asn Thr Gly Ser
1 5 10 15

Trp Arg Ser Phe Ser Leu Asn Ser Glu Gly Ala Glu Arg Met Ala Thr
20 25 30

Thr Gly Thr Pro Thr Ala Asp Arg Gly Asp Ala Ala Ala Thr Asp Asp
35 40 45

Pro Ala Ala Arg Phe Gln Val Gln Lys His Ser Trp Asp Gly Leu Arg
50 55 60

Ser Ile Ile His Gly Ser Arg Lys Tyr Ser Gly Leu Ile Val Asn Lys
65 70 75 80

Ala Pro His Asp Phe Gln Phe Val Gln Lys Thr Asp Glu Ser Gly Pro
85 90 95

His Ser His Arg Leu Tyr Tyr Leu Gly Met Pro Tyr Gly Ser Arg Glu
100 105 110

Asn Ser Leu Leu Tyr Ser Glu Ile Pro Lys Lys Val Arg Lys Glu Ala
115 120 125

Leu Leu Leu Leu Ser Trp Lys Gln Met Leu Asp His Phe Gln Ala Thr
130 135 140

Pro His His Gly Val Tyr Ser Arg Glu Glu Glu Leu Leu Arg Glu Arg
145 150 155 160

Lys Arg Leu Gly Val Phe Gly Ile Thr Ser Tyr Asp Phe His Ser Glu
165 170 175

Ser Gly Leu Phe Leu Phe Gln Ala Ser Asn Ser Leu Phe His Cys Arg
180 185 190

Asp Gly Gly Lys Asn Gly Phe Met Val Ser Pro Met Lys Pro Leu Glu
195 200 205

Ile Lys Thr Gln Cys Ser Gly Pro Arg Met Asp Pro Lys Ile Cys Pro
210 215 220

Ala Asp Pro Ala Phe Phe Ser Phe Ile Asn Asn Ser Asp Leu Trp Val
225 230 235 240

Ala Asn Ile Glu Thr Gly Glu Glu Arg Arg Leu Thr Phe Cys His Gln
245 250 255

Gly Leu Ser Asn Val Leu Asp Asp Pro Lys Ser Ala Gly Val Ala Thr
260 265 270

Phe Val Ile Gln Glu Glu Phe Asp Arg Phe Thr Gly Tyr Trp Trp Cys
275 280 285

Pro Thr Ala Ser Trp Glu Gly Ser Glu Gly Leu Lys Thr Leu Arg Ile
290 295 300

Leu Tyr Glu Glu Val Asp Glu Ser Glu Val Glu Val Ile His Val Pro
305 310 315 320

-continued

Ser Pro Ala Leu Glu Glu Arg Lys Thr Asp Ser Tyr Arg Tyr Pro Arg
325 330 335

Thr Gly Ser Lys Asn Pro Lys Ile Ala Leu Lys Leu Ala Glu Phe Gln
340 345 350

Thr Asp Ser Gln Gly Lys Ile Val Ser Thr Gln Glu Lys Glu Leu Val
355 360 365

Gln Pro Phe Ser Ser Leu Phe Pro Lys Val Glu Tyr Ile Ala Arg Ala
370 375 380

Gly Trp Thr Arg Asp Gly Lys Tyr Ala Trp Ala Met Phe Leu Asp Arg
385 390 395 400

Pro Gln Gln Trp Leu Gln Leu Val Leu Leu Pro Pro Ala Leu Phe Ile
405 410 415

Pro Ser Thr Glu Asn Glu Glu Gln Arg Leu Ala Ser Ala Arg Ala Val
420 425 430

Pro Arg Asn Val Gln Pro Tyr Val Val Tyr Glu Glu Val Thr Asn Val
435 440 445

Trp Ile Asn Val His Asp Ile Phe Tyr Pro Phe Pro Gln Ser Glu Gly
450 455 460

Glu Asp Glu Leu Cys Phe Leu Arg Ala Asn Glu Cys Lys Thr Gly Phe
465 470 475 480

Cys His Leu Tyr Lys Val Thr Ala Val Leu Lys Ser Gln Gly Tyr Asp
485 490 495

Trp Ser Glu Pro Phe Ser Pro Gly Glu Asp Glu Phe Lys Cys Pro Ile
500 505 510

Lys Glu Glu Ile Ala Leu Thr Ser Gly Glu Trp Glu Val Leu Ala Arg
515 520 525

His Gly Ser Lys Gly Thr Lys Asp Thr Pro Leu Glu His His Leu Tyr
530 535 540

Val Val Ser Tyr Glu Ala Ala Gly Glu Ile Val Arg Leu Thr Thr Pro
545 550 555 560

Gly Phe Ser His Ser Cys Ser Met Ser Gln Asn Phe Asp Met Phe Val
565 570 575

Ser His Tyr Ser Ser Val Ser Thr Pro Pro Cys Val His Val Tyr Lys
580 585 590

Leu Ser Gly Pro Asp Asp Asp Pro Leu His Lys Gln Pro Arg Phe Trp
595 600 605

Ala Ser Met Met Glu Ala Ala Ser Cys Pro Pro Asp Tyr Val Pro Pro
610 615 620

Glu Ile Phe His Phe His Thr Arg Ser Asp Val Arg Leu Tyr Gly Met
625 630 635 640

Ile Tyr Lys Pro His Ala Leu Gln Pro Gly Lys Lys His Pro Thr Val
645 650 655

Leu Phe Val Tyr Gly Gly Pro Gln Val Gln Leu Val Asn Asn Ser Phe
660 665 670

Lys Gly Ile Lys Tyr Leu Arg Leu Asn Thr Leu Ala Ser Leu Gly Tyr
675 680 685

Ala Val Val Val Ile Asp Gly Arg Gly Ser Cys Gln Arg Gly Leu Arg
690 695 700

Phe Glu Gly Ala Leu Lys Asn Gln Met Gly Gln Val Glu Ile Glu Asp
705 710 715 720

Gln Val Glu Gly Leu Gln Phe Val Ala Glu Lys Tyr Gly Phe Ile Asp
725 730 735

-continued

```
Leu Ser Arg Val Ala Ile His Gly Trp Ser Tyr Gly Gly Phe Leu Ser
            740                 745                 750

Leu Met Gly Leu Ile His Lys Pro Gln Val Phe Lys Val Ala Ile Ala
        755                 760                 765

Gly Ala Pro Val Thr Val Trp Met Ala Tyr Asp Thr Gly Tyr Thr Glu
    770                 775                 780

Arg Tyr Met Asp Val Pro Glu Asn Asn Gln His Gly Tyr Glu Ala Gly
785                 790                 795                 800

Ser Val Ala Leu His Val Glu Lys Leu Pro Asn Glu Pro Asn Arg Leu
                805                 810                 815

Leu Ile Leu His Gly Phe Leu Asp Glu Asn Val His Phe Phe His Thr
            820                 825                 830

Asn Phe Leu Val Ser Gln Leu Ile Arg Ala Gly Lys Pro Tyr Gln Leu
        835                 840                 845

Gln Ile Tyr Pro Asn Glu Arg His Ser Ile Arg Cys Pro Glu Ser Gly
    850                 855                 860

Glu His Tyr Glu Val Thr Leu Leu His Phe Leu Gln Glu Tyr Leu
865                 870                 875


<210> SEQ ID NO 34
<211> LENGTH: 4263
<212> TYPE: DNA
<213> ORGANISM: Homo sapiens

<400> SEQUENCE: 34

caggccgccg cctgggtcgc tcaacttccg ggtcaaaggt gcctgagccg gcgggtcccc     60

tgtgtccgcc gcggctgtcg tccccgctc ccgccacttc cggggtcgca gtcccgggca     120

tggagccgcg accgtgaggc gccgctggac ccgggacgac ctgcccagtc cggccgccgc    180

cccacgtccc ggtctgtgtc ccacgcctgc agctggaatg gaggctctct ggacccttta    240

gaaggcaccc ctgccctcct gaggtcagct gagcggttaa tgcggaaggt taagaaactg    300

cgcctggaca aggagaacac cggaagttgg agaagcttct cgctgaattc cgagggggct    360

gagaggatgg ccaccaccgg gaccccaacg gccgaccgag gcgacgcagc cgccacagat    420

gacccggccg cccgcttcca ggtgcagaag cactcgtggg acgggctccg gagcatcatc    480

cacggcagcc gcaagtactc gggcctcatt gtcaacaagg cgccccacga cttccagttt    540

gtgcagaaga cggatgagtc tgggccccac tcccaccgcc tctactacct gggaatgcca    600

tatggcagcc gagagaactc cctcctctac tctgagattc ccaagaaggt ccggaaagag    660

gctctgctgc tcctgtcctg gaagcagatg ctggatcatt tccaggccac gccccaccat    720

ggggtctact ctcgggagga ggagctgctg agggagcgga aacgcctggg ggtcttcggc    780

atcacctcct acgacttcca cagcgagagt ggcctcttcc tcttccaggc cagcaacagc    840

ctcttccact gccgcgacgg cggcaagaac ggcttcatgg tgtcccctat gaaaccgctg    900

gaaatcaaga cccagtgctc agggccccgg atggacccca aaatctgccc tgccgaccct    960

gccttcttct ccttcatcaa taacagcgac ctgtgggtgg ccaacatcga gacaggcgag   1020

gagcggcggc tgaccttctg ccaccaaggt ttatccaatg tcctggatga ccccaagtct   1080

gcgggtgtgg ccaccttcgt catacaggaa gagttcgacc gcttcactgg gtactggtgg   1140

tgccccacag cctcctggga aggttcagag ggcctcaaga cgctgcgaat cctgtatgag   1200

gaagtcgatg agtccgaggt ggaggtcatt cacgtcccct ctcctgcgct agaagaaagg   1260

aagacggact cgtatcggta ccccaggaca ggcagcaaga atcccaagat tgccttgaaa   1320
```

-continued

```
ctggctgagt tccagactga cagccagggc aagatcgtct cgacccagga gaaggagctg   1380
gtgcagccct tcagctcgct gttcccgaag gtggagtaca tcgccagggc cgggtggacc   1440
cgggatggca aatacgcctg ggccatgttc ctggaccggc cccagcagtg gctccagctc   1500
gtcctcctcc ccccggccct gttcatcccg agcacagaga atgaggagca gcggctagcc   1560
tctgccagag ctgtccccag gaatgtccag ccgtatgtgg tgtacgagga ggtcaccaac   1620
gtctggatca atgttcatga catcttctat cccttccccc aatcagaggg agaggacgag   1680
ctctgctttc tccgcgccaa tgaatgcaag accggcttct gccatttgta caaagtcacc   1740
gccgttttaa aatcccaggg ctacgattgg agtgagccct tcagccccgg ggaagatgaa   1800
tttaagtgcc ccattaagga agagattgct ctgaccagcg gtgaatggga ggttttggcg   1860
aggcacggct ccaagggcac caaggacacg ccgctggagc accacctcta cgtggtcagc   1920
tatgaggcgg ccggcgagat cgtacgcctc accacgcccg gcttctccca tagctgctcc   1980
atgagccaga acttcgacat gttcgtcagc cactacagca gcgtgagcac gccgccctgc   2040
gtgcacgtct acaagctgag cggccccgac gacgaccccc tgcacaagca gccccgcttc   2100
tgggctagca tgatggaggc agccagctgc cccccggatt atgttcctcc agagatcttc   2160
catttccaca cgcgctcgga tgtgcggctc tacggcatga tctacaagcc ccacgccttg   2220
cagccaggga agaagcaccc caccgtcctc tttgtatatg gaggccccca ggtgcagctg   2280
gtgaataact ccttcaaagg catcaagtac ttgcggctca acacactggc ctccctgggc   2340
tacgccgtgg ttgtgattga cggcaggggc tcctgtcagc gagggcttcg gttcgaaggg   2400
gccctgaaaa accaaatggg ccaggtggag atcgaggacc aggtggaggg cctgcagttc   2460
gtggccgaga agtatggctt catcgacctg agccgagttg ccatccatgg ctggtcctac   2520
gggggcttcc tctcgctcat ggggctaatc cacaagcccc aggtgttcaa ggtggccatc   2580
gcgggtgccc cggtcaccgt ctggatggcc tacgacacag ggtacactga gcgctacatg   2640
gacgtccctg agaacaacca gcacggctat gaggcgggtt ccgtggccct gcacgtggag   2700
aagctgccca atgagcccaa ccgcttgctt atcctccacg gcttcctgga cgaaaacgtg   2760
cactttttcc acacaaactt cctcgtctcc caactgatcc gagcagggaa accttaccag   2820
ctccagatct accccaacga gagacacagt attcgctgcc ccgagtcggg cgagcactat   2880
gaagtcacgt tgctgcactt tctacaggaa tacctctgag cctgcccacc gggagccgcc   2940
acatcacagc acaagtggct gcagcctccg cggggaacca ggcgggaggg actgagtggc   3000
ccgcgggccc cagtgaggca ctttgtcccg cccagcgctg gccagccccg aggagccgct   3060
gccttcaccg ccccgacgcc ttttatcctt ttttaaacgc tcttgggttt tatgtccgct   3120
gcttcttggt tgccgagaca gagagatggt ggtctcgggc cagcccctcc tctccccgcc   3180
ttctgggagg aggaggtcac acgctgatgg gcactggaga ggccagaaga gactcagagg   3240
agcgggctgc cttccgcctg gggctccctg tgacctctca gtcccctggc ccggccagcc   3300
accgtcccca gcacccaagc atgcaattgc ctgtcccccc cggccagcct ccccaacttg   3360
atgtttgtgt tttgtttggg gggatatttt tcataattat ttaaaagaca ggccgggcgc   3420
ggtggctcac gtctgtaatc ccagcacttt gggaggctga ggcgggcgga tcacctgagg   3480
ttgggagttc aagaccagcc tggccaacat ggggaaaccc cgtctctact aaaaatacaa   3540
aaaattagcc gggtgtggtg gcgcgtgcct ataatcccag ctactcggga ggctgaggca   3600
ggagaatcgc ttgaacccgg gaggtggagg ttgcggtgag ccaagatcgc accattgcac   3660
tccagcctgg gcaacaagag cgaaactctg tctcaaaata aataaaaaat aaaagacaga   3720
```

-continued

```
aagcaagggg tgcctaaatc tagacttggg gtccacaccg ggcagcgggg ttgcaaccca   3780

gcacctggta ggctccattt cttcccaagc ccgagcagag ggtcatgcgg gccccacagg   3840

agaagcggcc agggcccgcg gggggcacca cctgtggaca gccctcctgt ccccaagctt   3900

tcaggcaggc actgaaacgc accgaacttc cacgctctgc tggtcagtgg cggctgtccc   3960

ctccccagcc cagccgccca gccacatgtg tctgcctgac ccgtacacac caggggttcc   4020

ggggttggga gctgaaccat ccccacctca gggttatatt tccctctccc cttccctccc   4080

cgccaagagc tctgccaggg gcgggcaaaa aaaaaagtaa aaagaaaaga aaaaaaaaaa   4140

aaagaaacaa accacctcta catattatgg aaagaaaata tttttgtcga ttcttattct   4200

tttataatta tgcgtggaag aagtagacac attaaacgat tccagttgga aacatgtcac   4260

ctg                                                                 4263
```

```
<210> SEQ ID NO 35
<211> LENGTH: 879
<212> TYPE: PRT
<213> ORGANISM: Homo sapiens

<400> SEQUENCE: 35

Met Arg Lys Val Lys Lys Leu Arg Leu Asp Lys Glu Asn Thr Gly Ser
1               5                   10                  15

Trp Arg Ser Phe Ser Leu Asn Ser Glu Gly Ala Glu Arg Met Ala Thr
            20                  25                  30

Thr Gly Thr Pro Thr Ala Asp Arg Gly Asp Ala Ala Ala Thr Asp Asp
        35                  40                  45

Pro Ala Ala Arg Phe Gln Val Gln Lys His Ser Trp Asp Gly Leu Arg
    50                  55                  60

Ser Ile Ile His Gly Ser Arg Lys Tyr Ser Gly Leu Ile Val Asn Lys
65                  70                  75                  80

Ala Pro His Asp Phe Gln Phe Val Gln Lys Thr Asp Glu Ser Gly Pro
                85                  90                  95

His Ser His Arg Leu Tyr Tyr Leu Gly Met Pro Tyr Gly Ser Arg Glu
            100                 105                 110

Asn Ser Leu Leu Tyr Ser Glu Ile Pro Lys Lys Val Arg Lys Glu Ala
        115                 120                 125

Leu Leu Leu Leu Ser Trp Lys Gln Met Leu Asp His Phe Gln Ala Thr
    130                 135                 140

Pro His His Gly Val Tyr Ser Arg Glu Glu Glu Leu Leu Arg Glu Arg
145                 150                 155                 160

Lys Arg Leu Gly Val Phe Gly Ile Thr Ser Tyr Asp Phe His Ser Glu
                165                 170                 175

Ser Gly Leu Phe Leu Phe Gln Ala Ser Asn Ser Leu Phe His Cys Arg
            180                 185                 190

Asp Gly Gly Lys Asn Gly Phe Met Val Ser Pro Met Lys Pro Leu Glu
        195                 200                 205

Ile Lys Thr Gln Cys Ser Gly Pro Arg Met Asp Pro Lys Ile Cys Pro
    210                 215                 220

Ala Asp Pro Ala Phe Phe Ser Phe Ile Asn Asn Ser Asp Leu Trp Val
225                 230                 235                 240

Ala Asn Ile Glu Thr Gly Glu Glu Arg Arg Leu Thr Phe Cys His Gln
                245                 250                 255

Gly Leu Ser Asn Val Leu Asp Asp Pro Lys Ser Ala Gly Val Ala Thr
            260                 265                 270
```

-continued

```
Phe Val Ile Gln Glu Glu Phe Asp Arg Phe Thr Gly Tyr Trp Trp Cys
        275                 280                 285

Pro Thr Ala Ser Trp Glu Gly Ser Glu Gly Leu Lys Thr Leu Arg Ile
    290                 295                 300

Leu Tyr Glu Glu Val Asp Glu Ser Glu Val Glu Val Ile His Val Pro
305                 310                 315                 320

Ser Pro Ala Leu Glu Glu Arg Lys Thr Asp Ser Tyr Arg Tyr Pro Arg
                325                 330                 335

Thr Gly Ser Lys Asn Pro Lys Ile Ala Leu Lys Leu Ala Glu Phe Gln
            340                 345                 350

Thr Asp Ser Gln Gly Lys Ile Val Ser Thr Gln Glu Lys Glu Leu Val
        355                 360                 365

Gln Pro Phe Ser Ser Leu Phe Pro Lys Val Glu Tyr Ile Ala Arg Ala
    370                 375                 380

Gly Trp Thr Arg Asp Gly Lys Tyr Ala Trp Ala Met Phe Leu Asp Arg
385                 390                 395                 400

Pro Gln Gln Trp Leu Gln Leu Val Leu Leu Pro Pro Ala Leu Phe Ile
                405                 410                 415

Pro Ser Thr Glu Asn Glu Glu Gln Arg Leu Ala Ser Ala Arg Ala Val
            420                 425                 430

Pro Arg Asn Val Gln Pro Tyr Val Val Tyr Glu Glu Val Thr Asn Val
        435                 440                 445

Trp Ile Asn Val His Asp Ile Phe Tyr Pro Phe Pro Gln Ser Glu Gly
    450                 455                 460

Glu Asp Glu Leu Cys Phe Leu Arg Ala Asn Glu Cys Lys Thr Gly Phe
465                 470                 475                 480

Cys His Leu Tyr Lys Val Thr Ala Val Leu Lys Ser Gln Gly Tyr Asp
                485                 490                 495

Trp Ser Glu Pro Phe Ser Pro Gly Glu Asp Glu Phe Lys Cys Pro Ile
            500                 505                 510

Lys Glu Glu Ile Ala Leu Thr Ser Gly Glu Trp Glu Val Leu Ala Arg
        515                 520                 525

His Gly Ser Lys Gly Thr Lys Asp Thr Pro Leu Glu His His Leu Tyr
    530                 535                 540

Val Val Ser Tyr Glu Ala Ala Gly Glu Ile Val Arg Leu Thr Thr Pro
545                 550                 555                 560

Gly Phe Ser His Ser Cys Ser Met Ser Gln Asn Phe Asp Met Phe Val
                565                 570                 575

Ser His Tyr Ser Ser Val Ser Thr Pro Pro Cys Val His Val Tyr Lys
            580                 585                 590

Leu Ser Gly Pro Asp Asp Asp Pro Leu His Lys Gln Pro Arg Phe Trp
        595                 600                 605

Ala Ser Met Met Glu Ala Ala Ser Cys Pro Pro Asp Tyr Val Pro Pro
    610                 615                 620

Glu Ile Phe His Phe His Thr Arg Ser Asp Val Arg Leu Tyr Gly Met
625                 630                 635                 640

Ile Tyr Lys Pro His Ala Leu Gln Pro Gly Lys Lys His Pro Thr Val
                645                 650                 655

Leu Phe Val Tyr Gly Gly Pro Gln Val Gln Leu Val Asn Asn Ser Phe
            660                 665                 670

Lys Gly Ile Lys Tyr Leu Arg Leu Asn Thr Leu Ala Ser Leu Gly Tyr
        675                 680                 685
```

-continued

```
Ala Val Val Val Ile Asp Gly Arg Gly Ser Cys Gln Arg Gly Leu Arg
    690                 695                 700

Phe Glu Gly Ala Leu Lys Asn Gln Met Gly Gln Val Glu Ile Glu Asp
705                 710                 715                 720

Gln Val Glu Gly Leu Gln Phe Val Ala Glu Lys Tyr Gly Phe Ile Asp
                725                 730                 735

Leu Ser Arg Val Ala Ile His Gly Trp Ser Tyr Gly Gly Phe Leu Ser
            740                 745                 750

Leu Met Gly Leu Ile His Lys Pro Gln Val Phe Lys Val Ala Ile Ala
        755                 760                 765

Gly Ala Pro Val Thr Val Trp Met Ala Tyr Asp Thr Gly Tyr Thr Glu
    770                 775                 780

Arg Tyr Met Asp Val Pro Glu Asn Asn Gln His Gly Tyr Glu Ala Gly
785                 790                 795                 800

Ser Val Ala Leu His Val Glu Lys Leu Pro Asn Glu Pro Asn Arg Leu
                805                 810                 815

Leu Ile Leu His Gly Phe Leu Asp Glu Asn Val His Phe Phe His Thr
            820                 825                 830

Asn Phe Leu Val Ser Gln Leu Ile Arg Ala Gly Lys Pro Tyr Gln Leu
        835                 840                 845

Gln Ile Tyr Pro Asn Glu Arg His Ser Ile Arg Cys Pro Glu Ser Gly
    850                 855                 860

Glu His Tyr Glu Val Thr Leu Leu His Phe Leu Gln Glu Tyr Leu
865                 870                 875


<210> SEQ ID NO 36
<211> LENGTH: 4180
<212> TYPE: DNA
<213> ORGANISM: Homo sapiens

<400> SEQUENCE: 36

caggccgccg cctgggtcgc tcaacttccg ggtcaaaggt gcctgagccg gcgggtcccc      60

tgtgtccgcc gcggctgtcg tccccegctc ccgccacttc cggggtcgca gtcccgggca     120

tggagccgcg accgtgaggc gccgctggac ccgggacgac ctgcccagtc cggccgccgc     180

cccacgtccc ggtctgtgtc ccacgcctgc agctggaatg gaggctctct ggacccttta     240

gaaggcaccc ctgccctcct gaggtcagct gagcggttaa tgcggaaggt taagaaactg     300

cgcctggaca aggagaacac cggaagttgg agaagcttct cgctgaattc cgagggggct     360

gagaggatgg ccaccaccgg gaccccaacg gccgaccgag gcgacgcagc cgccacagat     420

gacccggccg cccgcttcca ggtgcagaag cactcgtggg acgggctccg gagcatcatc     480

cacggcagcc gcaagtactc gggcctcatt gtcaacaagg cgccccacga cttccagttt     540

gtgcagaaga cggatgagtc tgggccccac tcccaccgcc tctactacct gggaatgcca     600

tatggcagcc gagagaactc cctcctctac tctgagattc ccaagaaggt ccggaaagag     660

gctctgctgc tcctgtcctg gaagcagatg ctggatcatt tccaggccac gccccaccat     720

ggggtctact ctcgggagga ggagctgctg agggagcgga aacgcctggg ggtcttcggc     780

atcacctcct acgacttcca cagcgagagt ggcctcttcc tcttccaggc cagcaacagc     840

ctcttccact gccgcgacgg cggcaagaac ggcttcatgg tgtcccctat gaaaccgctg     900

gaaatcaaga cccagtgctc agggccccgg atggacccca aaatctgccc tgccgaccct     960

gccttcttct ccttcatcaa taacagcgac ctgtgggtgg ccaacatcga gacaggcgag    1020

gagcggcggc tgaccttctg ccaccaaggt ttatccaatg tcctggatga ccccaagtct    1080
```

-continued

```
gcgggtgtgg ccaccttcgt catacaggaa gagttcgacc gcttcactgg gtactggtgg   1140
tgccccacag cctcctggga aggttcagag ggcctcaaga cgctgcgaat cctgtatgag   1200
gaagtcgatg agtccgaggt ggaggtcatt cacgtcccct ctcctgcgct agaagaaagg   1260
aagacggact cgtatcggta ccccaggaca ggcagcaaga atcccaagat tgccttgaaa   1320
ctggctgagt tccagactga cagccagggc aagatcgtct cgacccagga gaaggagctg   1380
gtgcagccct tcagctcgct gttcccgaag gtggagtaca tcgccagggc cgggtggacc   1440
cgggatggca aatacgcctg ggccatgttc ctggaccggc cccagcagtg gctccagctc   1500
gtcctcctcc ccccggccct gttcatcccg agcacagaga atgaggagca gcggctagcc   1560
tctgccagag ctgtccccag gaatgtccag ccgtatgtgg tgtacgagga ggtcaccaac   1620
gtctggatca atgttcatga catcttctat cccttccccc aatcagaggg agaggacgag   1680
ctctgctttc tccgcgccaa tgaatgcaag accggcttct gccatttgta caaagtcacc   1740
gccgttttaa aatcccaggg ctacgattgg agtgagccct tcagccccgg ggaagatgaa   1800
tttaagtgcc ccattaagga agagattgct ctgaccagcg gtgaatggga ggttttggcg   1860
aggcacggct ccaagggcac caaggacacg ccgctggagc accacctcta cgtggtcagc   1920
tatgaggcgg ccggcgagat cgtacgcctc accacgcccg gcttctccca tagctgctcc   1980
atgagccaga acttcgacat gttcgtcagc cactacagca gcgtgagcac gccgccctgc   2040
gtgcacgtct acaagctgag cggccccgac gacgaccccc tgcacaagca gccccgcttc   2100
tgggctagca tgatggaggc agccagctgc cccccggatt atgttcctcc agagatcttc   2160
catttccaca cgcgctcgga tgtgcggctc tacggcatga tctacaagcc ccacgccttg   2220
cagccaggga agaagcaccc caccgtcctc tttgtatatg gaggccccca ggtgcagctg   2280
gtgaataact ccttcaaagg catcaagtac ttgcggctca acacactggc ctccctgggc   2340
tacgccgtgg ttgtgattga cggcaggggc tcctgtcagc gagggcttcg gttcgaaggg   2400
gccctgaaaa accaaatggg ccaggtggag atcgaggacc aggtggaggg cctgcagttc   2460
gtggccgaga agtatggctt catcgacctg agccgagttg ccatccatgg ctggtcctac   2520
gggggcttcc tctcgctcat ggggctaatc cacaagcccc aggtgttcaa ggtggccatc   2580
gcgggtgccc cggtcaccgt ctggatggcc tacgacacag ggtacactga gcgctacatg   2640
gacgtccctg agaacaacca gcacggctat gaggcgggtt ccgtggccct gcacgtggag   2700
aagctgccca atgagcccaa ccgcttgctt atcctccacg gcttcctgga cgaaaacgtg   2760
cactttttcc acacaaactt cctcgtctcc caactgatcc gagcagggaa accttaccag   2820
ctccagatct accccaacga gagacacagt attcgctgcc ccgagtcggg cgagcactat   2880
gaagtcacgt tgctgcactt tctacaggaa tacctctgag cctgcccacc gggagccgcc   2940
acatcacagc acaagtggct gcagcctccg cggggaacca ggcgggaggg actgagtggc   3000
ccgcgggccc cagtgaggca ctttgtcccg cccagcgctg gccagccccg aggagccgct   3060
gccttcaccg ccccgacgcc ttttatcctt ttttaaacgc tcttgggttt tatgtccgct   3120
gcttcttggt tgccgagaca gagagatggt ggtctcgggc cagcccctcc tctccccgcc   3180
ttctgggagg aggaggtcac acgctgatgg gcactggaga ggccagaaga gactcagagg   3240
agcgggctgc cttccgcctg gggctccctg tgacctctca gtcccctggc ccggccagcc   3300
accgtcccca gcacccaagc atgcaattgc ctgtcccccc cggccagcct ccccaacttg   3360
atgtttgtgt tttgtttggg gggatatttt tcataattat ttaaaagaca ggccgggcgc   3420
```

-continued

```
ggtggctcac gtctgtaatc ccagcacttt gggaggctga ggcgggcgga tcacctgagg   3480

ttgggagttc aagaccagcc tggccaacat ggggaaaccc cgtctctact aaaaatacaa   3540

aaaattagcc gggtgtggtg gcgcgtgcct ataatcccag ctactcggga ggctgaggca   3600

ggagaatcgc ttgaacccgg gaggtggagg ttgcggtgag ccaagatcgc accattgcac   3660

tccagcctgg gcaacaagag cgaaactctg tctcaaaata aataaaaaat aaaagacaga   3720

aagcaagggg tgcctaaatc tagacttggg gtccacaccg ggcagcgggg ttgcaaccca   3780

gcacctggta ggctccattt cttcccaagc ccgactttca ggcaggcact gaaacgcacc   3840

gaacttccac gctctgctgg tcagtggcgg ctgtcccctc cccagcccag ccgcccagcc   3900

acatgtgtct gcctgacccg tacacaccag gggttccggg gttgggagct gaaccatccc   3960

cacctcaggg ttatatttcc ctctcccctt ccctccccgc caagagctct gccaggggcg   4020

ggcaaaaaaa aaagtaaaaa gaaaagaaaa aaaaaaaaaa gaaacaaacc acctctacat   4080

attatggaaa gaaaatattt ttgtcgattc ttattctttt ataattatgc gtggaagaag   4140

tagacacatt aaacgattcc agttggaaac atgtcacctg                         4180


<210> SEQ ID NO 37
<211> LENGTH: 819
<212> TYPE: PRT
<213> ORGANISM: Homo sapiens

<400> SEQUENCE: 37

Met Arg Lys Val Lys Lys Leu Arg Leu Asp Lys Glu Asn Thr Gly Ser
1               5                   10                  15

Trp Arg Ser Phe Ser Leu Asn Ser Glu Gly Ala Glu Arg Met Ala Thr
            20                  25                  30

Thr Gly Thr Pro Thr Ala Asp Arg Gly Asp Ala Ala Ala Thr Asp Asp
        35                  40                  45

Pro Ala Ala Arg Phe Gln Val Gln Lys His Ser Trp Asp Gly Leu Arg
    50                  55                  60

Ser Ile Ile His Gly Ser Arg Lys Tyr Ser Gly Leu Ile Val Asn Lys
65                  70                  75                  80

Ala Pro His Asp Phe Gln Phe Val Gln Lys Thr Asp Glu Ser Gly Pro
                85                  90                  95

His Ser His Arg Leu Tyr Tyr Leu Gly Met Pro Tyr Gly Ser Arg Glu
            100                 105                 110

Asn Ser Leu Leu Tyr Ser Glu Ile Pro Lys Lys Val Arg Lys Glu Ala
        115                 120                 125

Leu Leu Leu Leu Ser Trp Lys Gln Met Leu Asp His Phe Gln Ala Thr
    130                 135                 140

Pro His His Gly Val Tyr Ser Arg Glu Glu Glu Leu Leu Arg Glu Arg
145                 150                 155                 160

Lys Arg Leu Gly Val Phe Gly Ile Thr Ser Tyr Asp Phe His Ser Glu
                165                 170                 175

Ser Gly Leu Phe Leu Phe Gln Ala Ser Asn Ser Leu Phe His Cys Arg
            180                 185                 190

Asp Gly Gly Lys Asn Gly Phe Met Val Ser Pro Met Lys Pro Leu Glu
        195                 200                 205

Ile Lys Thr Gln Cys Ser Gly Pro Arg Met Asp Pro Lys Ile Cys Pro
    210                 215                 220

Ala Asp Pro Ala Phe Phe Ser Phe Ile Asn Asn Ser Asp Leu Trp Val
225                 230                 235                 240
```

-continued

```
Ala Asn Ile Glu Thr Gly Glu Glu Arg Arg Leu Thr Phe Cys His Gln
                245                 250                 255

Gly Leu Ser Asn Val Leu Asp Asp Pro Lys Ser Ala Gly Val Ala Thr
            260                 265                 270

Phe Val Ile Gln Glu Glu Phe Asp Arg Phe Thr Gly Tyr Trp Trp Cys
        275                 280                 285

Pro Thr Ala Ser Trp Glu Gly Ser Glu Gly Leu Lys Thr Leu Arg Ile
    290                 295                 300

Leu Tyr Glu Glu Val Asp Glu Ser Glu Val Glu Val Ile His Val Pro
305                 310                 315                 320

Ser Pro Ala Leu Glu Glu Arg Lys Thr Asp Ser Tyr Arg Tyr Pro Arg
                325                 330                 335

Thr Gly Ser Lys Asn Pro Lys Ile Ala Leu Lys Leu Ala Glu Phe Gln
            340                 345                 350

Thr Asp Ser Gln Gly Lys Ile Val Ser Thr Gln Glu Lys Glu Leu Val
        355                 360                 365

Gln Pro Phe Ser Ser Leu Phe Pro Lys Val Glu Tyr Ile Ala Arg Ala
    370                 375                 380

Gly Trp Thr Arg Asp Gly Lys Tyr Ala Trp Ala Met Phe Leu Asp Arg
385                 390                 395                 400

Pro Gln Gln Trp Leu Gln Leu Val Leu Leu Pro Pro Ala Leu Phe Ile
                405                 410                 415

Pro Ser Thr Glu Asn Glu Glu Gln Arg Leu Ala Ser Ala Arg Ala Val
            420                 425                 430

Pro Arg Asn Val Gln Pro Tyr Val Val Tyr Glu Glu Val Thr Asn Val
        435                 440                 445

Trp Ile Asn Val His Asp Ile Phe Tyr Pro Phe Pro Gln Ser Glu Gly
    450                 455                 460

Glu Asp Glu Leu Cys Phe Leu Arg Ala Asn Glu Cys Lys Thr Gly Phe
465                 470                 475                 480

Cys His Leu Tyr Lys Val Thr Ala Val Leu Lys Ser Gln Gly Tyr Asp
                485                 490                 495

Trp Ser Glu Pro Phe Ser Pro Gly Glu Asp Glu Phe Lys Cys Pro Ile
            500                 505                 510

Lys Glu Glu Ile Ala Leu Thr Ser Gly Glu Trp Glu Val Leu Ala Arg
        515                 520                 525

His Gly Ser Lys Gly Thr Lys Asp Thr Pro Leu Glu His His Leu Tyr
    530                 535                 540

Val Val Ser Tyr Glu Ala Ala Gly Glu Ile Val Arg Leu Thr Thr Pro
545                 550                 555                 560

Gly Phe Ser His Ser Cys Ser Met Ser Gln Asn Phe Asp Met Phe Val
                565                 570                 575

Ser His Tyr Ser Ser Val Ser Thr Pro Pro Cys Val His Val Tyr Lys
            580                 585                 590

Leu Ser Gly Pro Asp Asp Asp Pro Leu His Lys Gln Pro Arg Phe Trp
        595                 600                 605

Ala Ser Met Met Glu Ala Ala Ser Cys Pro Pro Asp Tyr Val Pro Pro
    610                 615                 620

Glu Ile Phe His Phe His Thr Arg Ser Asp Val Arg Leu Tyr Gly Met
625                 630                 635                 640

Ile Tyr Lys Pro His Ala Leu Gln Pro Gly Lys Lys His Pro Thr Val
                645                 650                 655

Leu Phe Val Tyr Gly Gly Pro Gln Val Gln Leu Val Asn Asn Ser Phe
```

-continued

```
            660                 665                 670

Lys Gly Ile Lys Tyr Leu Arg Leu Asn Thr Leu Ala Ser Leu Gly Tyr
        675                 680                 685

Ala Val Val Val Ile Asp Gly Arg Gly Ser Cys Gln Arg Gly Leu Arg
    690                 695                 700

Phe Glu Gly Ala Leu Lys Asn Gln Met Gly Gln Val Glu Ile Glu Asp
705                 710                 715                 720

Gln Val Glu Gly Leu Gln Phe Val Ala Glu Lys Tyr Gly Phe Ile Asp
                725                 730                 735

Leu Ser Arg Val Ala Ile His Gly Trp Ser Tyr Gly Gly Phe Leu Ser
            740                 745                 750

Leu Met Gly Leu Ile His Lys Pro Gln Val Phe Lys Ala Gln Pro Leu
        755                 760                 765

Ala Tyr Pro Pro Arg Leu Pro Gly Arg Lys Arg Ala Leu Phe Pro His
    770                 775                 780

Lys Leu Pro Arg Leu Pro Thr Asp Pro Ser Arg Glu Thr Leu Pro Ala
785                 790                 795                 800

Pro Asp Leu Pro Gln Arg Glu Thr Gln Tyr Ser Leu Pro Arg Val Gly
                805                 810                 815

Arg Ala Leu


<210> SEQ ID NO 38
<211> LENGTH: 4120
<212> TYPE: DNA
<213> ORGANISM: Homo sapiens

<400> SEQUENCE: 38

caggccgccg cctgggtcgc tcaacttccg ggtcaaaggt gcctgagccg gcgggtcccc      60

tgtgtccgcc gcggctgtcg tcccccgctc ccgccacttc cggggtcgca gtcccgggca     120

tggagccgcg accgtgaggc gccgctggac ccgggacgac ctgcccagtc cggccgccgc     180

cccacgtccc ggtctgtgtc ccacgcctgc agctggaatg gaggctctct ggacccttta     240

gaaggcaccc ctgccctcct gaggtcagct gagcggttaa tgcggaaggt taagaaactg     300

cgcctggaca aggagaacac cggaagttgg agaagcttct cgctgaattc cgagggggct     360

gagaggatgg ccaccaccgg gaccccaacg gccgaccgag gcgacgcagc cgccacagat     420

gacccggccg cccgcttcca ggtgcagaag cactcgtggg acgggctccg gagcatcatc     480

cacggcagcc gcaagtactc gggcctcatt gtcaacaagg cgccccacga cttccagttt     540

gtgcagaaga cggatgagtc tgggccccac tcccaccgcc tctactacct gggaatgcca     600

tatggcagcc gagagaactc cctcctctac tctgagattc ccaagaaggt ccggaaagag     660

gctctgctgc tcctgtcctg gaagcagatg ctggatcatt tccaggccac gccccaccat     720

ggggtctact ctcgggagga ggagctgctg agggagcgga aacgcctggg ggtcttcggc     780

atcacctcct acgacttcca cagcgagagt ggcctcttcc tcttccaggc cagcaacagc     840

ctcttccact gccgcgacgg cggcaagaac ggcttcatgg tgtcccctat gaaaccgctg     900

gaaatcaaga cccagtgctc agggccccgg atggacccca aaatctgccc tgccgaccct     960

gccttcttct ccttcatcaa taacagcgac ctgtgggtgg ccaacatcga gacaggcgag    1020

gagcggcggc tgaccttctg ccaccaaggt ttatccaatg tcctggatga ccccaagtct    1080

gcgggtgtgg ccaccttcgt catacaggaa gagttcgacc gcttcactgg gtactggtgg    1140

tgccccacag cctcctggga aggttcagag ggcctcaaga cgctgcgaat cctgtatgag    1200
```

-continued

```
gaagtcgatg agtccgaggt ggaggtcatt cacgtcccct ctcctgcgct agaagaaagg   1260
aagacggact cgtatcggta ccccaggaca ggcagcaaga atcccaagat tgccttgaaa   1320
ctggctgagt tccagactga cagccagggc aagatcgtct cgacccagga gaaggagctg   1380
gtgcagccct tcagctcgct gttcccgaag gtggagtaca tcgccagggc cgggtggacc   1440
cgggatggca aatacgcctg ggccatgttc ctggaccggc cccagcagtg gctccagctc   1500
gtcctcctcc ccccggccct gttcatcccg agcacagaga atgaggagca gcggctagcc   1560
tctgccagag ctgtccccag gaatgtccag ccgtatgtgg tgtacgagga ggtcaccaac   1620
gtctggatca atgttcatga catcttctat cccttccccc aatcagaggg agaggacgag   1680
ctctgctttc tccgcgccaa tgaatgcaag accggcttct gccatttgta caaagtcacc   1740
gccgttttaa aatcccaggg ctacgattgg agtgagccct tcagccccgg ggaagatgaa   1800
tttaagtgcc ccattaagga agagattgct ctgaccagcg gtgaatggga ggttttggcg   1860
aggcacggct ccaagggcac caaggacacg ccgctggagc accacctcta cgtggtcagc   1920
tatgaggcgg ccggcgagat cgtacgcctc accacgcccg gcttctccca tagctgctcc   1980
atgagccaga acttcgacat gttcgtcagc cactacagca gcgtgagcac gccgccctgc   2040
gtgcacgtct acaagctgag cggccccgac gacgaccccc tgcacaagca gccccgcttc   2100
tgggctagca tgatggaggc agccagctgc cccccggatt atgttcctcc agagatcttc   2160
catttccaca cgcgctcgga tgtgcggctc tacggcatga tctacaagcc ccacgccttg   2220
cagccaggga agaagcaccc caccgtcctc tttgtatatg gaggccccca ggtgcagctg   2280
gtgaataact ccttcaaagg catcaagtac ttgcggctca acacactggc ctccctgggc   2340
tacgccgtgg ttgtgattga cggcaggggc tcctgtcagc gagggcttcg gttcgaaggg   2400
gccctgaaaa accaaatggg ccaggtggag atcgaggacc aggtggaggg cctgcagttc   2460
gtggccgaga agtatggctt catcgacctg agccgagttg ccatccatgg ctggtcctac   2520
gggggcttcc tctcgctcat ggggctaatc cacaagcccc aggtgttcaa ggcccaaccg   2580
cttgcttatc ctccacggct tcctggacga aaacgtgcac tttttccaca caaacttcct   2640
cgtctcccaa ctgatccgag cagggaaacc ttaccagctc cagatctacc ccaacgagag   2700
acacagtatt cgctgccccg agtcgggcga gcactatgaa gtcacgttgc tgcactttct   2760
acaggaatac ctctgagcct gcccaccggg agccgccaca tcacagcaca agtggctgca   2820
gcctccgcgg ggaaccaggc gggagggact gagtggcccg cgggccccag tgaggcactt   2880
tgtcccgccc agcgctggcc agccccgagg agccgctgcc ttcaccgccc cgacgccttt   2940
tatccttttt taaacgctct tgggttttat gtccgctgct tcttggttgc cgagacagag   3000
agatggtggt ctcgggccag cccctcctct ccccgccttc tgggaggagg aggtcacacg   3060
ctgatgggca ctggagaggc cagaagagac tcagaggagc gggctgcctt ccgcctgggg   3120
ctccctgtga cctctcagtc ccctggcccg gccagccacc gtccccagca cccaagcatg   3180
caattgcctg tccccccgg ccagcctccc caacttgatg tttgtgtttt gtttgggggg   3240
atatttttca taattattta aaagacaggc cgggcgcggt ggctcacgtc tgtaatccca   3300
gcactttggg aggctgaggc gggcggatca cctgaggttg ggagttcaag accagcctgg   3360
ccaacatggg gaaaccccgt ctctactaaa aatacaaaaa attagccggg tgtggtggcg   3420
cgtgcctata atcccagcta ctcgggaggc tgaggcagga gaatcgcttg aacccgggag   3480
gtggaggttg cggtgagcca agatcgcacc attgcactcc agcctgggca acaagagcga   3540
aactctgtct caaaataaat aaaaaataaa agacagaaag caaggggtgc ctaaatctag   3600
```

-continued

```
acttggggtc cacaccgggc agcggggttg caacccagca cctggtaggc tccatttctt   3660

cccaagcccg agcagagggt catgcgggcc ccacaggaga agcggccagg gcccgcgggg   3720

ggcaccacct gtggacagcc ctcctgtccc caagctttca ggcaggcact gaaacgcacc   3780

gaacttccac gctctgctgg tcagtggcgg ctgtcccctc cccagcccag ccgcccagcc   3840

acatgtgtct gcctgacccg tacacaccag gggttccggg gttgggagct gaaccatccc   3900

cacctcaggg ttatatttcc ctctcccctt ccctccccgc caagagctct gccaggggcg   3960

ggcaaaaaaa aaagtaaaaa gaaaagaaaa aaaaaaaaaa gaaacaaacc acctctacat   4020

attatggaaa gaaaatattt ttgtcgattc ttattctttt ataattatgc gtggaagaag   4080

tagacacatt aaacgattcc agttggaaac atgtcacctg                        4120
```

<210> SEQ ID NO 39
<211> LENGTH: 819
<212> TYPE: PRT
<213> ORGANISM: Homo sapiens

<400> SEQUENCE: 39

```
Met Arg Lys Val Lys Lys Leu Arg Leu Asp Lys Glu Asn Thr Gly Ser
1               5                   10                  15

Trp Arg Ser Phe Ser Leu Asn Ser Glu Gly Ala Glu Arg Met Ala Thr
            20                  25                  30

Thr Gly Thr Pro Thr Ala Asp Arg Gly Asp Ala Ala Ala Thr Asp Asp
        35                  40                  45

Pro Ala Ala Arg Phe Gln Val Gln Lys His Ser Trp Asp Gly Leu Arg
    50                  55                  60

Ser Ile Ile His Gly Ser Arg Lys Tyr Ser Gly Leu Ile Val Asn Lys
65                  70                  75                  80

Ala Pro His Asp Phe Gln Phe Val Gln Lys Thr Asp Glu Ser Gly Pro
                85                  90                  95

His Ser His Arg Leu Tyr Tyr Leu Gly Met Pro Tyr Gly Ser Arg Glu
            100                 105                 110

Asn Ser Leu Leu Tyr Ser Glu Ile Pro Lys Lys Val Arg Lys Glu Ala
        115                 120                 125

Leu Leu Leu Leu Ser Trp Lys Gln Met Leu Asp His Phe Gln Ala Thr
    130                 135                 140

Pro His His Gly Val Tyr Ser Arg Glu Glu Glu Leu Leu Arg Glu Arg
145                 150                 155                 160

Lys Arg Leu Gly Val Phe Gly Ile Thr Ser Tyr Asp Phe His Ser Glu
                165                 170                 175

Ser Gly Leu Phe Leu Phe Gln Ala Ser Asn Ser Leu Phe His Cys Arg
            180                 185                 190

Asp Gly Gly Lys Asn Gly Phe Met Val Ser Pro Met Lys Pro Leu Glu
        195                 200                 205

Ile Lys Thr Gln Cys Ser Gly Pro Arg Met Asp Pro Lys Ile Cys Pro
    210                 215                 220

Ala Asp Pro Ala Phe Phe Ser Phe Ile Asn Asn Ser Asp Leu Trp Val
225                 230                 235                 240

Ala Asn Ile Glu Thr Gly Glu Glu Arg Arg Leu Thr Phe Cys His Gln
                245                 250                 255

Gly Leu Ser Asn Val Leu Asp Asp Pro Lys Ser Ala Gly Val Ala Thr
            260                 265                 270

Phe Val Ile Gln Glu Glu Phe Asp Arg Phe Thr Gly Tyr Trp Trp Cys
```

-continued

```
        275                 280                 285

Pro Thr Ala Ser Trp Glu Gly Ser Glu Gly Leu Lys Thr Leu Arg Ile
    290                 295                 300

Leu Tyr Glu Glu Val Asp Glu Ser Glu Val Glu Val Ile His Val Pro
305                 310                 315                 320

Ser Pro Ala Leu Glu Glu Arg Lys Thr Asp Ser Tyr Arg Tyr Pro Arg
                325                 330                 335

Thr Gly Ser Lys Asn Pro Lys Ile Ala Leu Lys Leu Ala Glu Phe Gln
            340                 345                 350

Thr Asp Ser Gln Gly Lys Ile Val Ser Thr Gln Glu Lys Glu Leu Val
        355                 360                 365

Gln Pro Phe Ser Ser Leu Phe Pro Lys Val Glu Tyr Ile Ala Arg Ala
    370                 375                 380

Gly Trp Thr Arg Asp Gly Lys Tyr Ala Trp Ala Met Phe Leu Asp Arg
385                 390                 395                 400

Pro Gln Gln Trp Leu Gln Leu Val Leu Leu Pro Pro Ala Leu Phe Ile
                405                 410                 415

Pro Ser Thr Glu Asn Glu Glu Gln Arg Leu Ala Ser Ala Arg Ala Val
            420                 425                 430

Pro Arg Asn Val Gln Pro Tyr Val Val Tyr Glu Glu Val Thr Asn Val
        435                 440                 445

Trp Ile Asn Val His Asp Ile Phe Tyr Pro Phe Pro Gln Ser Glu Gly
    450                 455                 460

Glu Asp Glu Leu Cys Phe Leu Arg Ala Asn Glu Cys Lys Thr Gly Phe
465                 470                 475                 480

Cys His Leu Tyr Lys Val Thr Ala Val Leu Lys Ser Gln Gly Tyr Asp
                485                 490                 495

Trp Ser Glu Pro Phe Ser Pro Gly Glu Asp Glu Phe Lys Cys Pro Ile
            500                 505                 510

Lys Glu Glu Ile Ala Leu Thr Ser Gly Glu Trp Glu Val Leu Ala Arg
        515                 520                 525

His Gly Ser Lys Gly Thr Lys Asp Thr Pro Leu Glu His His Leu Tyr
    530                 535                 540

Val Val Ser Tyr Glu Ala Ala Gly Glu Ile Val Arg Leu Thr Thr Pro
545                 550                 555                 560

Gly Phe Ser His Ser Cys Ser Met Ser Gln Asn Phe Asp Met Phe Val
                565                 570                 575

Ser His Tyr Ser Ser Val Ser Thr Pro Pro Cys Val His Val Tyr Lys
            580                 585                 590

Leu Ser Gly Pro Asp Asp Asp Pro Leu His Lys Gln Pro Arg Phe Trp
        595                 600                 605

Ala Ser Met Met Glu Ala Ala Ser Cys Pro Pro Asp Tyr Val Pro Pro
    610                 615                 620

Glu Ile Phe His Phe His Thr Arg Ser Asp Val Arg Leu Tyr Gly Met
625                 630                 635                 640

Ile Tyr Lys Pro His Ala Leu Gln Pro Gly Lys Lys His Pro Thr Val
                645                 650                 655

Leu Phe Val Tyr Gly Gly Pro Gln Val Gln Leu Val Asn Asn Ser Phe
            660                 665                 670

Lys Gly Ile Lys Tyr Leu Arg Leu Asn Thr Leu Ala Ser Leu Gly Tyr
        675                 680                 685

Ala Val Val Val Ile Asp Gly Arg Gly Ser Cys Gln Arg Gly Leu Arg
    690                 695                 700
```

Phe Glu Gly Ala Leu Lys Asn Gln Met Gly Gln Val Glu Ile Glu Asp
705 710 715 720

Gln Val Glu Gly Leu Gln Phe Val Ala Glu Lys Tyr Gly Phe Ile Asp
725 730 735

Leu Ser Arg Val Ala Ile His Gly Trp Ser Tyr Gly Gly Phe Leu Ser
740 745 750

Leu Met Gly Leu Ile His Lys Pro Gln Val Phe Lys Ala Gln Pro Leu
755 760 765

Ala Tyr Pro Pro Arg Leu Pro Gly Arg Lys Arg Ala Leu Phe Pro His
770 775 780

Lys Leu Pro Arg Leu Pro Thr Asp Pro Ser Arg Glu Thr Leu Pro Ala
785 790 795 800

Pro Asp Leu Pro Gln Arg Glu Thr Gln Tyr Ser Leu Pro Arg Val Gly
805 810 815

Arg Ala Leu

<210> SEQ ID NO 40
<211> LENGTH: 4037
<212> TYPE: DNA
<213> ORGANISM: Homo sapiens

<400> SEQUENCE: 40
caggccgccg cctgggtcgc tcaacttccg ggtcaaaggt gcctgagccg gcgggtcccc 60
tgtgtccgcc gcggctgtcg tccccccgctc ccgccacttc cggggtcgca gtcccgggca 120
tggagccgcg accgtgaggc gccgctggac ccgggacgac ctgcccagtc cggccgccgc 180
cccacgtccc ggtctgtgtc ccacgcctgc agctggaatg gaggctctct ggaccccttta 240 gaaggcaccc ctgccctcct gaggtcagct gagcggttaa tgcggaaggt taagaaactg 300
cgcctggaca aggagaacac cggaagttgg agaagcttct cgctgaattc cgaggggggct 360 gagaggatgg ccaccaccgg gaccccaacg gccgaccgag gcgacgcagc cgccacagat 420
gacccggccg cccgcttcca ggtgcagaag cactcgtggg acgggctccg gagcatcatc 480
cacggcagcc gcaagtactc gggcctcatt gtcaacaagg cgccccacga cttccagttt 540
gtgcagaaga cggatgagtc tgggccccac tcccaccgcc tctactacct gggaatgcca 600
tatggcagcc gagagaactc cctcctctac tctgagattc ccaagaaggt ccggaaagag 660
gctctgctgc tcctgtcctg gaagcagatg ctggatcatt tccaggccac gccccaccat 720
ggggtctact ctcgggagga ggagctgctg agggagcgga aacgcctggg ggtcttcggc 780
atcacctcct acgacttcca cagcgagagt ggcctcttcc tcttccaggc cagcaacagc 840
ctcttccact gccgcgacgg cggcaagaac ggcttcatgg tgtcccctat gaaaccgctg 900
gaaatcaaga cccagtgctc agggccccgg atggacccca aaatctgccc tgccgaccct 960
gccttcttct ccttcatcaa taacagcgac ctgtgggtgg ccaacatcga gacaggcgag 1020
gagcggcggc tgaccttctg ccaccaaggt ttatccaatg tcctggatga ccccaagtct 1080
gcgggtgtgg ccaccttcgt catacaggaa gagttcgacc gcttcactgg gtactggtgg 1140
tgccccacag cctcctggga aggttcagag ggcctcaaga cgctgcgaat cctgtatgag 1200
gaagtcgatg agtccgaggt ggaggtcatt cacgtcccct ctcctgcgct agaagaaagg 1260
aagacggact cgtatcggta ccccaggaca ggcagcaaga atcccaagat tgccttgaaa 1320
ctggctgagt tccagactga cagccagggc aagatcgtct cgacccagga gaaggagctg 1380
gtgcagccct tcagctcgct gttcccgaag gtggagtaca tcgccagggc cgggtggacc 1440

-continued

```
cgggatggca aatacgcctg ggccatgttc ctggaccggc cccagcagtg gctccagctc   1500
gtcctcctcc ccccggccct gttcatcccg agcacagaga atgaggagca gcggctagcc   1560
tctgccagag ctgtccccag gaatgtccag ccgtatgtgg tgtacgagga ggtcaccaac   1620
gtctggatca atgttcatga catcttctat cccttccccc aatcagaggg agaggacgag   1680
ctctgctttc tccgcgccaa tgaatgcaag accggcttct gccatttgta caaagtcacc   1740
gccgttttaa aatcccaggg ctacgattgg agtgagccct tcagccccgg ggaagatgaa   1800
tttaagtgcc ccattaagga agagattgct ctgaccagcg gtgaatggga ggttttggcg   1860
aggcacggct ccaagggcac caaggacacg ccgctggagc accacctcta cgtggtcagc   1920
tatgaggcgg ccggcgagat cgtacgcctc accacgcccg gcttctccca tagctgctcc   1980
atgagccaga acttcgacat gttcgtcagc cactacagca gcgtgagcac gccgccctgc   2040
gtgcacgtct acaagctgag cggccccgac gacgaccccc tgcacaagca gccccgcttc   2100
tgggctagca tgatggaggc agccagctgc cccccggatt atgttcctcc agagatcttc   2160
catttccaca cgcgctcgga tgtgcggctc tacggcatga tctacaagcc ccacgccttg   2220
cagccaggga agaagcaccc caccgtcctc tttgtatatg gaggccccca ggtgcagctg   2280
gtgaataact ccttcaaagg catcaagtac ttgcggctca acacactggc ctccctgggc   2340
tacgccgtgg ttgtgattga cggcaggggc tcctgtcagc gagggcttcg gttcgaaggg   2400
gccctgaaaa accaaatggg ccaggtggag atcgaggacc aggtggaggg cctgcagttc   2460
gtggccgaga agtatggctt catcgacctg agccgagttg ccatccatgg ctggtcctac   2520
gggggcttcc tctcgctcat ggggctaatc cacaagcccc aggtgttcaa ggcccaaccg   2580
cttgcttatc ctccacggct tcctggacga aaacgtgcac tttttccaca caaacttcct   2640
cgtctcccaa ctgatccgag cagggaaacc ttaccagctc cagatctacc ccaacgagag   2700
acacagtatt cgctgccccg agtcgggcga gcactatgaa gtcacgttgc tgcactttct   2760
acaggaatac ctctgagcct gcccaccggg agccgccaca tcacagcaca agtggctgca   2820
gcctccgcgg ggaaccaggc gggagggact gagtggcccg cgggccccag tgaggcactt   2880
tgtcccgccc agcgctggcc agccccgagg agccgctgcc ttcaccgccc cgacgccttt   2940
tatccttttt taaacgctct tgggttttat gtccgctgct tcttggttgc cgagacagag   3000
agatggtggt ctcgggccag cccctcctct ccccgccttc tgggaggagg aggtcacacg   3060
ctgatgggca ctggagaggc cagaagagac tcagaggagc gggctgcctt ccgcctgggg   3120
ctccctgtga cctctcagtc ccctggcccg gccagccacc gtccccagca cccaagcatg   3180
caattgcctg tccccccgg ccagcctccc caacttgatg tttgtgtttt gtttgggggg   3240
atatttttca taattattta aaagacaggc cgggcgcggt ggctcacgtc tgtaatccca   3300
gcactttggg aggctgaggc gggcggatca cctgaggttg ggagttcaag accagcctgg   3360
ccaacatggg gaaaccccgt ctctactaaa aatacaaaaa attagccggg tgtggtggcg   3420
cgtgcctata atcccagcta ctcgggaggc tgaggcagga gaatcgcttg aacccgggag   3480
gtggaggttg cggtgagcca agatcgcacc attgcactcc agcctgggca acaagagcga   3540
aactctgtct caaaataaat aaaaaataaa agacagaaag caaggggtgc ctaaatctag   3600
acttggggtc cacaccgggc agcggggttg caacccagca cctggtaggc tccatttctt   3660
cccaagcccg actttcaggc aggcactgaa acgcaccgaa cttccacgct ctgctggtca   3720
gtggcggctg tcccctcccc agcccagccg cccagccaca tgtgtctgcc tgacccgtac   3780
```

-continued

```
acaccagggg ttccggggtt gggagctgaa ccatccccac ctcagggtta tatttccctc   3840

tccccttccc tccccgccaa gagctctgcc aggggcgggc aaaaaaaaaa gtaaaaagaa   3900

aagaaaaaaa aaaaaaagaa acaaaccacc tctacatatt atggaaagaa aatatttttg   3960

tcgattctta ttcttttata attatgcgtg gaagaagtag acacattaaa cgattccagt   4020

tggaaacatg tcacctg                                                  4037


<210> SEQ ID NO 41
<211> LENGTH: 706
<212> TYPE: PRT
<213> ORGANISM: Homo sapiens

<400> SEQUENCE: 41

Asp Thr Asp Val Val Tyr Lys Ser Glu Asn Gly His Val Ile Lys Leu
1               5                   10                  15

Asn Ile Glu Thr Asn Ala Thr Thr Leu Leu Leu Glu Asn Thr Thr Phe
            20                  25                  30

Val Thr Phe Lys Ala Ser Arg His Ser Val Ser Pro Asp Leu Lys Tyr
        35                  40                  45

Val Leu Leu Ala Tyr Asp Val Lys Gln Ile Phe His Tyr Ser Tyr Thr
    50                  55                  60

Ala Ser Tyr Val Ile Tyr Asn Ile His Thr Arg Glu Val Trp Glu Leu
65                  70                  75                  80

Asn Pro Pro Glu Val Glu Asp Ser Val Leu Gln Tyr Ala Ala Trp Gly
                85                  90                  95

Val Gln Gly Gln Gln Leu Ile Tyr Ile Phe Glu Asn Asn Ile Tyr Tyr
            100                 105                 110

Gln Pro Asp Ile Lys Ser Ser Ser Leu Arg Leu Thr Ser Ser Gly Lys
        115                 120                 125

Glu Glu Ile Ile Phe Asn Gly Ile Ala Asp Trp Leu Tyr Glu Glu Glu
    130                 135                 140

Leu Leu His Ser His Ile Ala His Trp Trp Ser Pro Asp Gly Glu Arg
145                 150                 155                 160

Leu Ala Phe Leu Met Ile Asn Asp Ser Leu Val Pro Thr Met Val Ile
                165                 170                 175

Pro Arg Phe Thr Gly Ala Leu Tyr Pro Lys Gly Lys Gln Tyr Pro Tyr
            180                 185                 190

Pro Lys Ala Gly Gln Val Asn Pro Thr Ile Lys Leu Tyr Val Val Asn
        195                 200                 205

Leu Tyr Gly Pro Thr His Thr Leu Glu Leu Met Pro Pro Asp Ser Phe
    210                 215                 220

Lys Ser Arg Glu Tyr Tyr Ile Thr Met Val Lys Trp Val Ser Asn Thr
225                 230                 235                 240

Lys Thr Val Val Arg Trp Leu Asn Arg Pro Gln Asn Ile Ser Ile Leu
                245                 250                 255

Thr Val Cys Glu Thr Thr Thr Gly Ala Cys Ser Lys Lys Tyr Glu Met
            260                 265                 270

Thr Ser Asp Thr Trp Leu Ser Gln Gln Asn Glu Glu Pro Val Phe Ser
        275                 280                 285

Arg Asp Gly Ser Lys Phe Phe Met Thr Val Pro Val Lys Gln Gly Gly
    290                 295                 300

Arg Gly Glu Phe His His Ile Ala Met Phe Leu Ile Gln Ser Lys Ser
305                 310                 315                 320

Glu Gln Ile Thr Val Arg His Leu Thr Ser Gly Asn Trp Glu Val Ile
```

-continued

```
            325                 330                 335

Lys Ile Leu Ala Tyr Asp Glu Thr Thr Gln Lys Ile Tyr Phe Leu Ser
            340                 345                 350

Thr Glu Ser Ser Pro Arg Gly Arg Gln Leu Tyr Ser Ala Ser Thr Glu
        355                 360                 365

Gly Leu Leu Asn Arg Gln Cys Ile Ser Cys Asn Phe Met Lys Glu Gln
    370                 375                 380

Cys Thr Tyr Phe Asp Ala Ser Phe Ser Pro Met Asn Gln His Phe Leu
385                 390                 395                 400

Leu Phe Cys Glu Gly Pro Arg Val Pro Val Val Ser Leu His Ser Thr
            405                 410                 415

Asp Asn Pro Ala Lys Tyr Phe Ile Leu Glu Ser Asn Ser Met Leu Lys
            420                 425                 430

Glu Ala Ile Leu Lys Lys Lys Ile Gly Lys Pro Glu Ile Lys Ile Leu
        435                 440                 445

His Ile Asp Asp Tyr Glu Leu Pro Leu Gln Leu Ser Leu Pro Lys Asp
    450                 455                 460

Phe Met Asp Arg Asn Gln Tyr Ala Leu Leu Leu Ile Met Asp Glu Glu
465                 470                 475                 480

Pro Gly Gly Gln Leu Val Thr Asp Lys Phe His Ile Asp Trp Asp Ser
            485                 490                 495

Val Leu Ile Asp Met Asp Asn Val Ile Val Ala Arg Phe Asp Gly Arg
            500                 505                 510

Gly Ser Gly Phe Gln Gly Leu Lys Ile Leu Gln Glu Ile His Arg Arg
        515                 520                 525

Leu Gly Ser Val Glu Val Lys Asp Gln Ile Thr Ala Val Lys Phe Leu
    530                 535                 540

Leu Lys Leu Pro Tyr Ile Asp Ser Lys Arg Leu Ser Ile Phe Gly Lys
545                 550                 555                 560

Gly Tyr Gly Gly Tyr Ile Ala Ser Met Ile Leu Lys Ser Asp Glu Lys
            565                 570                 575

Leu Phe Lys Cys Gly Ser Val Val Ala Pro Ile Thr Asp Leu Lys Leu
            580                 585                 590

Tyr Ala Ser Ala Phe Ser Glu Arg Tyr Leu Gly Met Pro Ser Lys Glu
        595                 600                 605

Glu Ser Thr Tyr Gln Ala Ala Ser Val Leu His Asn Val His Gly Leu
    610                 615                 620

Lys Glu Glu Asn Ile Leu Ile Ile His Gly Thr Ala Asp Thr Lys Val
625                 630                 635                 640

His Phe Gln His Ser Ala Glu Leu Ile Lys His Leu Ile Lys Ala Gly
            645                 650                 655

Val Asn Tyr Thr Met Gln Val Tyr Pro Asp Glu Gly His Asn Val Ser
            660                 665                 670

Glu Lys Ser Lys Tyr His Leu Tyr Ser Thr Ile Leu Lys Phe Phe Ser
        675                 680                 685

Asp Cys Leu Lys Glu Glu Ile Ser Val Leu Pro Gln Glu Pro Glu Glu
    690                 695                 700

Asp Glu
705
```

<210> SEQ ID NO 42
<211> LENGTH: 4541
<212> TYPE: DNA
<213> ORGANISM: Homo sapiens -continued

<400> SEQUENCE: 42

```
gkctykgtkg wtsmagatac agatgtggtg tataaaagcg agaatggaca tgtcattaaa     60
ctgaatatag aaacaaatgc taccacatta ttattggaaa acacaacttt tgtaaccttc    120
aaagcatcaa gacattcagt ttcaccagat ttaaaatatg tccttctggc atatgatgtc    180
aaacagattt ttcattattc gtatactgct tcatatgtga tttacaacat acacactagg    240
gaagtttggg agttaaatcc tccagaagta gaggactccg tcttgcagta cgcggcctgg    300
ggtgtccaag ggcagcagct gatttatatt tttgaaaata atatctacta tcaacctgat    360
ataaagagca gttcattgcg actgacatct tctggaaaag aagaaataat ttttaatggg    420
attgctgact ggttatatga agaggaactc ctgcattctc acatcgccca ctggtggtca    480
ccagatggag aaagacttgc cttcctgatg ataaatgact ctttggtacc caccatggtt    540
atccctcggt ttactggagc gttgtatccc aaaggaaagc agtatccgta tcctaaggca    600
ggtcaagtga acccaacaat aaaattatat gttgtaaacc tgtatggacc aactcacact    660
ttggagctca tgccacctga cagctttaaa tcaagagaat actatatcac tatggttaaa    720
tgggtaagca ataccaagac tgtggtaaga tggttaaacc gacctcagaa catctccatc    780
ctcacagtct gtgagaccac tacaggtgct tgtagtaaaa aatatgagat gacatcagat    840
acgtggctct ctcagcagaa tgaggagccc gtgttttcta gagacggcag caaattcttt    900
atgacagtgc ctgttaagca agggggacgt ggagaatttc accacatagc tatgttcctc    960
atccagagta aaagtgagca aattaccgtg cggcatctga catcaggaaa ctgggaagtg   1020
ataaagatct tggcatacga tgaaactact caaaaaattt actttctgag cactgaatct   1080
tctcccagag gaaggcagct gtacagtgct tctactgaag gattattgaa tcgccaatgc   1140
atttcatgta atttcatgaa agaacaatgt acatattttg atgccagttt tagtcccatg   1200
aatcaacatt tcttattatt ctgtgaaggt ccaagggtcc cagtggtcag cctacatagt   1260
acggacaacc cagcaaaata ttttatattg gaaagcaatt ctatgctgaa ggaagctatc   1320
ctgaagaaga agataggaaa gccagaaatt aaaatccttc atattgacga ctatgaactt   1380
cctttacagt tgtcccttcc caaagatttt atggaccgaa accagtatgc tcttctgtta   1440
ataatggatg aagaaccagg aggccagctg gttacagata agttccatat tgactgggat   1500
tccgtactca ttgacatgga taatgtcatt gtagcaagat ttgatggcag aggaagtgga   1560
ttccagggtc tgaaaatttt gcaggagatt catcgaagat taggttcagt agaagtaaag   1620
gaccaaataa cagctgtgaa atttttgctg aaactgcctt acattgactc caaaagatta   1680
agcatttttg gaaagggtta tggtggctat attgcatcaa tgatcttaaa atcagatgaa   1740
aagcttttta aatgtggatc cgtggttgca cctatcacag acttgaaatt gtatgcctca   1800
gctttctctg aaagatacct tgggatgcca tctaaggaag aaagcactta ccaggcagcc   1860
agtgtgctac ataatgttca tggcttgaaa gaagaaaata tattaataat tcatggaact   1920
gctgacacaa aagttcattt ccaacactca gcagaattaa tcaagcacct aataaaagct   1980
ggagtgaatt atactatgca ggtctaccca gatgaaggtc ataacgtatc tgagaagagc   2040
aagtatcatc tctacagcac aatcctcaaa ttcttcagtg attgtttgaa ggaagaaata   2100
tctgtgctac cacaggaacc agaagaagat gaataatgga ccgtatttat acagaactga   2160
agggaatatt gaggctcaat gaaacctgac aaagagactg taatattgta gttgctccag   2220
aatgtcaagg gcagcttacg gagatgtcac tggagcagca cgctcagaga cagtgaacta   2280
```

-continued

```
gcatttgaat acacaagtcc aagtctactg tgttgctagg ggtgcagaac ccgtttcttt   2340
gtatgagaga ggtcaaaggg ttggtttcct gggagaaatt agttttgcat taaagtagga   2400
gtagtgcatg ttttcttctg ttatccccct gtttgttctg taactagttg ctctcatttt   2460
aatttcactg gccaccatca tctttgcata taatgcacaa tctatcatct gtcctacagt   2520
ccctgatctt tcatggctga gctgcaatct aacactttac tgtaccttta taataagtgc   2580
aattctttca ttgtctatta ttatgcttaa gaaaatattc agttaataaa aaacagagta   2640
ttttatgtaa tttctgtttt taaaaagaca ttattaaatg ggtcaaagga catatagaaa   2700
tgtggatttc agcaccttcc aaagttcagc cagttatcag tagatacaat atctttaaat   2760
gaacacacga gtgtatgtct cacaatatat atacacaagt gtgcatatac agttaatgaa   2820
actatcttta aatgttattc atgctataaa gagtaaacgt ttgatgaatt agaagagatg   2880
ctcttttcca agctataatg gatgctttgt ttaatgagcc aaatatgatg aaacattttt   2940
tccaattcaa attctagcta ttgctttcct ataaatgttt gggttgtgtt tggtattgtt   3000
tttagtggtt aatagttttc cagttgcatt taatttttg aatatgatac cttgtcacat    3060
gtaaattaga tacttaaata ttaaattata gtttctgata aagaaatttt gttaacaatg   3120
caatgccact gagtgctatt ttgctctttt ggtggagaag gctttttca aaactcttgg    3180
tccttttact tctttctctc agtgcagaat caattctcat tttcatcgta aaagcaaata   3240
gctggattat ttcatttgcc agtttctatt tagtattcca tgcctgccca attcatctgt   3300
tactgtttaa tttcaattct tctggtgaga attagaaatg aaatattttt tattcattgg   3360
ccaaaaagtt cacagacagc agtgtttgct atttactttg aattgaaggc acaaaatgca   3420
tcaattcctg tgctgtgttg acttgcagta gtaagtaact gagagcataa aataaacctg   3480
actgtatgaa gtcaatttaa gtgatgagaa catttaactt tggtgactaa agtcagaata   3540
tcttctcact tcacttaagg gatcttccag aagatatcta aaagtctgta ataagcttag   3600
aagttcagat aaatctaggc aggatactgc atttttgtgg ttttaaaaaa gtccttagga   3660
cagactgaat tatcataact tatggcatca ggaggaaact ttaaaatatc aaggaatcac   3720
tcagtcaccc tcctgttttg ttgaaggatc aaccccaaat tctgggtatt tgagtacatg   3780
tgaatcatgg atttggtatt caactttttc cctggatgct ttggaatcgt gtcttccatg   3840
ctccactggg ttcaatttaa aataggagag gctttctctt ctgaaagatc cattttaggt   3900
ctttttcaag aatagtgaac acatttttta acaaaataag ttgtaatttt aaaaggaaag   3960
ttttgcctat tttattaaga tggaaatttc tttttaggct aatttgaaat ccaactgaag   4020
ctttttaacc aatattttaa atttgaacca ctagagtttt ttatgatgca aatgattatg   4080
ttgtctgaaa ggtgtggttt tattgaatgt ctatttgagt atcatttaaa aagtatttgc   4140
cttttactgt catcatttct cttgttttat tattattatc aatgtttatc tatttttcaa   4200
ttaatttaat acagtttcta atgtgaaaga catttttctg gaacccgttt tccccttaaa   4260
cactaaagag acctcaagtg aaagcatatt gcttagtagg aaggtagaaa atgttaatcc   4320
ctgcgattct ttgagtttta atgacagggt cattttcagt aaaggaaatg ctcaccaaca   4380
catagtcacc aactattaaa ggaatcatgt gattggattt tcccctgtat acatgtaccc   4440
ttggtcataa tcccactatt tcatacatat ttatgcattg ctagattttc ctaggactcc   4500
aatagcatgc tttccaagtg ttattattcc cttaatgtta a                       4541
```

<210> SEQ ID NO 43
<211> LENGTH: 691

-continued

<212> TYPE: PRT
<213> ORGANISM: Homo sapiens

<400> SEQUENCE: 43

```
Asp Thr Asp Val Val Tyr Lys Ser Glu Asn Gly His Val Ile Lys Leu
1               5                   10                  15

Asn Ile Glu Thr Asn Ala Thr Thr Leu Leu Leu Glu Asn Thr Thr Phe
            20                  25                  30

Val Thr Phe Lys Ala Ser Arg His Ser Val Ser Pro Asp Leu Lys Tyr
        35                  40                  45

Val Leu Leu Ala Tyr Asp Val Lys Gln Ile Phe His Tyr Ser Tyr Thr
    50                  55                  60

Ala Ser Tyr Val Ile Tyr Asn Ile His Thr Arg Glu Val Trp Glu Leu
65                  70                  75                  80

Asn Pro Pro Glu Val Glu Asp Ser Val Leu Gln Tyr Ala Ala Trp Gly
                85                  90                  95

Val Gln Gly Gln Gln Leu Ile Tyr Ile Phe Glu Asn Asn Ile Tyr Tyr
            100                 105                 110

Gln Pro Asp Ile Lys Ser Ser Ser Leu Arg Leu Thr Ser Ser Gly Lys
        115                 120                 125

Glu Glu Ile Ile Phe Asn Gly Ile Ala Asp Trp Leu Tyr Glu Glu Glu
    130                 135                 140

Leu Leu His Ser His Ile Ala His Trp Trp Ser Pro Asp Gly Glu Arg
145                 150                 155                 160

Leu Ala Phe Leu Met Ile Asn Asp Ser Leu Val Pro Thr Met Val Ile
                165                 170                 175

Pro Arg Phe Thr Gly Ala Leu Tyr Pro Lys Gly Lys Gln Tyr Pro Tyr
            180                 185                 190

Pro Lys Ala Gly Gln Val Asn Pro Thr Ile Lys Leu Tyr Val Val Asn
        195                 200                 205

Leu Tyr Gly Pro Thr His Thr Leu Glu Leu Met Pro Pro Asp Ser Phe
    210                 215                 220

Lys Ser Arg Glu Tyr Tyr Ile Thr Met Val Lys Trp Val Ser Asn Thr
225                 230                 235                 240

Lys Thr Val Val Arg Trp Leu Asn Arg Pro Gln Asn Ile Ser Ile Leu
                245                 250                 255

Thr Val Cys Glu Thr Thr Thr Gly Ala Cys Ser Lys Lys Tyr Glu Met
            260                 265                 270

Thr Ser Asp Thr Trp Leu Ser Gln Gln Asn Glu Glu Pro Val Phe Ser
        275                 280                 285

Arg Asp Gly Ser Lys Phe Phe Met Thr Val Pro Val Lys Gln Gly Gly
    290                 295                 300

Arg Gly Glu Phe His His Ile Ala Met Phe Leu Ile Gln Ser Lys Ser
305                 310                 315                 320

Glu Gln Ile Thr Val Arg His Leu Thr Ser Gly Asn Trp Glu Val Ile
                325                 330                 335

Lys Ile Leu Ala Tyr Asp Glu Thr Thr Gln Lys Ile Ser Ala Ser Thr
            340                 345                 350

Glu Gly Leu Leu Asn Arg Gln Cys Ile Ser Cys Asn Phe Met Lys Glu
        355                 360                 365

Gln Cys Thr Tyr Phe Asp Ala Ser Phe Ser Pro Met Asn Gln His Phe
    370                 375                 380

Leu Leu Phe Cys Glu Gly Pro Arg Val Pro Val Val Ser Leu His Ser
385                 390                 395                 400
```

-continued

```
Thr Asp Asn Pro Ala Lys Tyr Phe Ile Leu Glu Ser Asn Ser Met Leu
                405                 410                 415

Lys Glu Ala Ile Leu Lys Lys Lys Ile Gly Lys Pro Glu Ile Lys Ile
            420                 425                 430

Leu His Ile Asp Asp Tyr Glu Leu Pro Leu Gln Leu Ser Leu Pro Lys
        435                 440                 445

Asp Phe Met Asp Arg Asn Gln Tyr Ala Leu Leu Leu Ile Met Asp Glu
    450                 455                 460

Glu Pro Gly Gly Gln Leu Val Thr Asp Lys Phe His Ile Asp Trp Asp
465                 470                 475                 480

Ser Val Leu Ile Asp Met Asp Asn Val Ile Val Ala Arg Phe Asp Gly
                485                 490                 495

Arg Gly Ser Gly Phe Gln Gly Leu Lys Ile Leu Gln Glu Ile His Arg
            500                 505                 510

Arg Leu Gly Ser Val Glu Val Lys Asp Gln Ile Thr Ala Val Lys Phe
        515                 520                 525

Leu Leu Lys Leu Pro Tyr Ile Asp Ser Lys Arg Leu Ser Ile Phe Gly
    530                 535                 540

Lys Gly Tyr Gly Gly Tyr Ile Ala Ser Met Ile Leu Lys Ser Asp Glu
545                 550                 555                 560

Lys Leu Phe Lys Cys Gly Ser Val Val Ala Pro Ile Thr Asp Leu Lys
                565                 570                 575

Leu Tyr Ala Ser Ala Phe Ser Glu Arg Tyr Leu Gly Met Pro Ser Lys
            580                 585                 590

Glu Glu Ser Thr Tyr Gln Ala Ala Ser Val Leu His Asn Val His Gly
        595                 600                 605

Leu Lys Glu Glu Asn Ile Leu Ile Ile His Gly Thr Ala Asp Thr Lys
    610                 615                 620

Val His Phe Gln His Ser Ala Glu Leu Ile Lys His Leu Ile Lys Ala
625                 630                 635                 640

Gly Val Asn Tyr Thr Met Gln Val Tyr Pro Asp Glu Gly His Asn Val
                645                 650                 655

Ser Glu Lys Ser Lys Tyr His Leu Tyr Ser Thr Ile Leu Lys Phe Phe
            660                 665                 670

Ser Asp Cys Leu Lys Glu Glu Ile Ser Val Leu Pro Gln Glu Pro Glu
        675                 680                 685

Glu Asp Glu
    690
```

```
<210> SEQ ID NO 44
<211> LENGTH: 4496
<212> TYPE: DNA
<213> ORGANISM: Homo sapiens

<400> SEQUENCE: 44

gkctykgtkg wtsmagatac agatgtggtg tataaaagcg agaatggaca tgtcattaaa      60

ctgaatatag aaacaaatgc taccacatta ttattggaaa acacaacttt tgtaaccttc     120

aaagcatcaa gacattcagt ttcaccagat ttaaaatatg tccttctggc atatgatgtc     180

aaacagattt ttcattattc gtatactgct tcatatgtga tttacaacat acacactagg     240

gaagtttggg agttaaatcc tccagaagta gaggactccg tcttgcagta cgcggcctgg     300

ggtgtccaag ggcagcagct gatttatatt tttgaaaata atatctacta tcaacctgat     360

ataaagagca gttcattgcg actgacatct tctggaaaag aagaaataat ttttaatggg     420
```

-continued

```
attgctgact ggttatatga agaggaactc ctgcattctc acatcgccca ctggtggtca    480
ccagatggag aaagacttgc cttcctgatg ataaatgact ctttggtacc caccatggtt    540
atccctcggt ttactggagc gttgtatccc aaaggaaagc agtatccgta tcctaaggca    600
ggtcaagtga acccaacaat aaaattatat gttgtaaacc tgtatggacc aactcacact    660
ttggagctca tgccacctga cagctttaaa tcaagagaat actatatcac tatggttaaa    720
tgggtaagca ataccaagac tgtggtaaga tggttaaacc gacctcagaa catctccatc    780
ctcacagtct gtgagaccac tacaggtgct tgtagtaaaa aatatgagat gacatcagat    840
acgtggctct ctcagcagaa tgaggagccc gtgttttcta gagacggcag caaattcttt    900
atgacagtgc ctgttaagca agggggacgt ggagaatttc accacatagc tatgttcctc    960
atccagagta aaagtgagca aattaccgtg cggcatctga catcaggaaa ctgggaagtg   1020
ataaagatct tggcatacga tgaaactact caaaaaatca gtgcttctac tgaaggatta   1080
ttgaatcgcc aatgcatttc atgtaatttc atgaaagaac aatgtacata ttttgatgcc   1140
agttttagtc ccatgaatca acatttctta ttattctgtg aaggtccaag ggtcccagtg   1200
gtcagcctac atagtacgga caacccagca aaatatttta tattggaaag caattctatg   1260
ctgaaggaag ctatcctgaa gaagaagata ggaaagccag aaattaaaat ccttcatatt   1320
gacgactatg aacttccttt acagttgtcc cttcccaaag attttatgga ccgaaaccag   1380
tatgctcttc tgttaataat ggatgaagaa ccaggaggcc agctggttac agataagttc   1440
catattgact gggattccgt actcattgac atggataatg tcattgtagc aagatttgat   1500
ggcagaggaa gtggattcca gggtctgaaa attttgcagg agattcatcg aagattaggt   1560
tcagtagaag taaaggacca aataacagct gtgaaatttt tgctgaaact gccttacatt   1620
gactccaaaa gattaagcat ttttggaaag ggttatggtg gctatattgc atcaatgatc   1680
ttaaaatcag atgaaaagct tttaaatgt ggatccgtgg ttgcacctat cacagacttg   1740
aaattgtatg cctcagcttt ctctgaaaga taccttggga tgccatctaa ggaagaaagc   1800
acttaccagg cagccagtgt gctacataat gttcatggct tgaaagaaga aaatatatta   1860
ataattcatg gaactgctga cacaaaagtt catttccaac actcagcaga attaatcaag   1920
cacctaataa aagctggagt gaattatact atgcaggtct acccagatga aggtcataac   1980
gtatctgaga agagcaagta tcatctctac agcacaatcc tcaaattctt cagtgattgt   2040
ttgaaggaag aaatatctgt gctaccacag gaaccagaag aagatgaata atggaccgta   2100
tttatacaga actgaaggga atattgaggc tcaatgaaac ctgacaaaga gactgtaata   2160
ttgtagttgc tccagaatgt caagggcagc ttacggagat gtcactggag cagcacgctc   2220
agagacagtg aactagcatt tgaatacaca agtccaagtc tactgtgttg ctaggggtgc   2280
agaacccgtt tctttgtatg agagaggtca aagggttggt ttcctgggag aaattagttt   2340
tgcattaaag taggagtagt gcatgttttc ttctgttatc cccctgtttg ttctgtaact   2400
agttgctctc attttaattt cactggccac catcatcttt gcatataatg cacaatctat   2460
catctgtcct acagtccctg atctttcatg gctgagctgc aatctaacac tttactgtac   2520
ctttataata agtgcaattc tttcattgtc tattattatg cttaagaaaa tattcagtta   2580
ataaaaaaca gagtatttta tgtaatttct gtttttaaaa agacattatt aaatgggtca   2640
aaggacatat agaaatgtgg atttcagcac cttccaaagt tcagccagtt atcagtagat   2700
acaatatctt taaatgaaca cacgagtgta tgtctcacaa tatatataca caagtgtgca   2760
```

-continued

```
tatacagtta atgaaactat ctttaaatgt tattcatgct ataaagagta aacgtttgat   2820

gaattagaag agatgctctt ttccaagcta taatggatgc tttgtttaat gagccaaata   2880

tgatgaaaca tttttttccaa ttcaaattct agctattgct ttcctataaa tgtttgggtt   2940

gtgtttggta ttgtttttag tggttaatag ttttccagtt gcatttaatt ttttgaatat   3000

gataccttgt cacatgtaaa ttagatactt aaatattaaa ttatagtttc tgataaagaa   3060

attttgttaa caatgcaatg ccactgagtg ctattttgct cttttggtgg agaaggcttt   3120

tttcaaaact cttggtcctt ttacttcttt ctctcagtgc agaatcaatt ctcattttca   3180

tcgtaaaagc aaatagctgg attatttcat ttgccagttt ctatttagta ttccatgcct   3240

gcccaattca tctgttactg tttaatttca attcttctgg tgagaattag aaatgaaata   3300

ttttttattc attggccaaa aagttcacag acagcagtgt ttgctattta ctttgaattg   3360

aaggcacaaa atgcatcaat tcctgtgctg tgttgacttg cagtagtaag taactgagag   3420

cataaaataa acctgactgt atgaagtcaa tttaagtgat gagaacattt aactttggtg   3480

actaaagtca gaatatcttc tcacttcact taagggatct tccagaagat atctaaaagt   3540

ctgtaataag cttagaagtt cagataaatc taggcaggat actgcatttt tgtggtttta   3600

aaaaagtcct taggacagac tgaattatca taacttatgg catcaggagg aaactttaaa   3660

atatcaagga atcactcagt caccctcctg ttttgttgaa ggatcaaccc caaattctgg   3720

gtatttgagt acatgtgaat catggatttg gtattcaact ttttccctgg atgctttgga   3780

atcgtgtctt ccatgctcca ctgggttcaa tttaaaatag gagaggcttt ctcttctgaa   3840

agatccattt taggtctttt tcaagaatag tgaacacatt ttttaacaaa ataagttgta   3900

attttaaaag gaaagttttg cctattttat taagatggaa atttcttttt aggctaattt   3960

gaaatccaac tgaagctttt taaccaatat tttaaatttg aaccactaga gttttttatg   4020

atgcaaatga ttatgttgtc tgaaaggtgt ggttttattg aatgtctatt tgagtatcat   4080

ttaaaaagta tttgcctttt actgtcatca tttctcttgt tttattatta ttatcaatgt   4140

ttatctattt ttcaattaat ttaatacagt ttctaatgtg aaagacattt ttctggaacc   4200

cgttttcccc ttaaacacta aagagacctc aagtgaaagc atattgctta gtaggaaggt   4260

agaaaatgtt aatccctgcg attctttgag ttttaatgac agggtcattt tcagtaaagg   4320

aaatgctcac caacacatag tcaccaacta ttaaaggaat catgtgattg gattttcccc   4380

tgtatacatg tacccttggt cataatccca ctatttcata catatttatg cattgctaga   4440

ttttcctagg actccaatag catgctttcc aagtgttatt attcccttaa tgttaa       4496
```

```
<210> SEQ ID NO 45
<211> LENGTH: 29
<212> TYPE: DNA
<213> ORGANISM: Homo sapiens

<400> SEQUENCE: 45

cggtaccatg gcagcagcaa tggaaacag                                        29


<210> SEQ ID NO 46
<211> LENGTH: 39
<212> TYPE: DNA
<213> ORGANISM: Homo sapiens

<400> SEQUENCE: 46

ggagctcgcg gccgctcata tcacttttag agcagcaat                             39
```

-continued

<210> SEQ ID NO 47
<211> LENGTH: 27
<212> TYPE: DNA
<213> ORGANISM: Homo sapiens

<400> SEQUENCE: 47
caagctttat cacttttaga gcagcaa 27

<210> SEQ ID NO 48
<211> LENGTH: 22
<212> TYPE: DNA
<213> ORGANISM: Homo sapiens

<400> SEQUENCE: 48
cacattcttg ctgcatcagt ca 22

<210> SEQ ID NO 49
<211> LENGTH: 22
<212> TYPE: DNA
<213> ORGANISM: Homo sapiens

<400> SEQUENCE: 49
ttgggtcatc ttcaggactt ga 22

<210> SEQ ID NO 50
<211> LENGTH: 27
<212> TYPE: DNA
<213> ORGANISM: Homo sapiens

<400> SEQUENCE: 50
caagcttacc atggccacca ccgggac 27

<210> SEQ ID NO 51
<211> LENGTH: 37
<212> TYPE: DNA
<213> ORGANISM: Homo sapiens

<400> SEQUENCE: 51
cggatccgcg gccgctcaga ggtattcctg tagaaag 37

<210> SEQ ID NO 52
<211> LENGTH: 27
<212> TYPE: DNA
<213> ORGANISM: Homo sapiens

<400> SEQUENCE: 52
cggatccagg tattcctgta gaaagtg 27

<210> SEQ ID NO 53
<211> LENGTH: 20
<212> TYPE: DNA
<213> ORGANISM: Homo sapiens

<400> SEQUENCE: 53
tacgccgtgg ttgtgattga 20

<210> SEQ ID NO 54
<211> LENGTH: 20
<212> TYPE: DNA
<213> ORGANISM: Homo sapiens

<400> SEQUENCE: 54
ccatacttct cggccacgaa 20

-continued

<210> SEQ ID NO 55
<211> LENGTH: 19
<212> TYPE: DNA
<213> ORGANISM: Homo sapiens

<400> SEQUENCE: 55
gcctgggatt gtgcactgt 19

<210> SEQ ID NO 56
<211> LENGTH: 29
<212> TYPE: DNA
<213> ORGANISM: Homo sapiens

<400> SEQUENCE: 56
gtgtattcaa atgctagttc actgtctct 29

<210> SEQ ID NO 57
<211> LENGTH: 22
<212> TYPE: DNA
<213> ORGANISM: Homo sapiens

<400> SEQUENCE: 57
agctagcact gtccagggtc ct 22

<210> SEQ ID NO 58
<211> LENGTH: 25
<212> TYPE: DNA
<213> ORGANISM: Homo sapiens

<400> SEQUENCE: 58
agggcccttc atcttcttct ggttc 25

<210> SEQ ID NO 59
<211> LENGTH: 19
<212> TYPE: PRT
<213> ORGANISM: Homo sapiens

<400> SEQUENCE: 59

Val Glu Asp Asp Val Met Glu Arg Gln Arg Leu Ile Glu Ser Val Pro
1 5 10 15

Asp Ser Val

<210> SEQ ID NO 60
<211> LENGTH: 19
<212> TYPE: PRT
<213> ORGANISM: Homo sapiens

<400> SEQUENCE: 60

Ser Thr Glu Asn Glu Glu Gln Arg Leu Ala Ser Ala Arg Ala Val Pro
1 5 10 15

Arg Asn Val

<210> SEQ ID NO 61
<211> LENGTH: 15
<212> TYPE: PRT
<213> ORGANISM: Homo sapiens

<400> SEQUENCE: 61

Lys Glu Ala Ile Leu Lys Lys Lys Ile Gly Lys Pro Glu Ile Lys
1 5 10 15

SERINE PROTEASE GENES RELATED TO DPPIV

This application claims priority from U.S. provisional application Ser. No. 60/240,117, filed Oct. 12, 2000, the disclosure of which application is expressly incorporated by reference.

FIELD OF THE INVENTION

The present invention relates to novel serine proteases related to dipeptidyl peptidase IV (DPPIV), and to isolated nucleic acids coding for these proteases, all of which are useful for the discovery of new therapeutic agents, for measuring protease activity, and for determining the inhibitory activity of compounds against these proteases.

BACKGROUND OF THE INVENTION

Proteases and peptidases are enzymes that catalyse the hydrolysis of peptidic amide bonds. Proteases play an important role in the regulation of biological processes in almost every life-form from bacteria to virus to mammals. They perform critical functions in, for example, digestion, blood clotting, apoptosis, activation of immune responses, zymogen activation, viral maturation, protein secretion and protein trafficking. They can be classified according to a number of criteria, such as site of action, substrate preference, and mechanism. So, for example, aminopeptidases act preferentially at the N-terminal residues of a peptide, while carboxypeptidases act preferentially at the C-terminus and endopeptidases act at sites removed from the two termini. Among the carboxy- and aminopeptidases, peptidyl peptidases cleave a single amino acid residue from the substrate, dipeptidyl peptidases cleave a dipeptide unit (two amino acids) from the substrate, and tripeptidases cleave three amino acids from the substrate. Substrate preference is frequently expressed in terms of the amino acid residue immediately N-terminal to the cleavage site. For example, trypsin-like peptidases will preferentially cleave a peptide next to a basic amino acid (arginine or lysine), i.e. where the bond hydrolysed is the Arg/Lys-Xaa bond. As another example, the chymotrypsin-like family of peptidases preferentially hydrolyse peptides adjacent to an aromatic residue. Mechanistically, peptidases are classified as being serine-dependent, cysteine-dependent, aspartic acid-dependent or zinc-dependent.

Because peptidases and proteases are involved in the regulation of many physiological processes, they are attractive targets for the development of therapeutic agents. Protease and peptidase inhibitors are, for example, used in the treatment of hypertension, coagulation disorders, and viral infection.

Proteolytic enzymes that exploit serine in their catalytic activity are ubiquitous, being found in viruses, bacteria and eukaryotes. Over 20 families (denoted S1–S27) of serine protease have been identified; these are grouped into 6 clans (SA, SB, SC, SE, SF and SG) on the basis of structural similarity and other functional evidence. Structures are known for four of the clans (SA, SB, SC and SE); these appear to be totally unrelated, suggesting at least four evolutionary origins of serine peptidases and possibly many more, Rawlings and Barrett, *Meth. Enzymol.* 244: 19–61 (1994).

The prolyl oligopeptidase family consists of a number of evolutionarily related peptidases whose catalytic activity seems to be provided by a charge relay system similar to that of the trypsin family of serine proteases, but which evolved by independent convergent evolution. A conserved serine residue has been shown experimentally (in *E. coli* protease II as well as in pig and bacterial PE) to be necessary for the catalytic mechanism. This serine, which is part of the catalytic triad (Ser, His, Asp), is generally located about 150 residues away from the C-terminal extremity of these enzymes (which are all proteins that contains about 700 to 800 amino acids).

One of the most intensively studied prolyl oligopeptidases is dipeptidyl peptidase IV (DPPIV, EC 3.414.5), a type II glycoprotein, which is the only well characterised dipeptidyl aminopeptidase known to be located on the outer side of plasma membranes. As indicated above, dipeptidyl aminopeptidases are characterised by their ability to cleave N-terminal dipeptides from a variety of small peptides. Dipeptidyl aminopeptidases show different substrate specificities and cellular localisation, suggesting different functions of each activity in peptide processing. DPPIV is characterised by its capacity to cleave N-terminal dipeptides containing proline or alanine as the penultimate residue. The DPPIV gene spans approximately 70 kb and contains 26 exons, ranging in size from 45 bp to 1.4 kb. The nucleotide sequence (3,465 bp) of the cDNA contains an open reading frame encoding a polypeptide comprising 766 amino acids. The nucleotides that encode the active site sequence (G-W-S-Y-G) are split between 2 exons. This clearly distinguishes the genomic organisation of the prolyl oligopeptidase family from that of the classic serine protease family.

DPPIV is widely distributed in mammalian tissues and is found in great abundance in the kidney, intestinal epithelium and placenta (Yaron, A. and Naider, F., Critical Reviews in *Biochem. Mol. Biol.* 1993 [1], 31). In the human immune system, the enzyme is expressed almost exclusively by activated T-lymphocytes of the $CD4^+$ type where the enzyme has been shown to be synonymous with the cell-surface antigen CD26. Although the exact role of DP-IV in human physiology is still not completely understood, recent research has shown that the enzyme clearly has a major role in human physiology and pathophysiology.

On human T cells, DPPIV expression appears late in thymic differentiation and is preferentially restricted to the $CD4^+$ helper/memory population, and CD26 can deliver a potent co-stimulatory T-cell activation signal. DPPIV, also known as T-cell activation antigen CD26, therefore plays an important role in the immune response via association with CD45 tyrosine phosphatase and, through its ability to bind adenosine deaminase (ADA) to the T-cell surface, protects the T-cell from adenosine-mediated inhibition of proliferation. Furthermore, the regulation of the function of chemokines by CD26/DPPIV appears to be essential for lymphocyte trafficking and infectivity of HIV strains. DPPIV has been associated with numerous functions including involvement in T-cell activation, cell adhesion, digestion of proline containing peptides in the kidney and intestines, HIV infection and apoptosis, and regulation of tumorigenicity in certain melanoma cells, Pethiyagoda et al., *Clin. Exp. Metastasis* 2000;18(5):391–400. DPPIV is also implicated in the endocrine regulation and metabolic physiology. More particularly, DPPIV cleaves the amino-terminal His-Ala dipeptide of GLP-1, generating a GLP-1 receptor antagonist, and thereby shortens the physiological response to GLP-1. Glucagon-like peptide-1 (GLP-1), an incretin that induces glucose-dependent insulin secretion, is rapidly degraded by DPPIV, and since the half-life for DPPIV cleavage is much shorter than the half-life for removal of GLP-1 from circulation, a significant increase in GLP-1 bioactivity (5- to 10- fold) is anticipated from DPP-IV inhibition. Inhibitors of DPPIV are currently being studied in the clinic as potential therapeutic agents for type 2 diabetes and impaired glucose tolerance.

Various different inhibitors of DPPIV were known in 1993. One of these is a suicide inhibitor N-Ala-Pro-O-(nitrobenzoyl-) hydroxylamine. Another is a competitive inhibitor: e-(4-nitro) benzoxycarbonyl-Lys-Pro, and another is a polyclonal rabbit anti-porcine kidney DPPIV immunoglobulin. Others have since been developed and are described in detail in U.S. Pat. Nos. 5,939,560, 6,110,949, 6,011,155 and 5,462,928.

In addition to, but independent of, its serine type catalytic activity, DPPIV binds closely to the soluble extracellular enzyme adenosine deaminase (ADA), acting as a receptor and is thought to mediate signal transduction. DPPIV structure is characterized by two extracellular domains, an $\alpha/\beta$ fold hydrolase domain and a 7-blade beta-propeller domain consisting of repeated beta sheets of about 50 amino acids. Recently it has been shown that, besides selecting substrates by size, the beta-propeller domain, containing 10 of the 12 highly conserved cysteine residues, contributes to catalysis of the peptidase domain. In addition, the cysteine-rich domain is responsible for DPPIV-binding to collagen I and to extracellular ADA. DPPIV is also reported to play a role in fibronectin-mediated interactions of cells with extracellular matrix. Recent studies show that the protease activity of DPPIV is not required for its anti-invasive activity because mutants of DPPIV that lack the extracellular serine protease activity maintain such activity.

A number of proteins that share similarities with DPPIV have been reported in the literature. Several of these proteins have been cloned including DPP-I, DPP-II, DPP-III, DPP-X and fibroblast activation protein (FAP). These have been identified and characterised either by molecular cloning and functional studies of expressed proteins or as biochemical activities in tissue extracts. DPPIV-beta and other novel peptidases with functional similarities to DPPIV are not yet cloned. The identification, characterization and/or appropriate classification of further members of the family of prolyl oligopeptidases, the elucidation of their physiological (and particularly pathophysiological) role, and the application of that knowledge to the development of new therapeutic agents are significant challenges.

SUMMARY OF THE INVENTION

The present invention provides proteins with prolyloligopeptidase (post-proline cleaving) activities that constitute three novel members of a family of proteins related to DPPIV, including the full-length proteins, alternative splice forms, subunits, and mutants, as well as nucleotide sequences encoding the same. The present invention also provides methods of screening for substrates, interacting proteins, agonists, antagonists or inhibitors of the above proteins, and furthermore to pharmaceutical compositions comprising the proteins and/or mutants, derivatives and/or analogues thereof and/or ligands thereto.

These novel proteins having significant sequence homology to DPPIV are termed dipeptidyl peptidase IV-related protein-1, 2 & 3 (DPRP-1, DPRP-2 and DPRP-3). The amino acid sequences of DPRP-1, DPRP-2 and DPRP-3 are given in SEQ. ID NOS:1, 3 and 5 respectively. Further disclosed are nucleic acid sequences coding for these proteins (SEQ. ID NOS:2, 4 and 6). Table 1 illustrates the homology (i.e. similarity) between the novel proteins DPRP-1, DPRP-2 and DPRP-3 and other known serine proteases.

TABLE 1

Comparison of the sequences of these three novel proteins with DPPIV and other Clan SC, Family S9 members and Subfamily B members

| Protease Family | Protease name | No. of a.a. | Homology with DPPIV | TM region | Ser-Asp-His Triad | Gene location | Optimal pH |
|---|---|---|---|---|---|---|---|
| Clan CA, Family C1 | DPPI | 463 | N | N | N | 11q14.1-q14.3 | — |
| Clan SC, | DPPII | 500 | N | Y | N | — | 4.5–6.0 |
| Family S28 | QPP | 492 | N | N | N | — | 4.5–7.5 |
| | PCP | 496 | N | N | N | — | — |
| Unassigned | DPPIII | 737 | N | N | N | — | — |
| Clan SC, | DPPIV | 766 | 100 | Y | Y | 2q24.3 | 7.5–8.0 |
| Family S9, | DPPVI | 865 | 52 | Y | Mutation | 7 | — |
| Subfamily B | FAP | 760 | 70 | Y | Y | 2q23 | 7.5–8.0 |
| | DPRP-1 | 882 | 41 | N | Y | 15q22.1-15q22.2 | 7.5–8.0 |
| | DPRP-2 | 864 | 39 | N | Y | 19p13.3 | 7.5–8.0 |
| | DPRP-3 | 796 | 54 | Y | Mutation | 2q12.3-2q14.1 | — |

The greatest homology between DPRP-1, DPRP-2 and DPPIV is seen in the C-terminal sequences. On the basis of sequence homology with DPPIV (see FIG. 1), one might predict that these DPRP proteins would have functions that include, but are not limited to, roles as enzymes. Cloning, expression, biochemical and molecular characterization have confirmed this hypothesis.

The expression pattern of DPRPs and the localization to specialized epithelial cells and plasma cells (Leydig cells, prostate epithelial cells, lymphocytes, B cells) is consistent with a role in differentiation, proliferation and inflammation. The localization of the DPRP-1 gene in hormone sensitive cancers (breast, prostate, testicular), tissues regulated by testosterone and the abundant expression in poorly differentiated cancers, demonstrate that DPRP-activating or inhibiting molecules will have numerous therapeutic applications in the treatment of disorders characterized by disregulated growth, differentiation and steroid or polypeptide hormone synthesis and degradation. Data disclosed herein supports the hypothesis that DPRP-1 and DPRP-2 are involved in the regulation of proliferation of in vitro models of prostate and testis cancer well known to those skilled in the art.

DPRP-1 and DPRP-2 activities described herein and their expression patterns are compatible with their having functional roles as physiological regulators of the immune and neuroendocrine systems through the enzymatic modification of biochemical mediators like peptides and chemokines. The numerous functions previously described or DPPIV based upon the use of inhibitors may be due in part to its action and that of similar proteins, like the DPRPs. Therefore, the discovery of selective and potent inhibitors of DPPIV, of the DPRPs and of other related proteases like FAP is considered central to achieving effective and safe pharmaceutical use of these and any newly identified serine protease inhibitors, as well as other active compounds that modify the function(s) of such proteins.

The invention thus provides novel proteins or polypeptides, the nucleic acids coding therefor, cells which have been modified with the nucleic acid so as to express these proteins, antibodies to these proteins, a screening method for the discovery of new therapeutic agents which are inhibitors of the activity of these proteins (or which are inhibitors of DPPIV and not of the proteins), and therapeutic agents discovered by such screening methods. The novel proteins and the nucleic acids coding therefor can be used to discover new therapeutic agents for the treatment of certain diseases, such as for example, reproductive, inflammatory and metabolic disorders and also in the preparation of antibodies with therapeutic or diagnostic value.

In accordance with one aspect of the present invention, there are provided novel, mature, biologically active proteins, principally of human origin. Such proteins may be isolated in small quantities from suitable animal (including human) tissue or biological fluids by standard techniques; however, larger quantities are more conveniently prepared in cultures of cells genetically modified so as to express the protein.

In accordance with another aspect of the present invention, there are provided isolated nucleic acid molecules encoding polypeptides of the present invention including mRNAs, DNAs, cDNAs, genomic DNAs thereof.

In accordance with a further aspect of the present invention, nucleic acid probes are also provided comprising nucleic acid molecules of sufficient length to specifically hybridize to a nucleic acid sequence of the present invention.

In accordance with a still further aspect of the present invention, processes utilizing recombinant techniques are provided for producing such polypeptides useful for in vitro scientific research, for example, synthesis of DNA and manufacture of DNA vectors. Processes for producing such polypeptides include culturing recombinant prokaryotic and/or eukaryotic host cells that have been transfected with DNA vectors containing a nucleic acid sequence encoding such a polypeptide and/or the mature protein under conditions promoting expression of such protein and subsequent recovery of such protein or a fragment of the expressed product.

In accordance with still another aspect, the invention provides methods for using DPRP polypeptides and polynucleotides, including the treatment of infections, such as bacterial, fungal, protozoan and viral infections, particularly infections caused by HIV-1 or HIV-2, pain, diabetes, precocious puberty, infertility, obesity, anorexia, bulimia, Parkinson's disease, acute heart failure, hypotension, hypertension, urinary retention, osteoporosis, angina pectoris, myocardial infarction, stroke, ulcers, asthma, allergies, benign prostatic hypertrophy, cancers including hormone-sensitive and androgen-independent cancers, migraines, vomiting, psychotic and neurological disorders, including anxiety, schizophrenia, manic depression, depression, dementia, and severe mental retardation, and dyskinesias, hereinafter collectively referred to as "the Diseases".

In accordance with yet another aspect of the present invention, there is provided a process for utilizing such polypeptides, or polynucleotides encoding such polypeptides, for the discovery of compounds that inhibit the biological activity of the mature proteins thereof, e.g. by cleaving an N-terminal dipeptide, and such inhibitors are thus also provided.

These and other aspects of the present invention should be apparent to those skilled in the art from the detailed description which follows.

BRIEF DESCRIPTION OF THE DRAWINGS

FIGS. 1A and 1B show the co-linear alignment of DPRP-1, DPRP-2, DPRP-3 and DPPIV, with shading being supplied to indicate the same (black) or similar (gray) amino acid residues at a particular location.

FIG. 2 is similar to FIG. 1 and shows co-linear alignment of human and mouse DPRP-2.

DETAILED DESCRIPTION OF THE PREFERRED EMBODIMENTS

Figure 3:
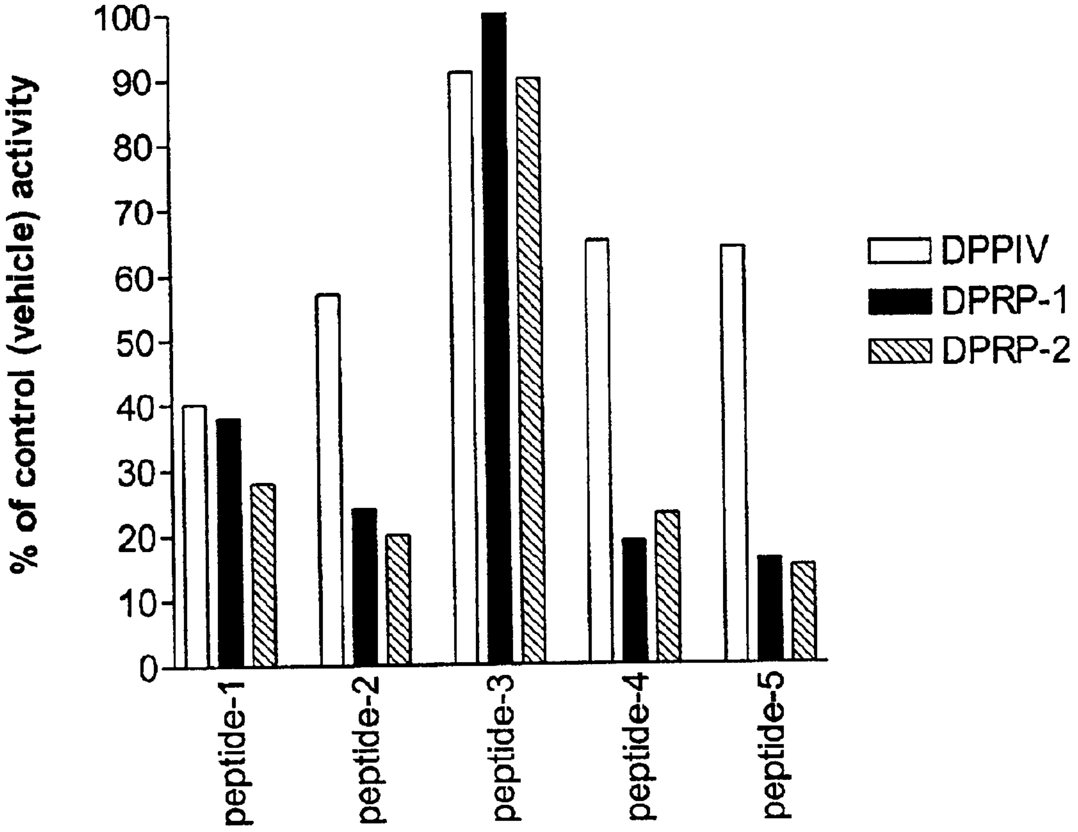
FIG. 3 is a graph which shows the effects of various tetrapeptide amide inhibitors on dipeptidyl peptidase enzyme activity.

In accordance with an aspect of the present invention, there are provided isolated nucleic acid sequences (polynucleotides), which encode the mature polypeptides having the deduced amino acid sequences of the three DPRP's (SEQ ID NOS:1, 3 and 5).

The polynucleotides of this invention were discovered using a human testis cDNA library (DPRP-1), a human colon library (DPRP-2) and a human hypothalamus cDNA library (DPRP-3). Isolated nucleic acid for DPRP-1 contains an open reading frame encoding a protein of approximately 882 amino acids in length which is structurally related to human DPPIV, showing 26% identity, and 41% similarity over the entire human DPPIV protein sequence. Isolated nucleic acid for DPRP-2 contains an open reading frame encoding for a protein of approximately 864 amino acids, which is 39% similar to the entire DPPIV amino acid sequence. Analysis of DPRP-1 and DPRP-2 primary amino acid sequence using hydrophobicity plots predicts that these two proteins do not have a transmembrane domain. Despite this fact, it is possible that these intracellular serine proteases are secreted upon cellular activation. Quiescent cell proline dipeptidase (QPP) is a serine protease that is targeted to intracellular vesicles that are distinct from lysosomes (Chiravuri M, et al., J. Immunol. Nov. 15, 2000;165(10):5695-702). This hypothesis expands the potential site(s) and scope of DPRP-1 and DPRP-2 involvement in mechanisms for post-translational regulation of chemokines, cytokines, peptides and polypeptides. The full length DPRP-3 sequence contains 796 amino acids, a signal peptide from 1 to 48, and a transmembrane domain between 34 and 56. The mature protein is predicted to be a type II membrane protein and may be cleaved to produce a soluble form. The amino acid sequence is set forth in SEQ ID NO:5, which was deduced from SEQ ID NO: 6 and has 54% similarity with DPPIV.

Amino acid sequence alignments of these polypeptides with members of the prolyloligopeptidase enzyme subfamily S9B show that all three DPRP proteins have overall sequence and structural homology to DPPIV and FAP. DPRPs are predicted to be a members of the enzyme Clan SC (Serine nucleophile) with catalytic residues in the order Ser, Asp, His and the active site sequence (G-W-S-Y-G).

TABLE 2

Homology (i.e. similarity) between DPRP-1, DPRP-2, DPRP-3 and members of the prolyl oligopeptidase family S9B enzymes.

| DPPIV | DPRP-1 | DPRP-2 | DPRP-3 | FAP | DPPVI |
|---|---|---|---|---|---|
| 41 | | | | | |
| 39 | 74 | | | | |
| 54 | 39 | 40 | | | |
| 70 | 41 | 39 | 52 | | |
| 52 | 40 | 42 | 68 | 54 | |

DPRP-1, DPRP-2 and DPRP-3 do not exhibit sequence similarity with any members of the classical serine protease families, chymotrypsin and subtilisin. The order of the catalytic triad residues is different in the three main related SC clan families: His-Asp-Ser in chymotrypsin, Asp-His-Ser in subtilisin and Ser-Asp-His in the prolyl oligopeptidases.

As shown in Table 2, DPRP-3 has the highest homology with DPPVI (68% homology and 51% identity). Wada et al isolated cDNA clones for DPPVI, a DPPIV-elated protein, from bovine, rat (Wada et al., *Proc. Nat. Acad. Sci.* 89: 197–201. (1992)) and human (Yokotani et al., *Hum. Molec. Genet.* 2:1037–1039 (1993)) brain libraries. They demonstrated that, unlike DPPIV, the catalytic triad in DPPVI does not have the first serine residue. In DPRP-3 two of the amino acids in the catalytic triad characteristic of the serine protease family are conserved. However, the serine residue itself is replaced by glycine. While the absence of the serine residue is likely to prevent protease activity at this site, it is possible that multiple other functions mediated by other functional domains of the protein remain intact.

As briefly described above, DPPIV is a multifunctional molecule that exerts important functions depending on the expressed cells and tissues, in addition to its catalytic activity as a peptidase. DPRP-3 and DPPVI are also likely to maintain multiple functions despite the absence of an intact catalytic triad. For example, DPPVI has been implicated in the regulation of neuronal plasticity. DPPVI is highly expressed in the hippocampus, thalamus, hypothalamus and stiatum. In addition, developmental arrest and embryonic lethality of rump white Rw/Rw embryos is thought to be due to disruption of the DPPIV gene. Rw mutation is associated with a chromosomal inversion spanning 30 cM of the proximal portion of mouse chromosome 5. Genomic analysis of the DPPVI gene on the Rw chromosome places the inversion breakpoint in the coding region resulting in loss of a significant fraction of the C-terminal region, Hough R. B. et al., *Proc. Nat. Acad. Sci.*, 95, 13800–13805 (1998).

The human DPRP-1 gene, predicted to be 32668 bp in length, has at least 22 exons and eight transcripts. It maps to chromosome 15 (NT_010265) at position 15q21.1-15q22.1. The lengths of predicted alternative splice variant transcripts vary between 602 bp and 4523 bp (see SEQ ID NOS: 7–22). This is in agreement with the multiple transcripts observed by Northern blot analysis (See Example 2). ESTs representing the transcripts were found in numerous tissues including senescent fibroblasts, T-lymphocytes, germinal center B-cells, germ cell seminoma, testis, melanocytes, uterus, ovary breast, multiple sclerosis lesions, pancreas and placenta.

Human DPRP-2 belongs to a gene with at least 27 exons and nine splice variants (see SEQ ID NOS:23–40). One SNP was observed in the 3' UTR. (88% (37) C vs. 12% (5) T). The DPRP-2 gene maps to region 19p13.3 of chromosome 19. This location is host to a number of disease markers and is associated with various disorders including hypocalciuric hypercalcemia, type II cerebellar ataxia, muscular dystrophy, convulsions, susceptibility to atherosclerosis, psoriasis, ectodermal dysplasia, and acute myeloid leukemia. In agreement with the ubiquitous distribution of the mRNA observed by Northern blot analysis (see Example 2), DPRP-2 was expressed in a wide variety of tissues upon examination of EST's coverage (e.g. over 64 EST's expressed in liver, spleen, muscle, melanocytes, heart, lung, placenta, skin, pancreas, stomach, brain parathyroid gland).

Human DPRP-3 belongs to a gene with at least 23 exons and two splice variants (see SEQ ID NOS:41–44). The gene maps to chromosome 2 (NT_005445) at position 2q12.3-2q14.1. Transcripts for DPRP-3 did not show as wide a distribution as DPRP-1 and DPRP-2. As shown by Northern blot in Example 2, DPRP-3 expression is restricted to brain and pancreas. ESTs representing the DPRP-3 mRNA were abundant in tissue derived from multiple sclerosis lesions, hypothalamus, whole brain and nerves, with a few transcripts being found in uterus and colon.

The relationships among human and rodent proteases in clan SC, including DPRP-1 DPRP-2 and DPRP-3, were analyzed using Neighbor Joining method (NJ), see Saitou and Nei, *Mol. Biol. Evol.*, 4, 406–525 (1987). Phylogenetic analysis shows that among the S9 proteases, DPRP-1 and DPRP-2, both lacking a transmembrane domain, are distinguished from DPPIV and its closely related proteins like FAP. Similarity is shown however between DPPIV and FAP and between DPRP-3 and DPPVI, which are all type II membrane proteins.

A database search for additional DPRP-related genes revealed the presence of a murine sequence related to DPRP-1. Alignment of this mouse sequence with the novel human proteases shows that the mDPRP-1 displays considerable homology with its human counterpart (FIG. 2). One skilled in the art will readily recognize that the novel mouse protease gene can be isolated using the sequence information disclosed herein and can be readily incorporated into one of the routinely used expression constructs which are well known in the art. Use of this disclosed sequence by those skilled in the art to generate a transgenic mouse model will employ development of gene-targeting vectors, for example, that result in homologous recombination in mouse embryonic stem cells. The use of knockout mice in further analysis of the function of DPRP genes is a valuable tool.

The polynucleotides of the present invention may be in the form of RNA or in he form of DNA; DNA should be understood to include cDNA, genomic DNA, and synthetic DNA. The DNA may be double-stranded or single-stranded and, if single-stranded, may be the coding strand or non-coding (antisense) strand. The coding sequence which encodes the mature polypeptide may be identical to the coding sequence shown in SEQ ID NOS:2, 4 and 6 respectively, or it may be a different coding sequence encoding the same mature polypeptide, as a result of the redundancy or degeneracy of the genetic code or a single nucleotide polymorphism. For example, it may also be an RNA transcript which includes the entire length of any one of SEQ ID NOS:2, 4 and 6.

The polynucleotides which encode the mature proteins of SEQ ID NOS:1, 3, 5, respectively, may include but are not limited to the coding sequence for the mature protein alone; the coding sequence for the mature polypeptide plus additional coding sequence, such as a leader or secretory sequence or a proprotein sequence; and the coding sequence for the mature protein (and optionally additional coding sequence) plus non-coding sequence, such as introns or a non-coding sequence 5' and/or 3' of the coding sequence for the mature protein.

Thus, the term "polynucleotide encoding a polypeptide" or the term "nucleic acid encoding a polypeptide" should be understood to encompass a polynucleotide or nucleic acid which includes only coding sequence for the mature protein as well as one which includes additional coding and/or non-coding sequence. The terms polynucleotides and nucleic acid are used interchangeably.

The present invention also includes polynucleotides where the coding sequence for the mature protein may be fused in the same reading frame to a polynucleotide sequence which aids in expression and secretion of a polypeptide from a host cell; for example, a leader sequence which functions as a secretory sequence for controlling transport of a polypeptide from the cell may be so fused. The polypeptide having such a leader sequence is termed a preprotein or a preproprotein and may have the leader sequence cleaved, by the host cell to form the mature form of the protein. These polynucleotides may have a 5' extended region so that it encodes a proprotein, which is the mature protein plus additional amino acid residues at the N-terminus. The expression product having such a prosequence is termed a proprotein, which is an inactive form of the mature protein; however, once the prosequence is cleaved an active mature protein remains. Thus, for example, the polynucleotides of the present invention may encode mature proteins, or proteins having a prosequence, or proteins having both a prosequence and a presequence (leader sequence).

The polynucleotides of the present invention may also have the coding sequence used in frame to a marker sequence which allows for purification of the polypeptides of he present invention. The marker sequence may be a polyhistidine tag, a hemagglutinin (HA) tag, a c-myc tag or a V5 tag when a mammalian host, e.g. COS-1 cells, is used. The HA tag would correspond to an epitope derived from the influenza hemagglutinin protein (Wilson, I., et al., *Cell*, 37:767 (1984)), and the c-myc tag may be an eptitope from human Myc protein (Evans, G. I. et al., *Mol. Cell. Biol.* 5: 3610–3616 (1985)).

The term "gene" means the segment of DNA involved in producing a polypeptide chain; it includes regions preceding and following the coding region (leader and trailer) as well as intervening sequences (introns) between individual coding segments (exons). The term "significant sequence homology" is intended to denote that at least 25%, preferably at least 40%, of the amino acid residues are conserved, and that, of the non-conserved residues, at least 40% are conservative substitutions.

Fragments of the full-length genes of the present invention may be used as a hybridization probe for a cDNA library to isolate full-length cDNA as well as to isolate other cDNAs which have significant sequence homology to the gene and will encode proteins or polypeptides having similar biological activity or function. By similar biological activity or function, for purposes of this application, is meant the ability to cleave an N-terminal dipeptide having Ala or Pro as the penultimate residue or other amino acids. Such a probe of this type has at least 14 bases (at least 14 contiguous nucleotides from one of SEQ ID NOS:2, 4 or 6), preferably at least 30 bases, and such may contain, for example, 50 or more bases. Such probe may also be used to identify a cDNA clone corresponding to a full-length transcript and/or a genomic clone or clones that contains the complete gene, including regulatory and promoter regions, exons, and introns. Labelled oligonucleotides having a sequence complementary to that of the gene of the present invention are useful to screen a library of human cDNA, genomic DNA or mRNA to locate members of the library to which the probe hybridizes. As an example, a known DNA sequence may be used to synthesize an oligonucleotide probe which is then used in screening a library to isolate the coding region of a gene of interest.

The present invention is considered to further provide polynucleotides which hybridize to the hereinabove-described sequences wherein there is at least 70%, preferably at least 90%, and more preferably at least 95% identity or similarity between the sequences, and thus encode proteins having similar biological activity. Moreover, as known in the art, there is "similarity" between two polypeptides when the amino acid sequences contain the same or conserved amino acid substitutes for each individual residue in the sequence. Identity and similarity may be measured using sequence analysis software (e.g., Sequence Analysis Software Package of the Genetics Computer Group, University of Wisconsin Biotechnology Center, 1710 University Avenue, Madison, Wis. 53705). The present invention particularly provides such polynucleotides which hybridize under stringent conditions to the hereinabove-described polynucleotides. As herein used, the term "stringent conditions" means conditions which permit hybridization between polynucleotides sequences and the polynucleotide sequences of SEQ ID NOS:2, 4 and 6 where there is at least about 70% identity. Suitably stringent conditions can be defined by, e.g., the concentrations of salt or formamide in the prehybridization and hybridization solutions, or by the hybridization temperature, and are well known in the art. In particular, stringency can be increased by reducing the concentration of salt, by increasing the concentration of formamide, and/or by raising the hybridization temperature.

For example, hybridization under high stringency conditions may employ about 50% formamide at about 37° C. to 42° C., whereas hybridization under reduced stringency conditions might employ about 35% to 25% formamide at about 30° C. to 35° C. One particular set of conditions for hybridization under high stringency conditions employs 42° C., 50% formamide, 5×. SSPE, 0.3% SDS, and 200 $\mu$g/ml sheared and denatured salmon sperm DNA. For hybridization under reduced stringency, similar conditions as described above may be used in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art. Preferably, hybridization should occur only if there is at least 95%, and more preferably at least 97%, identity between the sequences. The polynucleotides which hybridize to the hereinabove described polynucleotides in a preferred embodiment encode polypeptides which exhibit substantially the same biological function or activity as the mature protein encoded by one of the cDNAs of SEQ ID NOS:2, 4 and 6.

As mentioned, a suitable polynucleotide probe may have at least 14 bases, preferably 30 bases, and more preferably at least 50 bases, and will hybridize to a polynucleotide of the present invention which has an identity thereto, as hereinabove described, and which may or may not retain activity. For example, such polynucleotides may be employed as a probe for hybridizing to the polynucleotides of SEQ ID NOS:2, 4 and 6 respectively, for example, for recovery of such a polynucleotide, or as a diagnostic probe, or as a PCR primer. Thus, the present invention includes polynucleotides having at least a 70% identity, preferably at least a 90% identity, and more preferably at least a 95% identity to a polynucleotide which encodes the polypeptides of SEQ ID NOS:1, 3 and 5 respectively, as well as fragments thereof, which fragments preferably have at least 30 bases and more preferably at least 50 bases, and to polypeptides encoded by such polynucleotides.

As is well known in the art, the genetic code is redundant in that certain amino acids are coded for by more than one nucleotide triplet (codon), and the invention includes those polynucleotide sequences which encode the same amino acids using a different codon from that specifically exemplified in the sequences herein. Such a polynucleotide sequence is referred to herein as an "equivalent" polynucleotide sequence. The present invention further includes variants of the hereinabove described polynucleotides which encode for fragments, such as part or all of the mature protein, analogs and derivatives of one of the polypeptides having the deduced amino acid sequence of SEQ ID NOS:1, 3 and 5 respectively. The variant forms of the polynucleotides may be a naturally occurring allelic variant of the polynucleotides or a non-naturally occurring variant of the polynucleotides. For example, the variant in the nucleic acid may simply be a difference in codon sequence for the amino acid resulting from the degeneracy of the genetic code, or there may be deletion variants, substitution variants and addition or insertion variants. As known in the art, an allelic variant is an alternative form of a polynucleotide sequence which may have a substitution, deletion or addition of one or more nucleotides that does not substantially alter the biological function of the encoded polypeptide.

The present invention further includes polypeptides which have the deduced amino acid sequence of SEQ ID NOS:1, 3 and 5, as well as fragments, analogs and derivatives of such polypeptides. The terms "fragment," "derivative" and "analog", when referring to the polypeptides of SEQ ID NOS:1, 3 and 5, means polypeptides that retain essentially the same biological function or activity as such polypeptides. An analog might, for example, include a proprotein which can be activated by cleavage of the proprotein portion to produce an active mature protein. The polypeptides of the present invention may be recombinant polypeptides, natural polypeptides or synthetic polypeptide; however, they are preferably recombinant polypeptides, glycosylated or unglycosylated.

The fragment, derivative or analog of a polypeptide of SEQ ID NOS:1, 3 and 5 respectively, may be (i) one in which one or more of the amino acid residues is substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the mature protein, such as a leader or secretory sequence or a sequence which is employed for purification of the mature polypeptide or a proprotein sequence. Such fragments, derivatives and analogs are deemed to be within the scope of those skilled in the art to provide upon the basis of the teachings herein.

The polypeptides and polynucleotides of the present invention should be in an isolated form, and preferably they are purified to substantial homogeneity or purity. By substantial homogeneity is meant a purity of at least about 85%.

The term "isolated" is used to mean that the material has been removed from its original environment (e.g., the natural environment if it is naturally occurring). For example, a naturally occurring polynucleotide or polypeptide present in a living animal is not considered to be isolated, but the same polynucleotide or polypeptide, when separated from substantially all of the coexisting materials in the natural system, is considered isolated. For DNA, the term includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Further included is recombinant DNA which includes a portion of the nucleotides shown in one of SEQ ID NO:2, 4 or 6 which encodes an alternative splice variant of the DPRP. Various alternative splice variants are exemplified in SEQ ID NOS:8, 10, 12, 14, 16, 18, 20, 22, 24, 26, 28, 30, 32, 34, 36, 38, 40, 42, 44 and 46.

The polypeptides of the present invention include any one of the polypeptide of SEQ ID NOS:1, 3 and 5 (in particular the mature protein), as well as polypeptides which have at least 70% similarity (e.g. preferably at least 60% and more preferably at least 70% identity) to one of the polypeptides of SEQ ID NOS: 1, 3 and 5, more preferably at least 90% similarity (e.g. preferably at least 90% identity) to one of the polypeptides of SEQ ID NOS:1, 3 and 5, and most preferably at least 95% similarity (e.g. preferably at least 95% identity) to one of the polypeptides of SEQ ID NOS:1, 3 and 5. Moreover, they should preferably include exact portions of such polypeptides containing a sequence of at least 30 amino acids, and more preferably at least 50 amino acids.

Fragments or portions of the polypeptides of the present invention may be employed as intermediates for producing the corresponding full-length polypeptides by peptide synthesis. Fragments or portions of the polynucleotides of the present invention may also be used to synthesize full-length polynucleotides of the present invention.

The present invention also includes vectors which include such polynucleotides, host cells which are genetically engineered with such vectors and the production of polypeptides by recombinant techniques using the foregoing. Host cells are genetically engineered (transduced or transformed or transfected) with such vectors which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those commonly used with the host cell selected for expression, as well known to the ordinarily skilled artisan.

The polynucleotides of the present invention may be employed for producing polypeptides by recombinant techniques. Thus, for example, the polynucleotides may be included in any one of a variety of expression vectors for expressing polypeptides. Such vectors include chromosomal, nonchromosomal and synthetic DNA sequences, e.g., derivatives of SV40; bacterial plasmids;

phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by any of a variety of procedures. In general, the DNA sequence is inserted into an appropriate restriction endonuclease site(s) by procedures well known in the art, which procedures are deemed to be within the scope of those skilled in this art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda P.sub.L promoter and other promoters known to control expression of genes in prokaryotic or eukaryotic cells or their viruses. The expression vector should also contain a ribosome binding site for translation initiation and a transcription terminator. The vector may also include appropriate sequences for amplifying expression. In addition, the expression vectors preferably contain one or more selectable marker genes to provide a phenotypic trait for selection of transformed host cells, such as dihydrofolate reductase or neomycin-resistance for eukaryotic cell culture, or such as tetracycline- or ampicillin-resistance in *E. coli.*

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or Bowes melanoma; adenoviruses; plant cells, etc. The selection of an appropriate host is deemed to be within the scope of those skilled in the art from the teachings herein.

Synthetic production of nucleic acid sequences is well known in the art as is apparent from CLONTECH 95/96 Catalogue, pages 215–216, CLONTECH, 1020 East Meadow Circle, Palo Alto, Calif. 94303. Thus, the present invention also includes expression vectors useful for the production of the proteins of the present invention The present invention further includes recombinant constructs comprising one or more of the sequences as broadly described above. The constructs may comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example: Bacterial: pQE70, pQE60, pQE-9 (Qiagen), pBS, pD10, phagescript, psiX174, pbluescript SK, pbsks, pNH8A, pNH16a, pNH18A, pNH46A (Stratagene), ptrc99a, pKK223-3, pKK233-3, pDR540 and pRIT5 (Pharmacia); and Eukaryotic: pWLNEO, pSV2CAT, pOG44, pXT1, pSG (Stratagene) pSVK3, pBPV, pMSG, and pSVL (Pharmacia). However, any other suitable plasmid or vector may be used as long as it is replicable and viable in the host.

Promoter regions can be selected from any desired gene using CAT (chloramphenicol acetyl transferase) vectors or other vectors with selectable markers. Two appropriate vectors are pKK232-8 and pCM7. Particular named bacterial promoters include lacI, lacZ, T3, T7, gpt, lambda P.sub.R, P.sub.L and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Components of the expression vector may generally include: 1) a neomycin phosphotransferase (G418), or hygromycin B phosphotransferase (hyg) gene as a selection marker, 2) an *E. coli* origin of replication, 3) a T7 and SP6 phage promoter sequence, 4) lac operator sequences, 5) the lactose operon repressor gene (lacIq) and 6) a multiple cloning site linker region. Such an origin of replication (oriC) may be derived from pUC19 (LTI, Gaithersburg, Md.).

A nucleotide sequence encoding one of the polypeptides SEQ ID NOS:2, 4 and 6 having the appropriate restriction sites is generated, for example, according to the PCR protocol described in Example 1 hereinafter, using PCR primers having restriction sites for KpnI (as the 5' primer) and NotI or SacI (as the 3' primer) for DPRP-1, or sites for HindIII (as the 5' primer) and NotI or BamHI (as the 3' primer) for DPRP-2. The PCR inserts are gel-purified and digested with compatible restriction enzymes. The insert and vector are ligated according to standard protocols.

In a further embodiment, the present invention provides host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, lipofection or electroporation (Davis, L., Dibner, M., Battey, I., Basic Methods in Molecular Biology, (1986)).

Such constructs in host cells are preferably used in a conventional manner to produce the gene product encoded by the recombinant sequence. Alternatively, the polypeptides of the invention can be synthetically produced by conventional peptide synthesizers or by chemical ligation of suitable fragments thus prepared.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers include cis-acting elements of DNA, usually about from 10 to 300 bp, that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin-resistance gene of *E. coli* and *S. cerevisiae* TRP1 gene, and a promoter derived from a highly expressed gene to direct transcription of a downstream structural sequence. Such promoters can be derived from operons encoding glycolytic enzymes, such as 3-phosphoglycerate kinase (PGK), alpha-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desired, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction), and cells are cultured for an additional period. Cells are typically harvested by centrifugation and then disrupted by physical or chemical means, with the resulting crude extract being retained for further purification. Microbial cells employed in expression of proteins can be disrupted by any convenient method, including freeze-thaw cycling, sonication, mechanical disruption and use of cell-lysing agents; such methods are well known to those skilled in the art.

Various mammalian cell culture systems can also be employed to express a recombinant protein. Examples of mammalian expression systems include the COS-7 lines of monkey kidney fibroblasts, described by Gluzman, *Cell* 23:175 (1981). Other cell lines capable of expressing a compatible vector include, for example, the C127, 3T3, CHO, HeLa and BHK cell lines. Mammalian expression vectors will generally comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Recovery can be facilitated if the polypeptide is expressed at the surface of the cells, but such is not a prerequisite. Recovery may also be desirable of cleavage products that are cleaved following expression of a longer form of the polypeptide. Protein refolding steps as known in this art can be used, as necessary, to complete configuration of the mature protein. High performance liquid chromatography (HPLC) can be employed for final purification steps.

The polypeptides of the present invention may be purified natural products, or produced by recombinant techniques from a prokaryotic or eukaryotic host (for example, by bacterial, yeast, higher plant, insect or mammalian cells in culture). Depending upon the host employed in a recombinant production procedure, the polypeptides of the present invention may be glycosylated or may be non-glycosylated. Polypeptides of the invention may also include an initial methionine amino acid residue.

In a preferred embodiment, the proteins of the invention are isolated and purified so as to be substantially free of contamination from other proteins. For example, the proteins of the invention should constitute at least 80% by weight of the total protein present in a sample, more preferably at least 90%, even more preferably at least 95%, and most preferably at least 98% by weight of the total protein.

These proteins may be in the form of a solution in water, another suitable solvent, such as dimethyl sulphoxide (DMSO) or ethanol, or a mixture of suitable solvents. Examples of mixtures of solvents include 10% (by weight) ethanol in water and 2% (by weight) DMSO in water. A solution may further comprise salts, buffering agents, chaotropic agents, detergents, preservatives and the like. Alternatively, the proteins may be in the form of a solid, such as a lyophilised powder or a crystalline solid, which may also comprise a residual solvent, a salt or the like.

As used herein, the term "antibodies" includes polyclonal antibodies, affinity-purified polyclonal antibodies, monoclonal antibodies, and antigen-binding fragments, such as $F(ab')_2$ and Fab' proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans should be reduced.

Alternative techniques for generating or selecting antibodies useful herein include in vitro exposure of lymphocytes to human prohormone DPRP protein or a peptide therefrom, and selection of antibody display libraries in phage or similar vectors (for instance, through use of immobilized or labeled human DPRP protein or peptide). Genes encoding polypeptides having potential human DPRP polypeptide binding domains can be obtained by screening random peptide libraries displayed on phage (phage display) or on bacteria, such as *E. coli*. Nucleotide sequences encoding such polypeptides can be obtained in a number of ways well known in this art.

As would be evident to one of ordinary skill in the art, polyclonal antibodies can be generated from inoculating a variety of warm-blooded animals, such as horses, cows, goats, sheep, dogs, chickens, rabbits, mice and rats, with a human DPRP polypeptide or a fragment thereof. The immunogenicity of a human prohormone DPRP polypeptide may be increased through the use of an adjuvant, such as alum (aluminum hydroxide) or Freund's complete or incomplete adjuvant, or surface active substances, such as lysolecithin, pluronic polyols, polyanions, peptides, oil emulsions, KLH or dinitrophenol. Among adjuvants used in humans, BCG (bacilli Calmette-Guerin) and Corynebacterium parvum are especially preferable. Polypeptides useful for immunization also include fusion polypeptides, such as fusions of DPRP or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier, such as keyhole limpet hemocyanin (KLH), bovine serum albumin (BSA) or tetanus toxoid, for immunization. Antibodies to DPRP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which block or modify interactions at the active sites) are especially preferred for therapeutic use.

For the production of antibodies, binding proteins, or peptides which bind specifically to DPRP, libraries of single chain antibodies, Fab fragments, other antibody fragments, non-antibody protein domains, or peptides may be screened. The libraries could be generated using phage display, other recombinant DNA methods, or peptide synthesis (Vaughan, T. J. et al. *Nature Biotechnology* 14: 309–314 (1966)). Such libraries would commonly be screened using methods which are well known in the art to identify sequences which demonstrate specific binding to DPRP.

It is preferred that the oligopeptides, peptides, or fragments used to induce antibodies to DPRP have an amino acid sequence consisting of at least about 5 amino acids and, more preferably, of at least about 10 amino acids. It is also preferable that these oligopeptides, peptides, or fragments are identical to a portion of the amino acid sequence of the natural protein. Short stretches of DPRP amino acids may also be fused with those of another protein, such as KLH, and antibodies to the chimeric molecule may be produced.

Monoclonal antibodies to DPRP may be prepared using any well known technique which provides for the production of antibody molecules by continuous cell lines in culture. These include, but are not limited to, the hybridoma technique, the human B-cell hybridoma technique, and the EBV-hybridoma technique, although monoclonal antibodies produced by hybridoma cells may be preferred.

In addition, techniques developed for the production of "chimeric antibodies", such as the splicing of mouse antibody genes to human antibody genes to obtain a molecule with appropriate antigen specificity and biological activity, can be used, see Neuberger, M. S. et al. *Nature* 312: 604–608 (1984). Alternatively, techniques described for the production of single chain antibodies may be adapted, using methods known in the art, to produce DPRP-specific single chain antibodies. Antibodies with related specificity, but of distinct idiotypic composition, may be generated by chain shuffling from random combinatorial immunoglobulin libraries. (Burton D. R. *Proc. Natl. Acad. Sci.* 88: 11120–11123 (1991)).

Antibodies may also be produced by inducing in vivo production in the lymphocyte population or by screening immunoglobulin libraries or panels of highly specific binding reagents as disclosed in the literature. (Orlandi, R. et al. *Proc. Natl. Acad. Sci.* 86: 3833–3837 (1989)).

Antibody fragments which contain specific binding sites for DPRP may also be generated. For example, such fragments include, but are not limited to, $F(ab')_2$ fragments produced by pepsin digestion of the antibody molecule and Fab fragments generated by reducing the disulfide bridges of the $F(ab')_2$ fragments. Alternatively, Fab expression libraries may be constructed to allow rapid and easy identification of monoclonal Fab fragments with the desired specificity. (Huse, W. D. et al. *Science* 254: 1275–1281 (1989)).

Various immunoassays may be used to identify antibodies having the desired specificity. Numerous protocols for competitive binding or immunoradiometric assays using either polyclonal or monoclonal antibodies with established specificities are well known in the art. Such immunoassays typically involve the measurement of complex formation between DPRP and its specific antibody. A two-site, monoclonal-based immunoassay utilizing monoclonal antibodies reactive to two non-interfering DPRP epitopes is preferred, but a competitive binding assay may also be employed.

As earlier mentioned, the DPRPs can be used in treatment of the Diseases. Pharmaceutical compositions suitable for use in this aspect of the invention include compositions wherein the active ingredients are contained in an effective amount to achieve the intended purpose relating to one of the Diseases. The determination of a therapeutically effective dose is well within the capability of those skilled in the art and can be estimated initially either in cell culture assays, e.g. of neoplastic cells, or in animal models, usually mice, rats, rabbits, dogs, or pigs. An animal model may also be used to determine the appropriate concentration range and route of administration, which information is then commonly used to determine useful doses and routes for administration in humans.

A therapeutically effective dose refers to that amount of active ingredient, e.g. a DPRP or fragment thereof, antibodies of DPRP, or an agonist, antagonist or inhibitor of DPRP, which ameliorates particular symptoms or conditions of the Disease. For example, the amount to be administered may be effective to cleave a desired target substrate upon contact therewith. Therapeutic efficacy and toxicity may likewise be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

An exact dosage will normally be determined by the medical practitioner in light of factors related to the subject requiring treatment, with dosage and administration being adjusted to provide a sufficient level of the active moiety or to maintain a desired effect. Factors to be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or even once every two weeks, depending on the half-life and clearance rate of the particular formulation.

Yet another aspect of the invention provides polynucleotide molecules having sequences that are antisense to mRNA transcripts of DPRP1, DPRP2 and DPRP-3 polynucleotides. Administration of an antisense polynucleotide molecule can block the production of the protein encoded by DPRP-1, DPRP2 or DPRP-3. The techniques for preparing antisense polynucleotide molecules and administering such molecules are known in the art. For example, antisense polynucleotide molecules can be encapsulated into liposomes for fusion with cells.

In particular, the expression of DPRP-1, DPRP-2 and DPRP-3 in specialized epithelial cells, immune cells (lymphocytes and B cells), astrocytic tumors, and in various hormone sensitive cancers provides evidence of a potential role in the pathophysiology of cancer, metaplasia and metastasis. Therefore in a further aspect, the invention relates to diagnostic assays for detecting diseases associated with inappropriate DPRP activity or expression levels. Antibodies that specifically bind DPRP may be used for the diagnosis of disorders characterized by expression of DPRP, or in assays to monitor patients being treated with DPRP or with agonists or antagonists (inhibitors) of DPRP. Antibodies useful for diagnostic purposes may be prepared in the same manner as those described above for therapeutics. Diagnostic assays for DPRP include methods that utilize the antibody and a label to detect DPRP in human body fluids or in extracts of cells or tissues. The antibodies may be used with or without modification, and they may be labeled by covalent or non-covalent joining with a reporter molecule. A wide variety of reporter molecules are known in the art. Recombinant DPRP proteins that have been modified so as to be catalytically inactive can also be used as dominant negative inhibitors. Such modifications include, for example, mutation of the active site.

A variety of protocols for measuring DPRP, including ELISAs, RIAs and FACS, are known in the art and provide a basis for diagnosing altered or abnormal levels of DPRP expression. Normal or standard values for DPRP expression are established by combining body fluids or cell extracts taken from normal mammalian subjects, preferably human, with antibody to DPRP under conditions suitable for complex formation. The method for detecting DPRP in a biological sample would comprise the steps of: a) providing a biological sample; b) combining the biological sample and an anti-DPRP antibody under conditions which are suitable for complex formation to occur between DPRP and the antibody; and c) detecting complex formation between DPRP and the antibody, thereby establishing the presence of DPRP in the biological sample. The amount of complex formation then may be quantified by various methods, preferably by photometric means. Quantities of DPRP expressed in subject, control, and disease samples from biopsied tissues are compared with the standard values. Deviation between standard and subject values establishes the parameters for diagnosing disease.

In another embodiment of the invention, the polynucleotides encoding DPRP are used for diagnostic purposes, which polynucleotides may include oligonucleotide sequences, complementary RNA and DNA molecules, and PNAs. These polynucleotides may be used to detect and quantitate gene expression in biopsied tissues in which expression of DPRP may be correlated with one of the Diseases. The diagnostic assay may be used to distinguish between absence, presence, and excess expression of DPRP and to monitor regulation of DPRP levels during therapeutic intervention. Moreover, pharmacogenomic, single nucleotide polymorphisms (SNP) analysis of the DPRP genes can be used as a method to screen for mutations that indicate predisposition to disease or modified response to drugs.

DPRP polynucleotide and polypeptide sequences, fragments thereof, antibodies of DPRPs, and agonists, antagonists or inhibitors of DPRPs can be used to as discovery tools to identify molecular recognition events and therefore proteins, polypeptides and peptides that interact with DPRP proteins. A specific example is phage display peptide libraries where greater than 108 peptide sequences can be screened in a single round of panning. Such methods as well as others are known within the art and can be utilized to identify compounds that inhibit or enhance DPRP-1, DPRP-2 or DPRP-3 activity. Coupled links represent functional interactions such as complexes or pathways, and proteins that interact with DPRPs can be identified by a yeast two-hybrid system, proteomics (differential 2D gel analysis and mass spectrometry) and genomics (differential gene expression by microarray or serial analysis of gene expression SAGE). Proteins identified as functionally linked to DPRPs and the process of interaction form the basis of methods of screening for inhibitors, agonists and antagonists and modulators of these DPRP-protein interactions.

The term "antagonist," as it is used herein, refers to an inhibitor molecule which, when bound to DPRP, decreases the amount or the duration of the effect of the biological or immunological activity of DPRP, e.g. decreasing the enzymatic activity of the peptidase to cleave the N-terminal dipeptide. Antagonists may include proteins, nucleic acids, carbohydrates, antibodies, or any other molecules which decrease the effect of DPRP; for example, they may include small molecules and organic compounds that bind to and inactivate DPRPs by a competitive or non-competitive type mechanism. Specific examples of DPRP tetrapeptide peptidic enzyme activity inhibitors are described in Example 6 and 7. Inhibitors can be, for example, inhibitors of the DPRP protease activity, or alternatively inhibitors of the binding activity of the DPRP to proteins with which they interact. Specific examples of such inhibitors can include, for example, anti-DPRP antibodies, peptides, protein fragments, or small peptidyl protease inhibitors, or small non-peptide, organic molecule inhibitors which are formulated in a medium that allows introduction into the desired cell type. Alternatively, such inhibitors can be attached to targeting ligands for introduction by cell-mediated endocytosis and other receptor mediated events. Such methods are described further below and can be practiced by those skilled in the art given the DPRP nucleotide and amino acid sequences described herein.

A further use for DPRPs is for the screening of potential antagonists for use as therapeutic agents, for example, for inhibiting binding to DPRP, as well as for screening for agonists. DPRP, its immunogenic fragments, or oligopeptides thereof can be used for screening libraries of compounds which are prospective agonists or antagonists in any of a variety of drug screening techniques. The fragment employed in such screening may be free in solution, affixed to a solid support, borne on a cell surface, or located intracellularly. The formation of binding complexes between DPRP and the agent being tested is then measured. Other assays to discover antagonists that will inhibit DPRP are apparent from the disclosures of U.S. Pat. Nos. 6,011,155, 6,107,317, 6,110,949, 6,124,305 and 6,166,063, which describe inhibitors of DPPIV. Another worthwhile use of these DPRPs is the screening of inhibitors of DPPIV to show that they will not have undesired side effects by also inhibiting one or more of the DPRPs.

A method provided for screening a library of small molecules to identify a molecule which binds DPRP generally comprises: a) providing a library of small molecules; b) combining the library of small molecules with the polypeptide of either SEQ ID NOS:1, 3 or 5, or with a fragment thereof, under conditions which are suitable for complex formation; and c) detecting complex formation, wherein the presence of such a complex identifies a small molecule which binds DPRP.

One method for identifying an antagonist comprises delivering a small molecule which binds DPRP into extracts from cells transformed with a vector expressing DPRP along with a chromogenic substrate (e.g. Ala-Pro-AFC or Ala-Pro-AMC) under conditions where cleavage would normally occur, and then assaying for inhibition of cleavage by the enzyme by monitoring changes in fluorescence, or UV light absorption, by spectrophotometry to identify molecules that inhibit cleavage. A reduced rate of reaction or total amount of fluorescence or UV light absorption, in the presence of the molecule, establishes that the small molecule is an antagonist which reduces DPRP catalytic/enzymatic activity. Once such molecules are identified, they may be administered to reduce or inhibit cleaving by a DPRP.

The term "agonist," as used herein, refers to a molecule which, when bound to DPRP, increases or prolongs the duration of the effect of DPRP. Agonists may include proteins, nucleic acids, carbohydrates, or any other molecules that bind to and modulate the effect of DPRP. Although it is less likely that small molecules will prove to be effective DPRP agonists, a method for identifying such a small molecule, which binds DPRP as an agonist, comprises delivering a chromogenic form of a small molecule that binds DPRP into cells transformed with a vector expressing DPRP and assaying for fluorescence or UV light absorption changes by spectrophotometry. An increased amount of UV absorption or fluorescence would establish that the small molecule is an agonist that increases DPRP activity.

Another technique for drug screening which may be used provides for high throughput screening of compounds having suitable binding affinity to the protein of interest as described in published PCT application WO84/03564. In this method, large numbers of different small test compounds are synthesized on a solid substrate, such as plastic pins or some other surface. The test compounds are reacted with DPRP, or with fragments thereof, and then washed. Bound DPRP is then detected by methods well known in the art. Purified DPRP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding DPRP specifically compete with a test compound for binding DPRP. In this manner, antibodies can be used to detect the presence of any peptide that shares one or more antigenic determinants with DPRP.

As indicated above, by investigating the binding sites, ligands may be designed that, for example, have more interactions with DPRP than do its natural ligands. Such antagonist ligands will bind to DPRP with higher affinity and so function as competitive ligands. Alternatively, synthetic or recombinant proteins homologous or analogous to the ligand binding site of native DPRP may be designed, as may other molecules having high affinity for DPRP. Such molecules should also be capable of displacing DPRP and provide a protective effect.

As indicated above, the knowledge of the structures of DPRP enables synthetic binding site homologues and analogues to be designed. Such molecules will facilitate greatly the use of the binding properties to target potential therapeutic agents, and they may also be used to screen potential therapeutic agents. Furthermore, they may be used as immunogens in the production of monoclonal antibodies, which antibodies may themselves be used in diagnosis and/or therapy as described hereinbefore.

Given the ubiquitous expression of several members of the prolyl oligopeptidase S9B family, cell lines in which targeted gene disruption of DPPIV, DPRP-1, DPRP-2, DPRP-3, FAP and DPPVI to establish the null phenotype will be of great value to assist screening for selective and potent compounds. Accordingly, the invention provides such cell lines engineered with Lox-Neo IRES tk cassette and GFP-IRES-Neo Knock-in/out cassette DNA element for constructing somatic gene targeting vectors.

EXAMPLE 1

Cloning and Expression of DPRP Genes Using the Mammalian Expression System

DNA fragments encoding the full-length polypeptide DPRP-1 were amplified using PCR oligonucleotide primers corresponding to the 5' and 3' sequences of the gene, i.e. SEQ ID NO:45 and NO: 46. In addition, DNA fragments encoding the full length polypeptide DPRP-2 were amplified using PCR oligonucleotide primers corresponding to the 5' and 3' sequences of that gene, i.e. SEQ ID NO:50 and NO:51. Furthermore, DNA fragments encoding the full length polypeptide DPRP-3 were amplified using PCR oligonucleotide primers corresponding to the 5' and 3' sequences of that gene, i.e. SEQ ID NO:55 and NO:56.

The three amplified sequences were respectively isolated from a 0.7% agarose gel using commercially available kit (GFX PCR DNA and Gel Band Purification Kit, Amersham Pharmacia Biotech Inc., Piscataway N.J., USA). The fragments were then ligated into cloning vector, pGEM-7Zf(−) (Promega Corporation, Madison Wis., USA) and sequenced. The corresponding cloning constructs were respectively designated pGEM7-DPRP1, pGEM7-DPRP2 and pGEM7-DPRP3. The DNA sequences encoding the truncated DPRP-1 or DPRP-2 or DPRP-3 were amplified using pGEM7-DPRP1 or pGEM7-DPRP2 or pGEM7-DPRP3 as a template and PCR oligonucleotide primers. SEQ ID NO: 45 and NO: 47 were used for DPRP-1; SEQ ID NO: 50 and NO: 52 were used for DPRP-2; and SEQ ID NO: 57 and NO: 58 for DPRP-3. The amplified sequences were again isolated from a 0.7% agarose gel using the same purification kits and sub-cloned into pGEM-7Zf(−). The resulting constructs were designated pGEM7-DPRP1f, pGEM7-DPRP2f and pGEM7-DPRP3f.

To make the DPRP-1 mammalian expression construct, pGEM7-DPRP1 was digested with the restriction enzymes KpnI and NotI to release the full length DPRP-1 gene. The DNA fragment carrying the DPRP-1 gene was gel band purified using the above kit and then inserted into expression vector pcDNA3 (Invitrogen, Carlsbad Calif., USA) to make the native DPRP-1 expression construct, which was designated pcDNA-DPRP1. pGEM7-DPRP If was digested with the restriction enzymes XbaI and HindIII to release the truncated DPRP-1f gene. The DNA fragment carrying the DPRP-1f gene was gel band purified using the above kit and then inserted into expression vector pcDNA3.1(−)/myc-His A (Invitrogen, Carlsbad Calif., USA) to make the tagged DPRP-1 expression construct pcDNA-MycHis-DPRP1.

To make the DPRP-2 mammalian expression construct, pGEM7-DPRP2 was digested with the restriction enzymes HindIII and BamHI to release the full length DPRP-2 gene. The DNA fragment carrying the DPRP-2 gene was gel band purified using the above kit and then inserted into expression vector pcDNA3 (Invitrogen, Carlsbad Calif., USA) to make the native DPRP-2 expression construct, which was designated pcDNA-DPRP2. pGEM7-DPRP2f was digested with the restriction enzymes EcoRI and BamHI to release the truncated DPRP-2f gene. The DNA fragment carrying the DPRP-2f gene was gel band purified using the above kit and then inserted into expression vector pcDNA3.1(−)/myc-His B (Invitrogen, Carlsbad Calif., USA) to make the tagged DPRP-2 expression construct designated pcDNA-MycHis-DPRP2.

To make the DPRP-3 mammalian expression construct, pGEM7-DPRP3 was digested with the restriction enzymes EcoRI and XhoI to release the full length DPRP-3 gene. The DNA fragment carrying the DPRP-3 gene was gel band purified using the above kit and then inserted into expression vector pcDNA3 (Invitrogen, Carlsbad Calif., USA) to make the native DPRP-3 expression construct designated pcDNA-DPRP3. pGEM7-DPRP3f was digested with the restriction enzymes NheI and ApaI to release the truncated DPRP-3f gene. The DNA fragment carrying the DPRP-3f gene was gel band purified using the above kit and then inserted into expression vector pcDNA3.1(−)/myc-His B (Invitrogen, Carlsbad Calif., USA) to make the tagged DPRP-3 expression construct pcDNA-MycHis-DPRP3.

EXAMPLE 2

Expression Pattern of DPRP Genes in Human Tissues

Quantitative PCR analysis was carried out to examine the levels of expression of the mRNAs for the polypeptides of the present invention in human tissues. RT PCR was also carried out on a number of human cell lines including but not limited to prostate cancer cells (LNCaP, PC3, DU145), the MLTC-1 line (mouse testis), and MDA-MB231 cells (breast cancer). Bands of the expected sizes for DPRP-1, DPRP-2 and DPPIV were all expressed in the various cancer cells lines, with FAP also being expressed at very low levels.

Northern Blot Analysis

Northern blot analysis was performed with 2 $\mu$g poly(A)$^+$ RNA isolated from eight different tissues using DPRP probes. Specifically, a human Multiple Tissue Northern (MTN) blot (Clontech, Palo Alto, Calif.) was probed with a 1 kb N-terminal fragment that had been radioactively labeled by random priming in the presence of a $^{32}$PdCTP (A. P. Feinberg et al., *Anal. Biochem*., 132, 6 (1983)). Hybridization was performed at 68° C. overnight in ExpressHyb™ hybridization solution (Clontech, Palo Alto, Calif.). The blots were first washed at room temperature in 2 times SSC and 0.05% SDS, and then washed at 60° C. (DPRP-1 & DPRP-2) and 50° C. (DPRP-3) in 0.1 times SSC and 0.1% SDS.

Northern analysis showed expression of DPRP-1 in several tissues with the most abundant signal being in testis, prostate, muscle and brain. Testis showed 3 transcripts approximately 7.5, 4.5 and 2.5 kb in length. The shorter mRNA species was very abundant in testis but negligible in the other tissues tested. DPRP-2 was ubiquitously expressed in every tissue with highest levels in liver and muscle and a predominant transcript at Skb. DPRP-3 expression was limited to brain and pancreas. Further analysis was conducted for the three proteases in specific brain regions (cerebellum, cortex, medulla, spinal cord, occipital lobe, frontal lobe temporal lobe and putamen). DPRP-1 was expressed in all regions with low levels present in the spinal cord, while DPRP-2 was expressed in all brain regions tested.

Oligonucleotide primers SEQ ID NO:48 and NO:49 were used for DPRP-1 quantitative PCR, whereas oligonucleotide primers SEQ ID NO:53 and NO:54 were used for DPRP-2 quantitative PCR. Human Multiple Tissue cDNA (MTC™) Panel I and Panel II (Clontech, Palo Alto Calif., USA) were used as normalized cDNA templates. 0.5 ng of each cDNA were used in a 25 $\mu$l PCR reaction, with each primer at a final concentration of 300 nM. The PCR reaction was performed using a SYBR Green PCR Core Reagents Kit (Applied Biosystems, Foster City Calif., USA) and detected with an Applied Biosystems GeneAmp 5700 sequence detection system. Manufacturer's recommended thermal cycling parameter, e.g. 50° C. for 2 min, 95° C. for 10 min followed by 40 cycles of 95° C. for 15 sec and 60° C. for 1 min was used. Data obtained shows relatively high rates of expression for both DPRP-1 and DPRP-2 in the pancreas, ovary and testis, and a particularly high rate for DPRP-2 in the liver.

EXAMPLE 3

Production of DPRP Polyclonal Antibodies and Western Blotting

The amino acid sequence deduced from the cDNA encoding DPRP-1 was analyzed using DNASTAR software (DNASTAR, Inc.) to determine regions of high immunogenicity, and a corresponding oligopeptide was synthesized and used to raise anti-DPRP-1 antibodies. The procedure was repeated for DPRP-2 and DPRP-3. The selection of appropriate peptide sequences and the techniques for antibody production are methods well known to those of skill in the art. Selection of appropriate epitopes, such as those near the C-terminus or in hydrophilic regions, is well known in this art.

Typically, oligopeptides that are about 15 to 20 residues in length, e.g. SEQ ID NO:59 for DPRP-1, SEQ ID NO:60 for DPRP-2 and SEQ ID NO:61 for DPRP-3, were synthesized using an Applied Biosystems Peptide Synthesizer Model 431 A. Fmoc-chemistry was used and the 19- or 15-residue peptides were respectively coupled to keyhole limpet hemocyanin (KLH, Sigma, St. Louis, Mo.) by reaction with N-maleimidobenzoyl-N-hydroxysuccinimide ester (MBS). Rabbits were immunized with the oligopeptide-KLH complex in complete Freund's adjuvant. The resulting antisera were tested for antipeptide activity, e.g., by binding the peptide to plastic, blocking with 1% BSA, reacting with rabbit antisera, washing, and reacting with radioiodinated, goat anti-rabbit IgG.

Western blotting was performed using normal human protein samples (Protein Medley) obtained from Clontech (about 36 μg of total proteins). Proteins were fractionated through 10% SDS-polyacrylamide gels, and transferred to 0.45 mm nitrocellulose membranes. Membranes were blocked in Tris-buffered saline (TBS) with 0.05% Tween 20 and 1% BSA. Anti DPRP-1 or DPRP-2 specific antibodies were used as primary antibodies and were diluted 1:5,000 in Tris-buffered saline with 0.05% Tween 20 (TBST) and the Alkaline Phosphatase (AP) conjugated goat anti-Rabbit IgG (Promega) was diluted 1:5,000 in the same buffer before use. The positive reaction was visualized by incubating the membrane in Western Blue Stabilized Substrate (Promega) for AP until the bands of interest have reached the desired intensity. DPRP-1 and DPRP-2 proteins were detected in brain, muscles, kidney, prostate, testis and ovary tissues. DPRP-1 and DPRP-2 were synthesized as approximately 101 kDa and 100 kDa forms, respectively, which are in good agreement with the molecular masses estimated from their primary structure as shown in Table 3.

TABLE 3

Predicted Molecular Weight, Number of potential N-linked glycosylation sites (Asn residues) and predicted pI values of DPRP-1, DPRP-2 and DPRP-3, based on sequence analysis using the method developed by Hopp and Woods, Proc. Nat. Acad. Sci. 78:3824-3828 (1981).

| | M.W. (Da.) | No. of Asn | pI |
|---|---|---|---|
| DPRP1 | 101422 | 26 | 5.39 |
| DPRP2 | 98263 | 27 | 6.01 |
| DPRP3 | 90914 | 33 | 6.11 |

Several additional bands of similar molecular weight were observed. These are thought to be due to the presence of post-translational glycosylation of the proteins. Table 3 also shows the number of potential N-glycosylation sites for the DPRP proteins. The presence of glycosylated and unglcosylated forms of the proteins was evaluated using tunicamycin, an inhibitor of the oligosaccharide synthesis. It is evident that the smaller forms were unglycosylated forms. The correlation between mRNA (Northern analysis) and protein quantity (Western analysis) for DPRP-1 is shown in Table 4.

1. Blocking Reagent for 15 minutes (Normal Goat Serum)
2. Primary Antibody for 25, 60 min or overnight incubation
3. Secondary Antibody for 25 minutes (Biotinylated Goat-anti-rabbit IgG)
4. Endogenous Peroxidase Blocking for 3×1.5 minutes
5. ABC (avidin-biotin complex)/Horse Radish Peroxidase for 25 minutes
6. DAB Chromogen for 3×5 minutes (Brown reaction product)
7. Light Hematoxylin Counter Stain 1 minute Positive controls were run to assure the detection chemistries and antigen pretreatments were working appropriately. Rabbit IgG was run as a negative control. An avidin-biotin based tissue staining system was used for the detection of the DPRP-1 antibody. Horseradish peroxide was used as a reporter enzyme with DAB as chromogen. After staining, slides were dehydrated through an alcohol series to absolute ethanol followed by xylene rinses. Slides were permanently coverslipped with glass coverslips and permount. Digital images of representative staining, where positive staining was indicated by a dark brown chromogen (DAB-HRP reaction product), were captured using a video camera from Olympus. Hematoxylin counterstain provides a blue nuclear stain to assess cell and tissue morphology.

DPRP-1 rabbit polyclonal antibody labels formalin-fixed, paraffin-embedded human tissues, including normal testis, prostate glands, endometrial glands, tonsils and pancreas. It was also present in endothelial cells of normal ovary, bladder and kidney. Staining was localized in the cytoplasm in epithelial and some stromal cells such as fibroblasts, endothelial cells and lymphocytes. Interestingly in normal testis tested with DPRP-1 antibodies, there was distinctive expression in Leydig cells and multinucleated macrophages found in interstitial tissue, which is the space surrounding the seminiferous tubules. Tonsil B cells were stained with DPRP-1 antibody.

EXAMPLE 5

Mammalian and Insect Cell Expression of DPRP Proteins and Purification

Plasmid DNA of pcDNA-DPRP1, pcDNA-MycHis-DPRP1, pcDNA-DPRP-2 or pcDNA-MycHis-DPRP2 was transfected into PEAK (EdgeBioSystems, Gaithersburg Md., USA) or COS-1 (ATCC CRL-1650) using LipofectAmine (Life Technologies, Gaithersburg Md., USA) method recommended by the manufacturer. Transfected cells were maintained in DMEM with 5% FBS at 37° C. with 5% $CO_2$ for 48 hours. Cells were then collected and used for recombinant protein extraction. Cells were harvested 48 hours after transfection, homogenized and then spun at 18,000×g for 40 min. The supernata were collected as cytosolic fractions. This fraction was loaded on TALON spin column (Clontech), and His-tagged proteins were eluted with 50 mM PBS, 150 mM imidazole, pH 7. Recombinant proteins were then detected by western blotting with anti-myc antibody and visualized using a ProtoBlot II AP

TABLE 4

Correlation of mRNA and protein expression of DPRP-1 in human tissues

| | Heart | Brain | Placenta | Muscles | Kidney | Prostate | Testis | Ovary |
|---|---|---|---|---|---|---|---|---|
| Northern | ++ | +++ | + | +++ | ++ | +++ | ++++ | + |
| Western | − | ++++ | − | + | ++ | + | +++ | +++ |

EXAMPLE 4

Immunohistochemical Localization of DPRP Proteins in Human Tissues

Four-micron sections were prepared from a number of different formalin-fixed, paraffin-embedded human tissues. Tissue sections were deparaffined through 4 immersions in xylenes for 5 minutes, followed by a graded alcohol series to distilled water. Steam heat induced epitope recovery (SHIER) was used with several different SHIER solutions with and without enzyme digestion tissue in two different concentrations (Ladner et al, *Cancer Res.*; 60, p 3493–3503, 2000). The treatments and antibody dilutions employed are outlined below.

system (Promega). Recombinant affinity purified fusions of the DPRP-1 and DPRP-2 were detected by western blot, and DPRP-1 and DPRP-2 were synthesized as 112 kDa and 109 kDa forms as predicted.

Naturally occurring or recombinant DPRP proteins were substantially purified by immunoaffinity chromatography using antibodies specific for DPRP-1, DPRP-2 or DPRP-3. An immunoaffinity column was constructed by covalently coupling DPRP antibodies to an activated chromatographic resin, such as CNBr-activated Sepharose (Pharmacia & Upjohn). After the coupling, the resin was blocked and washed according to the manufacturer's instructions.

Media or cell extracts containing DPRP proteins were passed over the immunoaffinity column, and the column was washed under conditions that allow the preferential absorbance of DPRPs (e.g., high ionic strength buffers in the presence of detergent). The column was eluted under conditions that disrupt antibody/DPRP binding (e.g., a buffer of pH 2–3 or a high concentration of a chaotrope, such as urea or thiocyanate ion), and purified DPRP was collected.

EXAMPLE 6

Enzymatic Activity of DPRP Proteins and Methods of Screening for Inhibitors

The kinetic properties of recombinant DPRP-1 and DPRP-2 were determined in a continuous fluorimetric assay. Buffer, pH and temperature dependence optimization led to the following assay conditions: Enzyme assays were performed in 50 mM PBS, pH7.4 50 $\mu$l (50 $\mu$g/ml) of purified enzymes were mixed with 1 $\mu$l of different concentration of Ala-Pro-AMC (Enzyme Systems). Plates were then incubated at 37° C. for 30 min, and fluorescence was detected using a Wallac 1420 Fluorimeter with λex40355 and λem535. The $K_m$ values of DPRP-1 and DPRP-2 were similar (208 and 161 $\mu$M respectively).

Further biochemical characterization reveals that DPRP-1 and DPRP-2 have similar profiles to DPPIV. The two purified proteases and DPPIV were preincubated with inhibitors at room temperature for 30 min. Substrate, Ala-Pro-AMC (100 $\mu$M), was then added, and the fluorescence intensity was recorded as 60 readings during a 60 min period. The irreversible serine protease inhibitor AEBSF was the only inhibitor tested that showed strong inhibition of all three enzymes (Table 5). This confirms the structural and domain analysis prediction that these proteins belong to the serine protease superfamily.

TABLE 5

Inhibition of DPRP-1 and DPRP-2 by Protease Inhibitors

| Inhibitor | Inhibitor Property | Concentration | Residual activity (% of control) DPRP-1 | DPRP-2 | DPPIV |
|---|---|---|---|---|---|
| AEBSF | serine, irreversible | 5 mM | 29.6 | 23.9 | 21.1 |
| Aprotinin | serine, reversible | 5 $\mu$g/ml | 77.5 | 63.2 | 80.2 |
| Pepstatin | aspartic, reversible | 2 $\mu$g/ml | 97.3 | 95.0 | 93.5 |
| DTT | cysteine | 2 mM | 100.1 | 94.8 | 98.3 |
| B-Mercaptoethonal | cysteine | 100 mM | 93.2 | 84.0 | 98.0 |
| EDTA | metallo, reversible | 2 mM | 91.5 | 86.0 | 93.5 |
| Leupeptin | serine, reversible | 50 $\mu$g/ml | 91.1 | 90.4 | 90.7 |

In addition to Ala-Pro-AMC, additional substrates tested also confirmed that DPRP-1 and DPRP-2 are dipeptidyl peptidases. The data were derived by determining the fluorescence change following a 30-minute incubation of the substrates (125 $\mu$M) with enzymes as a percentage of the fluorescence measured at Ala-Pro-AMC and Gly-Pro-AMC were the only good substrates among those tested.

TABLE 6

DPRP-1 and DPRP-2 are dipeptidyl peptidases.

| Substrate | % Change in Fluorescence at 30 minutes DPRP-1 | DPRP-2 | DPPIV |
|---|---|---|---|
| Ala-Pro-AMC | 239.0 | 127.5 | 379.0 |
| Gly-Pro-AMC | 341.5 | 205.0 | 444.0 |
| Ala-Pro-pNA | 45.5 | 44.0 | 29.5 |
| Pro-pNA | −1 | −2.5 | 0.0 |
| Gly-Arg-pNA | −4.5 | −0.5 | 0.0 |
| Lys-Ala-pNA | 2.5 | 0.5 | 0.5 |
| Ala-Phe-Pro-pNA | −4 | −0.5 | 2.0 |

Additional natural and non-natural amino acid di-, tri- and tetra-peptides were tested in order to find an optimal substrate for testing each of the DPRP proteins that will also show reduced activity when incubated DPPIV.

The enzyme assay method described here is one of a number of methods that can be utilized to screen for peptide and non-peptide inhibitors of the DPRP enzymes. Libraries of tetrapeptide inhibitors were tested to discover inhibitors of enzyme activity. Candidate inhibitors were prepared as 10–20 mM stock solutions in DMSO and stored at −20° C. Dilutions were made in assay buffer. Inhibition was determined by comparing the changes in fluorescence of the inhibited enzyme to the change in fluorescence of the control (vehicle) enzyme. 100-(fl units of sample/fl units of control ×100) gives percent inhibition value. The percent inhibition and the inhibitor concentration at which the enzyme was 50% inhibited ($IC_{50}$) was ascertained by plotting percent inhibition vs. inhibitor concentration on the log scale. As shown in FIG. 3, several tetrapeptides amides inhibited enzyme activity, wherein data are expressed as the % of activity in the presence of vehicle (0.02% DMSO) alone. Compounds were added at 1 mM. Most interesting was the apparent differential activity of some tetrapeptides for DPRP-1 and DPRP-2, compared to DPPIV. While all three enzymes were inhibited by Peptide-1, only DPRP-1 and DPRP-2 were significantly inhibited by Peptide-4 and Peptide-5. This demonstrates that selective inhibition of the purified enzymes is achievable.

The assay described in this example can also be used to screen additional synthetic or naturally occurring compound libraries, including macromolecules, for agents that either inhibit or enhance DPRP activity. The DPRP-1 and DPRP-2 polypeptides to be used in the assay can be obtained by, for example, in vitro translation, recombinant expression (see Example 5) or biochemical procedures. Methods other than those described here can also be used to screen and identify compounds that inhibit DPRP-1, DPRP-2 or DPRP-3, which methods can include, for example, binding assays such as ELISAs and RIAs.

EXAMPLE 7

Figure 4A:
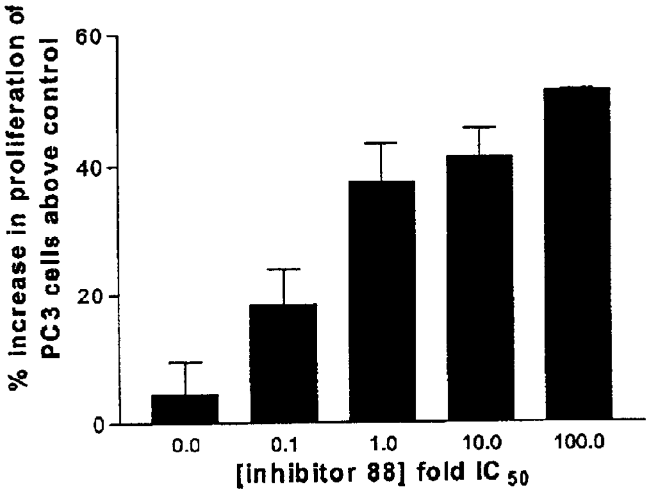
FIGS. 4A–4C show the effects of three inhibitor compounds on the proliferation of PC3 prostate cancer cell lines at various doses.
Figure 4B:
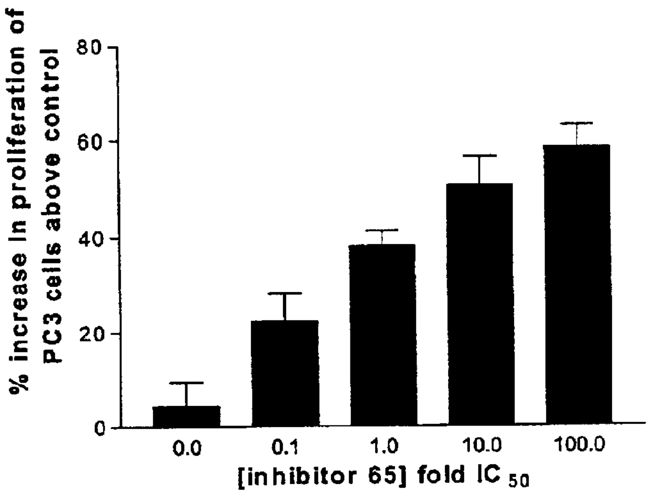
Figure 4C:
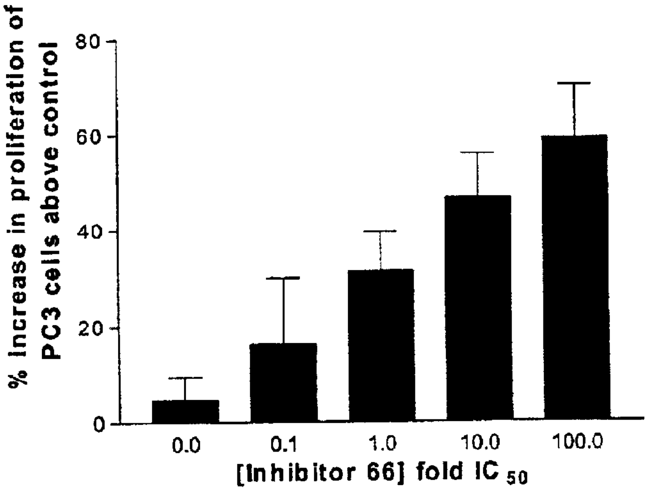

Effect of DPRP Inhibitors on the Proliferation of Human Cancer Cells in Vitro In an attempt to assess the effect that several inhibitors of DPRP-1 and DPRP-2 activity may have on the proliferation of human cancer cells, LNCap, PC3 and Du145, mouse testis line MLTC-1 and MDA-MB231 breast cancer cells were plated ($10^4$ per well) in 96-well tissue culture plates and allowed to grow and attach for 24 hours at 37° C. in a $CO_2$ incubator. Compounds at various dilutions (final dilutions: 0.1 nM–10 $\mu$M) were then added to the wells for various incubation periods from 24 hours to 96 hours, with fresh compound being replaced each day. Addition of the diluent DMSO alone served as the control. Following incubation with these compounds in triplicate, proliferation of the cells was determined using an XTT cell proliferation assay (Roche 1-465-015). The plates were read at 490 and 650 nm 5 hours after the XTT mix was added. An increase in cell proliferation was observed with three of the inhibitors at concentrations equal to 0.1, 1, 10 and $100\times IC_{50}$, and the results are shown in FIGS. 4A, 4B and 4C for PC3 cells.

Overall, the DPRPs are expressed in a wide variety of tissues as has been demonstrated by mRNA amplification, western blotting and immunohistochemistry. DPRP-1 was most abundant in the testis by Northern blot and western blot. The large number of expressed sequence tags (ESTs) from testis cDNA sources that are homologous to DPRP-1 also confirms abundant expression of DPRP-1 in testis. Example 4 describes the immunohistochemical localization of DPRP-1 protein in human testis using a specific DPRP-1 antibody. DPRP-1 is strongly expressed in epitheloid Leydig cells, and Leydig cells are the primary source of testicular androgens (male steroid hormones) in the mammalian male. In the interstitium of the testis, Leydig cells and macrophages are in close association with "digitation" of Leydig cell process extending onto macrophage surface. Multinucleated cells in close proximity to the Leydig cells were also stained with DPRP-1 antibody suggesting that the protease was also expressed in macrophages, and macrophages in the testis play an important role in the paracrine regulation of Leydig cells. Cytokines secreted by the testicular macrophages are mitogenic to Leydig cells and play an important role in the differentiation of mesenchymal progenitor cell into mature Leydig cells. A clearer understanding of the proteins and pathways involved in the maturation of the testis is important for the discovery of new treatments for precocious puberty. In addition, Leydig cells cause tumors such as sex cord-stromal tumors via sexual steroid production (predominantly testosterone). Testosterone is associated with several neoplasia and diseases such as breast carcinoma and uterine cancers, ovarian carcinoma and androgenic alopecia (hair loss). Further examination of the localization of DPRP proteins in other glands in the body (e.g. adrenal glands) that produce testosterone and other androgenic hormones are currently under investigation. The possible association of DPRP-1 with steroid and polypeptide hormone biosynthetic pathways functions is being investigated, and Example 7 is relevant to understanding the role of DPRP proteins in prostate, testis and breast in vitro cell models.

Immunohistochemical analysis also localized DPRP-1 to endometrial glands in the uterus (see Example 4), pancreatic acini, glomeruli of the kidney, plasma cells in the bladder, a subset of B-cells in the tonsils, columnar epithelial cells of the prostate and poorly differentiated prostate squamous metaplasia, Gleason grade 4 prostatic carcinoma, and hyperplastic glands in benign prostatic hyperplasia. Positive staining in breast carcinoma, as well as in seminoma and prostate squamous metaplasia, suggests a general association of DPRP-1 with hormone-sensitive tissues, particularly in cells that become poorly differentiated. The presence of the DPRP-1 in specialized epithelial cells and in inflammatory plasma cells (lymphocytes) is also of interest. Inflammatory breast carcinoma has an abundance of infiltrating lymphocytes and an overall bad prognosis. DPRP-1 and other DPRP proteins appear in medullary carcinomas that typically have a constant infiltrating lymphoplasmacytic component at the periphery of the tumor, which is thought to represent a reaction of the host tissues to the neoplasm. Most of the lymphocytes are T Cells, and most of the plasma cells are of the IgG-producing type. Several antigens are abundant on B cells, a subgroup of breast-cancer cells, and other epithelial cancer cells, and these antigens are targets for a new class of therapeutic monoclonal antibodies with some notable success having been achieved with a humanized monoclonal antibody against the B-cell-specific antigen CD20. Accordingly, monoclonal antibodies to DPRP proteins are felt to be useful to diagnose and treat diseases in which they are involved, including cancer.

The expression of DPRP-1 in specialized epithelial cells of a number of tissues suggests that DPRP-1 and other DPRP proteins may be involved in growth and differentiation thereof. Testing using inhibitors described in Example 6 in in vitro models of prostate and testis cancer (Example 7) showed that DPRP-1/DPRP-2 inhibitors caused a 50–60% increase in proliferation of PC3 cells at nM concentrations as shown in FIGS. 4A–4C.

Although the invention has been described in accordance with its preferred embodiments, which constitute the best mode presently known to the inventors, it should be understood that changes and modifications as would be obvious to those skilled in this art may be made without departing from its scope which is set forth in the claims appended hereto. For example, although the disclosure focuses on DPRP-1 and DPRP-2 in certain instances, DPRP-3 and its fragments are considered to be similarly useful, as are nucleic acids encoding same. The disclosures of all patents hereinbefore set forth are expressly incorporated herein by reference. Particular features of the invention are emphasized in the claims that follow.

SEQUENCE LISTING SUMMARY

SEQ ID.

1. DPRP1 a.a sequence
2. DPRP1 DNA sequence
3. DPRP2 a.a. sequence
4. DPRP2 DNA sequence
5. DPRP-3 a.a. sequence
6. DPRP-3 DNA sequence
7. DPRP-1 transcript 0 a.a. sequence
8. DPRP-1 transcript 0 DNA sequence
9. DPRP-1 transcript 1 a.a. sequence
10. DPRP-1 transcript 1 DNA sequence
11. DPRP-1 transcript 2 a.a. sequence
12. DPRP-1 transcript 2 DNA sequence
13. DPRP-1 transcript 3 a.a. sequence
14. DPRP-1 transcript 3 DNA sequence
15. DPRP-1 transcript 4 a.a. sequence
16. DPRP-1 transcript 4 DNA sequence
17. DPRP-1 transcript 5 a.a. sequence
18. DPRP-1 transcript 5 DNA sequence
19. DPRP-1 transcript 6 a.a. sequence
20. DPRP-1 transcript 6 DNA sequence
21. DPRP-1 transcript 7 a.a. sequence
22. DPRP-1 transcript 7 DNA sequence
23. DPRP-2 transcript 0 a.a. sequence
24. DPRP-2 transcript 0 DNA sequence
25. DPRP-2 transcript 1 a.a. sequence
26. DPRP-2 transcript 1 DNA sequence
27. DPRP-2 transcript 2 a.a. sequence
28. DPRP-2 transcript 2 DNA sequence 29. DPRP-2 transcript 3 a.a. sequence
30. DPRP-2 transcript 3 DNA sequence
31. DPRP-2 transcript 4 a.a. sequence
32. DPRP-2 transcript 4 DNA sequence
33. DPRP-2 transcript 5 a.a. sequence
34. DPRP-2 transcript 5 DNA sequence
35. DPRP-2 transcript 6 a.a. sequence
36. DPRP-2 transcript 6 DNA sequence
37. DPRP-2 transcript 7 a.a. sequence
38. DPRP-2 transcript 7 DNA sequence
39. DPRP-2 transcript 8 a.a. sequence
40. DPRP-2 transcript 8 DNA sequence
41. DPRP-3 transcript 0 a.a. sequence
42. DPRP-3 transcript 0 DNA. Sequence
43. DPRP-3 transcript 1 a.a. sequence
44. DPRP-3 transcript 1 DNA sequence
45. DPRP1 forward primer used for cloning
46. DPRP1 reverse primer used for cloning full length gene
47. DPRP1 reverse primer used for cloning fusion gene
48. DPRP1 forward primer used for expression profiling
49. DPRP1 reverse primer used for expression profiling
50. DPRP2 forward primer used for cloning
51. DPRP2 reverse primer used for cloning full length gene
52. DPRP2 reverse primer used for cloning fusion gene
53. DPRP2 forward primer used for expression profiling
54. DPRP2 reverse primer used for expression profiling
55. DPRP3 forward primer used for cloning
56. DPRP3 reverse primer used for cloning full length gene
57. DPRP3 forward primer used for cloning fusion gene
58. DPRP3 reverse primer used for cloning fusion gene
59. DPRP1 peptide antigen sequences
60. DPRP2 peptide antigen sequences
61. DPRP3 peptide antigen sequences

What is claimed is:

1. Isolated nucleic acid which encodes a polypeptide comprising the amino acid sequence of SEQ ID NO: 3 or a fragment thereof which exhibits prolyl oligopeptidase activity, or which is complementary to any one of the foregoing.

2. The isolated nucleic acid of claim 1 which is DNA or RNA.

3. The isolated nucleic acid of claim 1 which is a transcript of the entire length of SEQ ID NO: 4 or DNA which is complementary to the entire coding region of SEQ ID NO: 4.

4. An antisense oligonucleotide comprising a fragment of the nucleic acid of claim 1 which fragment inhibits expression of prolyl oligopeptidase.

5. The isolated nucleic acid of claim 1 which is an RNA transcript of the entire length of SEQ ID NO: 4.

6. A mammalian, insect or bacterial host cell which comprises an expression vector comprising the nucleic acid of claim 1 encoding a polypeptide having the entire amino acid sequence set forth in SEQ ID NO: 3 which nucleic acid is operably linked to a promoter.

7. An isolated recombinant polynucleotide molecule comprising nucleic acid according to claim 1 and expression-controlling elements linked operably with said nucleic acid to drive expression thereof.

8. A mammalian, insect or bacterial host cell that has been genetically engineered by the insertion of nucleic acid according to claim 1 which codes for a fragment of the amino acid sequence of SEQ ID NO: 3 which exhibits prolyl oligopeptidase activity.

9. The process for producing a polypeptide which includes a portion of SEQ ID NO: 3 exhibiting prolyl oligopeptidase activity, which process comprises culturing the host cell of claim 8 under conditions sufficient for the production of said polypeptide.

10. The process of claim 9 wherein said polypeptide is expressed at the surface of said cell and further includes the step of recovering the polypeptide or a fragment thereof from the culture.

11. The isolated nucleic acid of claim 1 which is DNA.

12. An isolated recombinant polynucleotide molecule comprising nucleic acid of SEQ ID NO: 4 an expression-controlling elements linked operably with said nucleic acid to drive expression thereon.

13. A mammalian, insect or bacterial host cell that has been genetically engineered by the insertion of nucleic which comprises SEQ ID NO:4.

14. A process for producing a polypeptide exhibiting prolyl oligopeptidase activity, which process comprises culturing the host cell of claim 13 under condition sufficient for the production of said polypeptide.

15. A purified polypeptide comprising the protein fragment of SEQ ID NO: 3 produced by the process of claim 9.

16. A mammalian, insect or bacterial host cell which comprises an expression vector comprising the polynucleotide of claim 12.

* * * * *